US012498379B2

(12) United States Patent
Anslyn et al.

(10) Patent No.: US 12,498,379 B2
(45) Date of Patent: Dec. 16, 2025

(54) SOLID-PHASE N-TERMINAL PEPTIDE CAPTURE AND RELEASE

(71) Applicant: BOARD OF REGENTS, THE UNIVERSITY OF TEXAS SYSTEM, Austin, TX (US)

(72) Inventors: Eric Anslyn, Austin, TX (US); Edward Marcotte, Austin, TX (US); Cecil J. Howard, II, Austin, TX (US); Jagannath Swaminathan, Austin, TX (US); Angela M. Bardo, Austin, TX (US); Brendan M. Floyd, Austin, TX (US); James Reuther, Lowell, MA (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1126 days.

(21) Appl. No.: 17/282,976

(22) PCT Filed: Oct. 4, 2019

(86) PCT No.: PCT/US2019/054702

§ 371 (c)(1),
(2) Date: Apr. 5, 2021

(87) PCT Pub. No.: WO2020/072907

PCT Pub. Date: Apr. 9, 2020

(65) Prior Publication Data

US 2021/0356473 A1 Nov. 18, 2021

Related U.S. Application Data

(60) Provisional application No. 62/879,735, filed on Jul. 29, 2019, provisional application No. 62/741,833, filed on Oct. 5, 2018.

(51) Int. Cl.

| | |
|---|---|
| ***G01N 33/68*** | (2006.01) |
| ***B01J 20/02*** | (2006.01) |
| ***B01J 20/22*** | (2006.01) |
| ***C07K 1/04*** | (2006.01) |
| ***C07K 17/06*** | (2006.01) |
| ***C07K 17/14*** | (2006.01) |
| ***C12Q 1/6804*** | (2018.01) |

(52) U.S. Cl.

CPC ...... *G01N 33/6824* (2013.01); *B01J 20/0229* (2013.01); *B01J 20/22* (2013.01); *C07K 1/042* (2013.01); *C07K 17/06* (2013.01); *C07K 17/14* (2013.01); *C12Q 1/6804* (2013.01)

(58) Field of Classification Search

CPC ......... C07K 1/042; C07K 17/06; C07K 17/14
See application file for complete search history.

(56) References Cited

U.S. PATENT DOCUMENTS

| | | | |
|---|---|---|---|
| 5,591,646 | A | 1/1997 | Hudson et al. |
| 5,605,809 | A | 2/1997 | Komoriya et al. |
| 5,902,723 | A | 5/1999 | Dower et al. |
| 5,914,313 | A | 6/1999 | Bouffard et al. |
| 6,156,527 | A | 12/2000 | Schmidt et al. |
| 6,326,136 | B1 | 12/2001 | Lazar et al. |
| 6,902,936 | B2 | 6/2005 | Qiu et al. |
| 7,329,505 | B2 | 2/2008 | Marmé |
| 7,351,540 | B1 | 4/2008 | Carr |
| 7,468,258 | B2 | 12/2008 | Owen |
| 7,641,862 | B2 | 1/2010 | Noetzel et al. |
| 8,268,977 | B2 | 9/2012 | Kool et al. |
| 8,569,481 | B2 | 10/2013 | Koster et al. |
| 8,609,423 | B2 | 12/2013 | Diller et al. |
| 8,778,685 | B2 | 7/2014 | Diller et al. |
| 9,011,772 | B2 | 4/2015 | Norderhaug et al. |
| 9,175,035 | B2 | 11/2015 | Konno et al. |
| 9,188,586 | B2 | 11/2015 | Fan et al. |
| 9,435,810 | B2 | 9/2016 | Havranek et al. |
| 9,470,680 | B2 | 10/2016 | Gonzalez et al. |
| 9,566,335 | B1 | 2/2017 | Emili et al. |
| 9,580,736 | B2 | 2/2017 | Tan et al. |
| 9,625,469 | B2 | 4/2017 | Marcotte et al. |
| 9,689,868 | B2 | 6/2017 | Kelts et al. |
| 9,983,211 | B2 | 5/2018 | Diller et al. |
| 10,088,488 | B2 | 10/2018 | Walker et al. |
| 10,302,591 | B2 | 5/2019 | Bogoev et al. |
| 10,473,654 | B1 | 11/2019 | Mallick |
| 10,481,162 | B2 | 11/2019 | Emili et al. |

(Continued)

FOREIGN PATENT DOCUMENTS

| | | |
|---|---|---|
| CN | 107614700 A | 1/2018 |
| EP | 1163519 | 12/2001 |

(Continued)

OTHER PUBLICATIONS

Extended European Search Report issued in European Application No. 19868673.5, dated Dec. 13, 2022.
Inoue, Nozomu et al. "Site-Specific Modification of Proteins through N-Terminal Azide Labeling and a Chelation-Assisted CuAAC Reaction." *Bioconjugate chemistry* vol. 30,9 (2019): 2427-2434.
Kim, Hwajeong et al. "Stable protein device platform based on pyridine dicarboxylic acid-bound cubic-nanostructured mesoporous titania films." *ACS applied materials & interfaces* vol. 5,15 (2013): 6873-8. doi: 10.1021/am401850n.
Machine Translation of WO 2019/168164, prepared Dec. 7, 2022.
Co-pending U.S. Appl. No. 17/491,485, inventors Marcotte; Edward et al., filed Sep. 30, 2021.

(Continued)

*Primary Examiner* — Sudhakar Katakam
(74) *Attorney, Agent, or Firm* — pH IP Law

(57) ABSTRACT

Provided herein are rapid and reversible methods to non-specifically immobilize peptides and proteins irrespective of their sequence, as well as small molecules, on a solid support to allow for manipulations of and reactions with these molecules in a manner that does not require purification between steps, which increases sample yield and reduces the quantity of starting material required.

6 Claims, 14 Drawing Sheets

Specification includes a Sequence Listing.

(56) References Cited

U.S. PATENT DOCUMENTS

| | | | |
|---|---|---|---|
| 10,520,515 B2 | 12/2019 | Manneh et al. | |
| 10,545,153 B2 | 1/2020 | Marcotte et al. | |
| 11,072,816 B2 | 7/2021 | Gaublomme et al. | |
| 11,105,812 B2 | 8/2021 | Marcotte et al. | |
| 11,136,349 B2 | 10/2021 | Macmillan et al. | |
| 11,143,648 B2 | 10/2021 | Ashworth et al. | |
| 11,162,952 B2 | 11/2021 | Marcotte et al. | |
| 11,435,358 B2 | 9/2022 | Marcotte et al. | |
| 2002/0081591 A1 | 6/2002 | Lukhtanov et al. | |
| 2002/0137045 A1* | 9/2002 | Lukhtanov | C07F 9/2408 435/6.12 |
| 2002/0168682 A1 | 11/2002 | Goodlett et al. | |
| 2002/0182117 A1 | 12/2002 | Coassin et al. | |
| 2004/0029181 A1 | 2/2004 | Ueyama et al. | |
| 2004/0053356 A1 | 3/2004 | Duewel et al. | |
| 2004/0059522 A1 | 3/2004 | Han et al. | |
| 2004/0086521 A1 | 5/2004 | Kropshofer et al. | |
| 2004/0152155 A1 | 8/2004 | Norioka et al. | |
| 2005/0003558 A1 | 1/2005 | Zuckermann et al. | |
| 2005/0020810 A1 | 1/2005 | Ternansky et al. | |
| 2007/0255455 A1 | 11/2007 | Busacca et al. | |
| 2008/0044405 A1 | 2/2008 | Dedecker et al. | |
| 2008/0090238 A1 | 4/2008 | Yang et al. | |
| 2008/0206141 A1 | 8/2008 | Johannesen et al. | |
| 2008/0242838 A1 | 10/2008 | Peters et al. | |
| 2009/0215635 A1 | 8/2009 | Carell et al. | |
| 2009/0264300 A1 | 10/2009 | Franch et al. | |
| 2010/0047170 A1 | 2/2010 | Denmeade et al. | |
| 2010/0047814 A1 | 2/2010 | Bruce et al. | |
| 2010/0233095 A1 | 9/2010 | Duan et al. | |
| 2010/0255518 A1 | 10/2010 | Goix et al. | |
| 2010/0331199 A1 | 12/2010 | Stoll et al. | |
| 2011/0027300 A1 | 2/2011 | Kamil et al. | |
| 2012/0100559 A1 | 4/2012 | Hell et al. | |
| 2013/0121915 A1 | 5/2013 | Paas et al. | |
| 2014/0024124 A1 | 1/2014 | Shinohara et al. | |
| 2014/0273004 A1 | 9/2014 | Havranek et al. | |
| 2014/0349860 A1 | 11/2014 | Marcotte et al. | |
| 2014/0378315 A1 | 12/2014 | Hendricks | |
| 2015/0065434 A1 | 3/2015 | Woster et al. | |
| 2015/0087526 A1 | 3/2015 | Hesselberth | |
| 2015/0185199 A1 | 7/2015 | Joo et al. | |
| 2015/0330879 A1 | 11/2015 | Mai | |
| 2016/0018351 A1 | 1/2016 | Kim et al. | |
| 2016/0194699 A1 | 7/2016 | Borodina et al. | |
| 2016/0238612 A1 | 8/2016 | Sims et al. | |
| 2016/0244828 A1 | 8/2016 | Mason | |
| 2017/0212126 A1 | 7/2017 | Emili et al. | |
| 2017/0242024 A1 | 8/2017 | Marcotte et al. | |
| 2017/0276686 A1 | 9/2017 | Marcotte et al. | |
| 2017/0343545 A1 | 11/2017 | Hadrup et al. | |
| 2018/0030531 A1 | 2/2018 | DeRaad | |
| 2018/0112212 A1 | 4/2018 | Nicol et al. | |
| 2018/0133715 A1 | 5/2018 | Craig et al. | |
| 2018/0179248 A1 | 6/2018 | MacMillan et al. | |
| 2018/0284125 A1 | 10/2018 | Gordon et al. | |
| 2019/0041385 A1 | 2/2019 | Schwartz et al. | |
| 2019/0085412 A1 | 3/2019 | Fan et al. | |
| 2019/0145982 A1 | 5/2019 | Chee et al. | |
| 2020/0018768 A1 | 1/2020 | Marcotte et al. | |
| 2020/0123593 A1 | 4/2020 | Rothberg et al. | |
| 2020/0123594 A1 | 4/2020 | Rothberg et al. | |
| 2020/0124613 A1 | 4/2020 | Marcotte et al. | |
| 2020/0209254 A1 | 7/2020 | Reed et al. | |
| 2020/0271661 A1 | 8/2020 | Sims | |
| 2020/0345599 A1 | 11/2020 | Son et al. | |
| 2020/0348307 A1 | 11/2020 | Beierle et al. | |
| 2021/0010070 A1 | 1/2021 | Schnall-Levin et al. | |
| 2021/0132076 A1 | 5/2021 | Marcotte et al. | |
| 2021/0215706 A1 | 7/2021 | Marcotte et al. | |
| 2021/0215707 A1 | 7/2021 | Marcotte et al. | |
| 2022/0002342 A1 | 1/2022 | MacMillan et al. | |
| 2022/0091130 A1 | 3/2022 | Marcotte et al. | |
| 2022/0163536 A1 | 5/2022 | Marcotte et al. | |

FOREIGN PATENT DOCUMENTS

| | | |
|---|---|---|
| EP | 2518514 | 10/2012 |
| EP | 3219712 | 9/2017 |
| EP | 3821010 | 5/2021 |
| GB | 2610078 | 2/2023 |
| JP | 2003-505109 | 2/2003 |
| JP | 2008-59703 | 11/2008 |
| JP | 2010-100542 | 5/2010 |
| WO | WO 91/00296 | 1/1991 |
| WO | WO 93/12230 | 6/1993 |
| WO | WO 01/09385 | 2/2001 |
| WO | WO 2006/117161 | 11/2006 |
| WO | WO-2007/070021 A1 | 6/2007 |
| WO | WO 2007/104219 | 9/2007 |
| WO | WO 2007/120805 | 10/2007 |
| WO | WO 2008/109176 | 9/2008 |
| WO | WO-2009/090651 A2 | 7/2009 |
| WO | WO 2009/158006 | 12/2009 |
| WO | WO-2009/158006 A2 | 12/2009 |
| WO | WO 2010/05322 | 1/2010 |
| WO | WO 2010/044892 | 4/2010 |
| WO | WO-2010/065322 A1 | 6/2010 |
| WO | WO 2010/065531 | 6/2010 |
| WO | WO 2012/019765 | 2/2012 |
| WO | WO 2012/071428 | 5/2012 |
| WO | WO 2012/083261 | 6/2012 |
| WO | WO 2012/178023 | 12/2012 |
| WO | WO 2013/112745 | 8/2013 |
| WO | WO-2014/031997 A1 | 2/2014 |
| WO | WO 2014/106957 | 7/2014 |
| WO | WO 2014/124338 | 8/2014 |
| WO | WO 2014/210353 | 12/2014 |
| WO | WO 2015/00893 | 1/2015 |
| WO | WO 2015/035108 | 3/2015 |
| WO | WO 2015/153381 A2 | 10/2015 |
| WO | WO-2015/200893 A2 | 12/2015 |
| WO | WO 2016/069124 | 5/2016 |
| WO | WO 2016/114970 | 7/2016 |
| WO | WO 2016/145409 | 9/2016 |
| WO | WO 2016/145416 | 9/2016 |
| WO | WO 2016/164530 | 10/2016 |
| WO | WO 2017/063093 | 4/2017 |
| WO | WO 2017/075265 | 5/2017 |
| WO | WO 2017/079573 | 5/2017 |
| WO | WO 2017/079593 | 5/2017 |
| WO | WO 2017/192633 | 11/2017 |
| WO | WO 2017/219027 | 12/2017 |
| WO | WO-2018/005559 A1 | 1/2018 |
| WO | WO 2018/075693 | 4/2018 |
| WO | WO 2018/119447 | 6/2018 |
| WO | WO 2018/140966 | 8/2018 |
| WO | WO 2019/063827 | 4/2019 |
| WO | WO 2019/089836 | 5/2019 |
| WO | WO 2019/089846 | 5/2019 |
| WO | WO 2019/089851 | 5/2019 |
| WO | WO 2019/125982 | 6/2019 |
| WO | WO 2019/168164 | 9/2019 |
| WO | WO 2019/178033 | 9/2019 |
| WO | WO 2020/014586 | 1/2020 |
| WO | WO-2020/014586 A1 | 1/2020 |
| WO | WO 2020/023488 | 1/2020 |
| WO | WO 2020/037046 | 2/2020 |
| WO | WO 2020/072907 | 4/2020 |
| WO | WO 2020/102741 | 5/2020 |
| WO | WO 2020/180335 | 9/2020 |
| WO | WO 2020/223133 | 11/2020 |
| WO | WO-2021/168083 A1 | 8/2021 |
| WO | WO-2021/211631 A2 | 10/2021 |
| WO | WO-2021/236716 A2 | 11/2021 |
| WO | WO-2022/182832 A1 | 9/2022 |
| WO | WO-2022/251419 A1 | 12/2022 |
| WO | WO-2022/251457 A2 | 12/2022 |

(56) References Cited

FOREIGN PATENT DOCUMENTS

WO WO-2023/019163 A1 2/2023
WO WO 2023/091961 A2 5/2023

OTHER PUBLICATIONS

English Translation of WO 2014/106957, published Jul. 10, -carbons with aryl halides." *Science* (New York, N.Y.) vol. 345,6195 (2014): 437-40. doi: 10.1126/science.1255525.
Zuo, Zhiwei, and David W C MacMillan. "Decarboxylative arylation of α-amino acids via photoredox catalysis: a one-step conversion of biomass to drug pharmacophore." *Journal of the American Chemical Society* vol. 136,14 (2014): 5257-60. doi: 10.1021/ja501621q.
"The catalog for Molecular Probes", downloaded from: web.archive.org/web/20101217092018/http://www.mobitec.de/probes/docs/sections/0101.pdf, available 2010.
Abelin et al., "Mass Spectrometry Profiling of HLA-Associated Peptidomes in Mono-allelic Cells Enables More Accurate Epitope Prediction." *Immunity* 46:315-326, 2017.
Aitken et al., "An Oxygen Scavenging System for Improvement of Dye Stability in Single-Molecule Fluorescence Experiments," *Biophysical Journal*, 94(5):1826-1835, 2008.
Altman et al., "Enhanced photostability of cyanine fluorophores across the visible spectrum," *Nature Methods*, 9:428-429, 2012.
Altman et al., "Cyanine fluorophore derivatives with enhanced photostability," *Nature Methods*, 9(1):68-71, 2012.
Andrews et al., "A Thermodynamic Model for Nap1-Histone Interactions", *J. Biol. Chem*., 283:32412-32418, 2008.
Antos et al., "Site-specific protein labeling via sortase-mediated transpeptidation", *Current protocols in protein science*, 89(1):15-3, 2017.
Armbrecht et al., "Single-cell protein profiling in microchambers with barcoded beads," *Microsyst Nanoeng*, 5(55), 2019.
Axelrod et al., "Cell-substrate contacts illuminated by total internal reflection fluorescence," *Journal of Cell Biology*, 89(1):141-145, 1981.
Backert & Kohlbacher, "Immunoinformatics and epitope prediction in the age of genomic medicine," *Genome Medicine*, 7(1):119, 2015.
Baez et al., "Mass Spectrometry in Studies of Protein Thiol Chemistry and Signaling: Opportunities and Caveats", *Free radical biology & medicine*, 80:191-211, 2015.
Bailey and Shively, "Carboxy-terminal sequencing: formation and hydrolysis of C-terminal peptidylthiohydantoins," *Biochemistry*, 29(12):3145-3156, 1990.
Balister et al., "Percolation, connectivity, coverage and colouring of random geometric graphs", *Handbook of Large-Scale Random Networks*, 18:117-142, 2008.
Bassani-Sternberg et al., "Mass spectrometry of human leukocyte antigen class I peptidomes reveals strong effects of protein abundance and turnover on antigen presentation," *Mol. Cell. Proteomics*., 14:658-73, 2015.
Bendall et al., "Single-Cell Mass Cytometry of Differential Immune and Drug Responses Across a Human Hematopoietic Continuum," *Science*, 332(6030):687-96, 2011.
Berg et al., "Peptide oligomers for holographic data storage," *Nature*, 383: 505-508, 1996.
Bethell et al., "Kinetics and mechanism of the Edman degradation," Chem. Comm., 10:189-190, 1965.
Bhat et al., "The visible touch: in planta visualization of protein-protein interactions by fluorophore-based methods," *Plant Methods*, 2(12), 2006.
Billingsley et al., "Single-molecule studies of DNA transcription using atomic force microscopy," *Phys. Biol*., 9:021001, 2012.
Bloom et al., "Decarboxylative alkylation for site-selective bioconjugation of native proteins via oxidation potentials," *Nature Chemistry*, 10(2):2015-2011, 2017.
Bonnet et al., "Amplifying Genetic Logic Gates," *Science*, 340(6132): 599-603, 2013.
Borgo et al., "Computer-aided design of a catalyst for Edman degradation utilizing substrate-assisted catalysis," *Protein Sci*., 24(4):571-579, 2015.
Bottecchia et al., "Photocatalytic modification of amino acids, peptides, and proteins", *Chemistry*, 25(1): 26-42, 2019.
Bradski et al., "OpenCV: an open-source computer vision library," Dr. Dobb's Journal of Software Tools, 2000.
Brandt et al., Quenching processes. www.rose-hulman.edu/~brandt/Fluorescence/Quenching_processes.pdf, downloaded Feb. 18, 2016.
Branton et al., "The potential and challenges of nanopore sequencing," *Nat. Biotechnol*., 26 (10): 1146-1153, 2008.
Braslavsky et al., "Sequence information can be obtained from single DNA molecules," *Proceedings of the National Academy of Sciences of the United States of America*, 100(7):3960-3964, 2003.
Brennick et al., "Neoepitopes as cancer immunotherapy targets: key challenges and opportunities", *Immunotherapy*, 9(4):361-71, 2017.
Brewis et al., "Proteomics technologies for the global identification and quantification of proteins", *Advances in Protein Chemistry*, 80(1):1-44, 2010.
Brosseron et al., "Stepwise isolation of human peripheral erythrocytes, T lymphocytes, and monocytes for blood cell proteomics," *Proteomics Clin. Appl*., 6(9-10):497-501, 2012.
Brown et al., "Neo-antigens predicted by tumor genome meta-analysis correlate with increased patient survival," *Genome Res*., 24:743-50, 2014.
Buschmann and Bystrykh., "Levenshtein error-correcting barcodes for multiplexed DNA sequencing", *BMC Bioinformatics* 14: 272, 2013.
Cafferty et al., "Storage of information using small organic molecules," *ACS Central Science*, 5: 911-916, 2019.
Cang et al., "Giant suppression of photobleaching for single molecule detection via the Purcell effect," *Nano Letters*,13(12):5949-5953, 2013.
Cannon et al., "A Dual-Mode Single-Molecule Fluorescence Assay for the Detection of Expanded CGG Repeats in Fragile X Syndrome," *Molecular Biotechnology*, 53(1): 19-28, 2013.
Caron et al., "A case for a human immuno-peptidome project consortium", *Immunity*, 47(2):203-8, 2017.
Caron et al., "Analysis of Major Histocompatibility Complex (MHC) Immunopeptidomes Using Mass Spectrometry", *Molecular & Cellular Proteomics*, 14(12):3105-3117, 2015.
Chalker et al., "Chemical Modification of Proteins at Cysteine: Opportunities in Chemistry and Biology," *Chemistry—An Asian Journal*, 4(5): 630-640, 2009.
Chang et al., "Manual solid phase sequence analysis of polypeptides using 4-N,N-dimethylaminoazobenzene 4'-isothiocyanate," *Biochim. Biophys. Acta*, 578(1):188-195, 1979.
Chen et al., "An efficient and versatile approach for the preparation of a rhodamine B ester bioprobe library," *Dyes and Pigments*, 94(2): 296-303, 2012.
Chen et al., "Reactivity of functional groups on the protein surface: development of epoxide probes for protein labeling." *Journal of the American Chemical Society*, 125(27): 8130-8133, 2003.
Chen et al., "Spatially resolved, highly multiplexed RNA profiling in single cells", *Science*, 348: 6233, 2015.
Choi et al., "Core-shell silica nanoparticles as fluorescent labels for nanomedicine," *J. of Biomedical Optics*, 12(6):064007, 2007.
Church et al., "Next-Generation Digital Information Storage in DNA." *Science*, 337(6102), 2012.
Cline et al., "Kinetics and mechanisms of the aminolysis of N-hydroxysuccinimide esters in aqueous buffers," *Journal of Organic Chemistry*, 53(15):3583-3586, 1988.
Cockrill et al., "Efficient micro-recovery and guanidination of peptides directly from MALDI target spots," *BioTechniques*, 38(2):301-304, 2005.
Cohen et al., "Red cell life span heterogeneity in hematologically normal people is sufficient to alter HbA1c," *Blood*, 112(10): 4284-4291, 2008.
Colombani et al., "Polymerization kinetics: monitoring monomer conversion using an internal standard and the key role of sample to." *J. Chem, Ed*., 88(1):116-121, 2011.

(56) References Cited

OTHER PUBLICATIONS

Cordes and Blum, "Opportunities and challenges in single-molecule and single-particle fluorescence microscopy for mechanistic studies of chemical reactions," *Nat. Chem.*, 5(12):993-999, 2013.
Cordes et al., "On the Mechanism of Trolox as Antiblinking and Antibleaching Reagent," *Journal of the American Chemical Society*, 131 (14): 5018-19, 2009.
Cuppoletti et al., "Oligomeric Fluorescent Labels for DNA," *Bioconjugate Chem.*, 16:528-534, 2005.
Czaplyski et al., "Substituent effects on the turn-on kinetics of rhodamine-based fluorescent pH probes," *Organic & Biomolecular Chemistry*, 12(3):526-533, 2014.
Da Costa et al., "How low can you go? A current perspective on low-abundance proteomics," *Trends in Analytical Chemistry*, 93: 171-182, 2017.
D'Amici et al., "Red blood cell storage in SAGM and AS3: a comparison through the membrane two-dimensional electrophoresis proteome," *Blood Transfus.*, 10, No. Suppl 2: s46-s54, 2012.
Declaration of Dr. Edward Marcotte filed in U.S. Appl. No. 14/128,247, filed Jul. 7, 2016.
Declaration of Dr. Edward Marcotte filed in U.S. Appl. No. 14/128,247, filed Sep. 2, 2016.
Declaration of Dr. Jagannath Swaminathan filed in U.S. Appl. No. 14/128,247, filed Jan. 26, 2016.
Dempsey et al., "Evaluation of fluorophores for optimal performance in localization-based super-resolution imaging," *Nat. Methods*, 8(12):1027-1036, 2011.
Doll et al., "Visualization of Protein-Specific Glycosylation inside Living Cells", *Angewandte Chemie International Edition*, 55(6): 2262-2266, Supporting Information, 2016.
Dong et al., "Label-free quantitation of glycated hemoglobin in single red blood cells by transient absorption microscopy and phasor analysis", *Sci Adv.*, 5(5): eaav0561, 2019.
Donnert et al., "Major signal increase in fluorescence microscopy through dark-state relaxation," *Nature Methods*, 4 (1): 81-86, 2006.
Dudley & Rosenberg, "Adoptive-cell-transfer therapy for the treatment of patients with cancer", *Nat. Rev. Cancer*, 3:666-675, 2003.
Duffy et al., "Clinical use of biomarkers in breast cancer: Updated guidelines from the European Group on Tumor Markers (EGTM)", *Eur. J. Cancer*, 75:284-298, 2017.
Dunn et al., "Techniques for phosphopeptide enrichment prior to analysis by mass spectrometry", *Mass Spectrometry Reviews*, 2009.
Edman et al., "A Protein Sequenator," *European Journal of Biochemistry*, 1(1):80-91, 1967.
Edman et al., "Method for determination of the amino acid sequence in peptides," *Acta Chemica Scandinavica*, 4(7): 283-293, 1950.
Edman et al., "Preparation of Phenyl Thiohydantoins from Some natural Amino Acids", *Acta Chemica Scandinavica*, 288-282, 1950.
Egloff et al., Engineered peptide barcodes for in-depth analyses of binding protein libraries, *Nature Methods*, 16: 421-428, 2018.
Eid et al., "Real-Time DNA Sequencing from Single Polymerase Molecules," *Science*, 323(5910): 133-138, 2009.
Eliason et al., "Temperature effect on reaction rates." *J. Chem. Ed.*, 58(4):354, 1981.
Ellson et al., Graphviz and Dynagraph—Static and Dynamic Graph Drawing Tools, *Graph Drawing Software: Mathematics and Visualization*, 127-148, 2004.
Eng et al., "An approach to correlate tandem mass spectral data of peptides with amino acid sequences in a protein database", *J. Am. Soc. Mass. Spectrom*, 5(11):976-989, 1994.
EP20150854171 European Search Report dated Feb. 12, 2018.
EP20150854171 Extended European Search Report dated Jun. 6, 2018.
EP20180215779 European Search Report dated Jul. 26, 2019.
Erdös & Rényi., "On the strength of connectedness of a random graph", *Acta Math. Acad. Sci. Hung.*, 12(1):261-267, 1964.
Feng et al., "Imaging Neuronal Subsets in Transgenic Mice Expressing Multiple Spectral Variants of GFP," *Neuron*, 28:41-51, 2000.
Fields et al., "The interplay of biology and technology," *PNAS*, 98(18):10051-10054, 2001.
Fredkin et al., "Trie memory," *Communications of the ACM*, 3(9): 490-499, 1960.
Frey et al., "Chemical Derivatization of Peptide Carboxyl Groups for Highly Efficient Electron Transfer Dissociation," *Journal of the American Society for Mass Spectrometry*, 24(11):1710-1721, 2013.
Fukuzaki et al., "Adsorption of protein onto stainless-steel surfaces," *J. Ferro. Bioeng.*, 80(1):6-11, 1995.
Gajer et al., "A Multi-dimensional Approach to Force-Directed Layouts of Large Graphs", *Lecture notes in Computer Science: International Symposium on Graph Drawing*, 84:211-221, 2002.
Garcia-Parajo et al., "The nature of fluorescence emission in the red fluorescent protein DsRed, revealed by single-molecule detection," *Proceedings of the National Academy of Sciences*, 98(25):14392-14397, 2001.
Garreau et al., "C-Terminal Bioconjugation of Peptides through Photoredox Catalyzed Decarboxylative Alkynylation," *Angewandte Chemie*, 58 (24):8182-8186, 2019.
Gawad et al., "Single-cell genome sequencing: current state of the science", *Nature Reviews Genetics*, 17(3): 175, 2016.
Ghaemmaghami et al., "Global analysis of protein expression in yeast," *Nature*, 425 :737-41, 2003.
Gilmore et al., "N-Terminal Protein Modification through a Biomimetic Transamination Reaction‡," *Angew. Chem. Int. Ed.*, 45:5307-5311, 2006.
Gnjatic et al., "Identifying baseline immune-related biomarkers to predict clinical outcome of immunotherapy", *J. Immunother. Cancer*, 5:44, 2017.
Godkin et al., "Characterization of novel HLA-DR11-restricted HCV epitopes reveals both qualitative and quantitative differences in HCV-specific CD4+ T cell responses in chronically infected and non-viremic patients." *Eur J Immunol.*, 31(5):1438-46, 2001.
Goodman et al., "Tumor Mutational Burden as an Independent Predictor of Response to Immunotherapy in Diverse Cancers", *Molecular Cancer Therapeutics*, 16(11):2598-608, 2017.
Gooley et al., "Glycosylation sites identified by detection of glycosylated amino acids released from Edman degradation: The identification of Xaa-Pro-Xaa-Xaa as a motif for Thr-O-glycosylation," *Biochemical and Biophysical Research Communications*, 178(3): 1194-1201, 1991.
Gullberg et al., "A sense of closeness: protein detection by proximity ligation", *Current Opinion in Biotechnology*, 14(1): 82-86, 2003.
Gyarmati et al., "Reversible disulphide formation in polymer networks: A versatile functional group from synthesis to applications", *European Polymer Journal*, 49:1268-1286, 2013.
Haab et al., "Applications of antibody array platforms," *Current Opinion in Biotechnology*, 17(4): 415-421, 2006.
Han et al., "Current developments in stepwise edman degradation of peptides and proteins," *International Journal of Biochemistry*, 17(4):429-445, 1985.
Hanay et al., "Single-protein nanomechanical mass spectrometry in real time," *Nature Nanotechnology*, 7(9): 602-608, 2012.
Haralambidis et al., "The preparation of polyamide-oligonucleotide probes containing multiple non-radioactive labels", *Nucleic Acids Research*, 18(3), 1990.
Harris et al., "Single-Molecule DNA Sequencing of a Viral Genome," *Science*, 320(5872): 106-109, 2008.
Harris et al., "Immuno-oncology combinations: raising the tail of the survival curve", *Cancer Biology & Medicine*, 13(2):171-93, 2016.
Hartmann et al., "A universal live cell barcoding-platform for multiplexed human single cell analysis," *Sci Rep.*, 8(1):1-10, 2018.
Havugimana et al., "A Census of Human Soluble Protein Complexes," *Cell*, 150(5): 1068-1081, 2012.
Herbrink et al., "Solid phase Edman degradation. High yield attachment of tryptic protein fragments to aminated supports," *FEBS Letters*, 60(2):313-316, 1975.
Hernandez et al., "Solution-phase and solid-phase sequential, selective modification of side chains in KDYWEC and KDYWE as models for usage in single-molecule protein sequencingt," *New J. Chem.*, 41(2):462-469, 2017.
Higgins et al., "Kinetic analysis of the nonenzymatic glycosylation of hemoglobin," *J. Biol. Chem.*, 256(10) :5204-5208, 1981.

(56) References Cited

OTHER PUBLICATIONS

Hoebe et al., "Controlled light-exposure microscopy reduces photobleaching and phototoxicity in fluorescence live-cell imaging," *Nature Biotechnology*, 25(2):249-253, 2007.
Horton et al., "A Highly Reactive Colored Reagent with Selectivity for the Tryptophan Residue in Proteins. 2-Hydroxy-5-nitrobenzyl Bromide[1]," *Journal of the American Chemical Society*, 87(5):1126-1132, 1965.
Huang et al., "Super resolution fluorescence microscopy," *Annu. Rev. Biochem.*, 78: 993-1016, 2009.
Huang et al., "Three-Dimensional Super-Resolution Imaging by Stochastic Optical Reconstruction Microscopy," *Science*, 319(5864): 810-813, 2008.
Hughes et al., "Single-cell western blotting", *Nat Methods*, 11(7):749-55. doi: 10.1038/nmeth.2992, 2014.
Hwang, et al., Identification of Missing Proteins in Human Olfactory Epithelial Tissue by Liquid Chromatography—Tandem Mass Spectrometry, *J Proteome Res*, 17(12):4320-4324 2018.
Imakyure et al., "A fluorogenic reagent for amino acids in liquid chromatography, 4-(2-cyanoisoindolyl)phenylisothiocyanate," Anal. Chim. Acta, 291(1-2):197-204, 1994.
Inglis et al., "Chemical procedures for C-terminal sequencing of peptides and proteins," *Anal. Biochem.*, 195(2):183-96, 1991.
Ingolia et al., "Genome-Wide Analysis in Vivo of Translation with Nucleotide Resolution Using Ribosome Profiling," *Science*, 324(5924):218-223, 2009.
International Search Report and Written Opinion issued in corresponding PCT Application No. PCT/US2019/46507, mailed on Dec. 10, 2019.
Ireland et al., "Double Coupling Edman Chemistry for High-Sensitivity Automated Protein Sequencing," *J. Protein Chem.*, 16(5):491-93, 1997.
Isidro-Llobet et al., "Amino acid-protecting groups," *Chemical Reviews*, 109(6):2455-2504, 2009.
Jain et al., "Stoichiometry and assembly of mTOR complexes revealed by single-molecule pulldown," *PNAS*, 111(50): 17833-17838, 2014.
Jameson et al., "Fluorescence Polarization/Anisotropy in Diagnostics and Imaging," Chem. Rev., 110 (5):2685-2708, 2010.
Jin et al., "Recent advances in dynamic covalent chemistry", *Chem Soc Rev*, 42(16):6634-54, 2013.
Jin et al., "Study on New Edman-type Reagents," *in Methods in Protein Sequence Analysis* (*Wittmann-Liebold, B., Ed.*), 34-41, Springer Berlin Heidelberg, Berlin, Heidelberg, 1989.
Johnson et al., "Reversible macrocyclization of peptides with a conjugate acceptor", *Organic letters*, 19(7): 1654-1657, 2017.
Joo et al., "Advances in Single-Molecule Fluorescence Methods for Molecular Biology," *Annual Review of Biochemistry*, 77:51-76,2008.
Julka et al., "Quantification in proteomics through stable isotope coding: a review," *Journal of Proteome Research*, 3(3):350-363, 2004.
Jungmann et al., "Quantitative super-resolution imaging with qPAINT," *Nat. Methods*, 13(5):439-442, 2016.
Kamada and Kawai., "An algorithm for drawing general undirected graphs", *Inf. Process. Lett.*, 31: 7-15, 1989.
Kamada and Soderberg., "Flow-assisted assembly of nanostructured protein microfibers", *Applied Physical Sciences*, 114(6):1232-1237, 2017.
Katritzky et al., "Fluorescent labeling of peptides on solid phase," *Org. Biomol. Chem.*, 6:4582-4586, 2008.
Kelly et al., "Targeted nanoparticles for imaging incipient pancreatic ductal adenocarcinoma," *PLoS Medicine*, 5(4), e85, 2008.
Keough et al., "Derivatization procedures to facilitate de novo sequencing of lysine-terminated tryptic peptides using postsource decay matrix-assisted laser desorption/ionization mass spectrometry," *Rapid Communications in Mass Spectrometry*,14(24):2348-2356, 2000.
Kim et al., "C-terminal de novo sequencing of peptides using oxazolone-based derivatization with bromine signature", *Anal. Biochem.*, 419:211-6, 2011.
Kinraide et al., "Use of a Gouy-Chapman-Stern model for membrane-surface electrical potential to interpret some features of mineral rhizotoxicity," *Plant Physiol.*, 106:1583-1592, 1994.
Klement et al., "Enrichment of O-GlcNAc modified proteins by the periodate oxidation-hydrazide resin capture approach", *J. Proteome Res.*, 9:2200-2206, 2010.
Ko et al., "Enhanced electron transfer dissociation of peptides modified at C-terminus with fixed charges," *Journal of American Society for Mass Spectrometry*, 23(11): 1991-2000, 2012.
Koide et al., "Development of NIR fluorescent dyes based on Si-rhodamine for in vivo imaging," *Journal of the American Chemical Society*, 134(11):5029-5031, 2012.
Konry et al., "Droplet-based microfluidic platforms for single T cell secretion analysis of IL-10 cytokine," *Biosens Bioelectron*, 26(5): 2707-2710, 2011.
Kool et al., "Fast Alpha Nucleophiles: Structures that Undergo Rapid Hydrazone/Oxime Formation at Neutral pH", *Organic Letters*, 16(5):1454-1457, 2014.
Koos et al., "Analysis of protein interactions in situ by proximity ligation assays," *Current Topics in Microbiology and Immunology*, 377:111-126, 2014.
Kovalova et al., "Stepwise triple-click functionalization of synthetic peptides", *Organic & biomolecular chemistry*, 16(33): 5960-5964, 2018.
Krusemark et al., "Complete chemical modification of amine and acid functional groups of peptides and small proteins," *Methods in molecular biology*, 753:77-91, 2011.
Kuyama et al., "An approach to quantitative proteome analysis by labeling tryptophan residues," *Rapid Communications in Mass Spectrometry*, 17(14):1642-1650, 2003.
Lakowicz et al., "Mechanisms and Dynamics of Fluorescence Quenching," In: *Principles of Fluorescence Spectroscopy*, 331-351. Boston, MA: Springer US, 2006.
Lamesch et al., "hORFeome v3.1: a resource of human open reading frames representing over 10,000 human genes," *Genomics*, 89: 307-315, 2007.
Lang and Chin, "Cellular Incorporation of Unnatural Amino Acids and Bioorthogonal Labeling of Proteins", *Chemical Reviews*, 114(9):4764-4806, 2014.
Laursen et al., "Solid-Phase Edman Degradation: An Automatic Peptide Sequencer," *European Journal of Biochemistry*, 20(1):89-102, 1971.
Lee et al., "A Simple Outline of Methods for Protein Isolation and Purification", *Endocrinol Metab*, 32(1):18-22, 2017.
Lee et al., "Evidence of preserved collagen in an Early Jurassic sauropodomorph dinosaur revealed by synchrotron FTIR microspectroscopy," *Nature Communications*, 8(1):1-8, 2017.
Lee et al., "Update on Tumor Neoantigens and Their Utility: Why It Is Good to Be Different", *Trends in Immunology*, 39(7):536-48, 2018.
Leigh-Smith et al., "Blood boosting," *British Journal of Sports Medicine*, 38(1): 99-101, 2004.
Li et al. "Synthesis and biological evaluation of nonsymmetrical aromatic disulfides as novel inhibitors of acetohydroxyacid synthase," *Bioorganic & Medicinal Chemistry Letters*, 23(13):3723-3727, 2013.
Li et al., "Constrained De Novo Sequencing of neo-Epitope Peptides using Tandem Mass Spectrometry", *Res Comut. Mol Bio.*, 10812:138-153, 2018.
Li et al., "N-terminal a-amino group modification of antibodies using a site-selective click chemistry method," *MABS* , 10(5):712-719, 2018.
Li et al., "Selective labeling of histidine by a designed fluorescein-based probe," *Talanta*, 62(2): 367-371, 2004.
Lin and Garcia., "Examining histone posttranslational modification patterns by high-resolution mass spectrometry", *Methods Enzymol.*, 512:3-28, 2012.
Lin et al., "Efforts and Challenges in Engineering the Genetic Code", *Life*, 7(1):1-12, 2017.
Liu et al., "On the dependency of cellular protein levels on mRNA abundance," *Cell*, 165: 535-550, 2016.

(56) References Cited

OTHER PUBLICATIONS

Lo et al., "Quantification of protein levels in single living cells," *Cell Reports*, 13:2634-2644, 2015.
Lotze et al., "Peptide-tags for site-specific protein labelling in vitro and in vivo", *Molecular Biosystems*, 12(6):1731-1745, 2016.
Luchowski et al., "Single molecule studies of multiple-fluorophore labeled antibodies. Effect of homo-FRET on the number of photons available before photobleaching," *Curr. Pharm. Biotechnol.*, 9(5):411-420, 2008.
Lukinavious et al., "A near-infrared fluorophore for live-cell super-resolution microscopy of cellular proteins," *Nature Chemistry*, 5(2):132-139, 2013.
Lyon et al., "Self-hydrolyzing maleimides improve the stability and pharmacological properties of antibody-drug conjugates," *Nat. Biotechnol.*, 32(10):1059-1062, 2014.
Macbeath et al., "Printing small molecules as microarrays and detecting protein-ligand interactions en masse," *Journal of the American Chemical Society*, 121(34):7967-7968, 1999.
MacDonald et al., "One-step site-specific modification of native proteins with 2-pyridinecarboxyaldehydes," *Nat. Chem. Biol.*, 11(5):326-331, 2015.
Maiti et al., "Bifunctional aryloxyphosphoramidate prodrugs of 2'-C-Me-uridine: synthesis and anti-HCV activity", *Organic & biomolecular chemistry*,14(37): 8743-8757, 2016.
Mallam et al., "Systematic discovery of endogenous human ribonucleoprotein complexes," *Cell Rep.*, 29(5): 1351-1368.e5, 2019.
Margulies et al., "Genome sequencing in microfabricated high-density picolitre reactors", *Nature*, 437: 376-380 ,2005.
Matsunaga et al., "Proton: a major factor for the racemization and the dehydration at the cyclization/cleavage stage in the Edman sequencing method," *Anal. Chem.*, 68(17) :2850-2856, 1996.
Maude et al., "Tisagenlecleucel in Children and Young Adults with B-Cell Lymphoblastic Leukemia", *New England Journal of Medicine*, 378(5):439-48, 2018.
Mazutis et al., "Single-cell analysis and sorting using droplet-based microfluidics," *Nat. Protoc.*, 8(5): 870-891, 2013.
Mazzone et al., "Evaluating Molecular Biomarkers for the Early Detection of Lung Cancer: When Is a Biomarker Ready for Clinical Use? An Official American Thoracic Society Policy Statement", *Am. J. Respir. Crit. Care Med.*, 196: e15-e29, 2017.
Mcalpine et al., "Visualizing Functional Group Distribution in Solid-Support Beads by Using Optical Analysis," *Chemistry—A European Journal*, 5(12):3528-3532, 1999.
Merrifield et al., "Solid Phase Peptide Synthesis. I. The Synthesis of a Tetrapeptide", *J. Am. Chem. Soc.*, 85:2149-2154, 1963.
Millington et al., "Aryl hydrazides as linkers for solid phase synthesis which are cleavable under mild oxidative conditions," *Tetrahedron Letters*, 39(39): 7201-7204, 1998.
Miyashita et al., "Attomole level protein sequencing by Edman degradation coupled with accelerator mass spectrometry," *Proc. Natl. Acad. Sci.*, 98(8):4403-4408, 2001.
Moffett et al., "Tryptophan and the immune response," *Immunology and Cell Biology*, 81(4):247-265, 2003.
Mohanty et al., "Advancing cell biology and functional genomics in maize using fluorescent protein-tagged lines," *Plant Physiology*, 149: 601-605, 2009.
Momaya et al., "Performance-Enhancing Substances in Sports: A Review of the Literature," *Sports Med.*, 45(4): 517-531, 2015.
Monfort et al., "Plasticizers excreted in urine: indication of autologous blood transfusion in sports," *Transfusion* (Paris), 52(3):647-657, 2012.
Müller et al., "Current Strategies for the Identification of Immunogenic Epitopes of Tumor Antigens", *Immunotherapy of Cancer*, 21-44, 2006.
Muramoto et al., "The application of fluorescein isothiocyanate and high-performance liquid chromatography for the microsequencing of proteins and peptides," *Anal. Biochem.*, 141(2):446-450, 1984.
Nagaraj et al., "Deep proteome and transcriptome mapping of a human cancer cell line," *Molecular Systems Biology*, 7:548-548, 2011.
Neefjes et al., "Towards a systems understanding of MHC class I and MHC class II antigen presentation", *Nat. Rev. Immunol.*, 11 :823-836, 2011.
Niall et al., "[36] Automated edman degradation: The protein sequenator," *Methods in Enzymology* 27, 942-1010, 1973.
Nikon et al., "Nikon microscopes educational literature", www.microscopyu.com/references/photobleaching.html, 2010.
Nivala et al., "Unfoldase-mediated protein translocation through an α-hemolysin nanopore," *Nature Biotechnology*, 31(3):247-250, 2013.
Nuijens et al., "Improved solid phase synthesis of peptide carboxyamidomethyl (Cam) esters for enzymatic segment condensation", *Tetrahedron Letters*, 57(32): 3635-3638, 2016.
Office Communication issued in GB1322371.4, dated Jul. 29, 2019.
Office Communication issued in GB1322371.4, dated Nov. 26, 2018.
Oquare et al., Design and synthesis of peptide nucleic acid (PNA) agents for imaging gene expression, in *Department of Chemistry*, Washington University, 2007.
Ortiz et al., "Design of multivalent fluorescent dendritic probes for site-specific labeling of biomolecules," *Journal of Polymer Science, Part A: Polymer Chemistry*, 56:1609-1616, 2018.
PCT International Search Report and Written Opinion issued in International Application No. PCT/US2019/041562, dated Oct. 11, 2019.
PCT International Search Report and written opinion issued in International Application No. PCT/US19/46507, dated Dec. 10, 2019.
PCT International Search Report and written opinion issued in International Application No. PCT/US2019/042998, dated Oct. 31, 2019.
PCT International Search Report and Written Opinion issued in International Application No. PCT/US2019/54702, dated Feb. 6, 2020.
PCT International Search Report and Written Opinion issued in International Application No. PCT/US2015/050099, dated Apr. 11, 2015.
PCT International Search Report of International Application No. PCT/US2012/043769 dated Oct. 4, 2012.
Penrose, *Random geometric graphs*. (Oxford University Press, 2003).
Peplow et al., "Molecular data-storage system encodes information with peptides," *Chemical and Engineering News*, 2019.
Perron et al., "Derivatives of 6-aminopenicillanic acid. II. Reactions with isocyanates, isothiocyanates, and cyclic anhydrides," *Journal of Organic Chemistry*, 26(9):3365-3367, 1961.
Petersdorf et al., "The International Histocompatibility Working Group in Hematopoietic Cell Transplantation", *Int. J. Immunogenet.*, 40(1), 2013.
Pham et al., "An Update on Immunotherapy for Solid Tumors : A Review", *Annals of Surgical Oncology*, 25(11) :3404-12, 2018.
Phatnani & Greenleaf, "Phosphorylation and functions of the RNA polymerase II CTD", *Genes Dev*, 20 :2922-2936, 2006.
Pickens et al., "Practical considerations, challenges, and limitations of bioconjugation via azide-alkyne cycloaddition," *Bioconj. Chem.*, 29(3):686-701, 2018.
Pieroni et al., "Reaction of diazonium salt with tyrosine residues in polypeptides," *Die Makromolekulare Chemie*, 176(11):3201-3209, 1975.
Pirrung et al., "How to make a DNA chip", *Angew. Chem. Int. Ed.* 41:1276-1289, 2002.
Powell and Tempst., "Microflow-based automated chemistries: application to protein sequencing," *Anal. Chem.*, 73(4):776-786, 2001.
Previero et al., "Solid phase sequential analysis: Specific linking of acidic peptides by their carboxyl ends to insoluble resins," *FEBS Letters*, 33(1):135-138, 1973.
Prosenz et al., "Glycated hemoglobin concentrations of red blood cells minimally increase during storage under standard blood banking conditions," *Transfusion*, 59(2):454-457, 2019.

(56) References Cited

OTHER PUBLICATIONS

Prudent et al., "Proteomics of stored red blood cell membrane and storage-induced microvesicles reveals the association of flotillin-2 with band 3 complexes," *Front. Physiol.*, 9:421, 2018.
Quick et al., "SITS Derivatization of Peptides to Enhance 266 nm Ultraviolet Photodissociation (UVPD)", *Journal of The American Society for Mass Spectrometry*, 28(7):1462-1472, 2017.
Robbins et al., "A pilot trial using lymphocytes genetically engineered with an NY-ESO-1-reactive T-cell receptor : long-term follow-up and correlates with response", *Clinical Cancer Research*, 21(5) :1019-27, 2015.
Romond et al., "Trastuzumab plus adjuvant chemotherapy for operable HER2-positive breast cancer," *New England Journal of Medicine*, 353(16):1673-1684, 2005.
Roper Scientific, Datasheet for 1-pentarnax camera, www.spectracore.coru/cameras/pdf/ipgeniti.pdf, 2015.
Rosenbaum et al., "Solid phase synthesis of cyclic peptides by oxidative cyclative cleavage of an aryl hydrazide linker-synthesis of stylostatin 1," *Tetrahedron Letters*, 42:5677-5680, 2001.
Rothbauer et al., "Speed up to find the right ones: rapid discovery of functional nanobodies," *Nature structural & molecular biology*, 25(3): 199-201, 2018.
Rutten et al., "Encoding information into polymers," *Nature Reviews: Chemistry*, 2:365-381, 2018.
Ryazantsev et al., "Two-dye and one- or two-quencher DNA probes for real-time PCR assay: synthesis and comparison with a TaqMan™ probe," *Anal Bioanal Chem.*, 404:59-68, 2012.
Saiz et al., "Reversible Thiazolidine Exchange: A New Reaction Suitable for Dynamic Combinatorial Chemistry", *Organic Letters*, 11(15):3170-3173, 2009.
Salehi-Reyhani et al., "A first step towards practical single cell proteomics: a microfluidic antibody capture chip with TIRF detection," *Lab on a Chip*, 11(7):1256-61, 2011.
Saul et al., "Development of a full-length human protein production pipeline," *Protein Science*, 23(8): 1123-1135, 2014.
Sawyers et al., "The cancer biomarker problem," *Nature*, 452(7187):548-552, 2008.
Scangarello et al., "*Application of Multivalent Displays on Metalloprotease-Dependent Cleavage of Semaphorin 4D in Synapse Development*", in Department of Biochemistry, Brandeis University, 2012.
Schaus et al., "A DNA nanoscope via auto-cycling proximity recording," *Nature Communications*, 8(696):1-9, 2017.
Schmidt et al., "Omniligase-1: a powerful tool for peptide head-to-tail cyclization," *Advanced Synthesis & Catalysis*, 359(12):2050-2055, 2017.
Schmidt et al., "The struggle to do no harm", *Nature*, 552:S74, 2017.
Schnatbaum et al., "The challenge of complexity: Peptide tools for the development of immunotherapies", Poster—*Innovative Peptide Solutions*, 2016.
Schumacher & Schreiber, "Neoantigens in cancer immunotherapy", *Science*, 348(6230):69-74, 2015.
Schwammle et al., "Systems Level Analysis of Histone H3 Post-translational Modifications (PTMs) Reveals Features of PTM Cross-talk in Chromatin Regulation*", *Molecular & Cellular Proteomics*, 13(7):1855-1865, 2014.
Scoffone et al., "Selective modification of the tryptophan residue in peptides and proteins using sulfenyl halides," *Biochemical and Biophysical Research Communications*, 25(2):170-174, 1966.
Scoffone et al., "Sulfenyl halides as modifying reagents for polypeptides and proteins. I. Modification of tryptophan residues," *Biochemistry*, 7(3):971-979,1968.
Segura et al., "Detection methods for autologous blood doping," *Drug Test. Anal.*, 4(11): 876-881, 2012.
Shendure et al., DNA sequencing at 40: past, present and future, *Nature*, 550:345-353, 2017.
Shi et al., "Single-cell proteomic chip for profiling intracellular signaling pathways in single tumor cells," *PNAS*, 109(2): 419-424, 2012.
Shimabukuro-Vornhagen et al., "Cytokine release syndrome", *Journal for Immunotherapy of Cancer*, 6(56), 2018.
Shimko et al., "Preparing semisynthetic and fully synthetic histones H3 and H4 to modify the nucleosome core", *Methods in Molecular Biology*, 981:177-192, 2013.
Sigal et al., Mapping Synaptic Input Fields of Neurons with Super-Resolution Imaging, *Cell*, 163(2):493-505, 2015.
Song et al., "Photobleaching kinetics of fluorescein in quantitative fluorescence microscopy," *Biophysical Journal*, 68(6):2588-2600, 1995.
Soni and Meller., "Progress toward ultrafast DNA sequencing using solid-state nanopores," *Clin Chem*, 53: 1996-2001, 2007.
Steen et al., "Phosphorylation analysis by mass spectrometry: myths, facts, and the consequences for qualitative and quantitative measurements", *Mol Cell Proteomics*, 5(1):172-81, 2006.
Stevanovic et al., "Multiple Sequence Analysis: Pool Sequencing of Systemic and Natural Peptide Libraries", *Analytical Biochemistry*, 212(1):212-220, 1993.
Stevens et al., "Enhancement of phosphoprotein analysis using a fluorescent affinity tag and mass spectrometry", *Rapid Commun Mass Spectrom.*, 19:2157-2162, 2005.
Supplemental Search Report issued in European Application No. 15854171.4, dated Feb. 12, 2018.
Supplemental Search Report issued in European Application No. 19849103.7, dated May 16, 2022.
Supplemental Search Report issued in European Application No. 19834092.9, dated May 3, 2022.
Swaminathan et al., "A theoretical justification for single molecule peptide sequencing." *PLoS computational biology*, 11(2), 2015.
Swaminathan et al., "Highly parallel single-molecule identification of proteins in zeptomole-scale mixtures", *Nat. Biotechnol.*, Accepted 2018.
Swaminathan et al., "Peptide Fragment Ion Analyser (PFIA): a simple and versatile tool for the interpretation of tandem mass spectrometric data and de novo sequencing of peptides", *Rapid Commun. Mass Spectrom.*, 21: 3033-3038,2007.
Swoboda et al., "Enzymatic oxygen scavenging for photostability without pH drop in single-molecule experiments," *ACS Nano*, 6(7), 2012.
Szymczak et al., "Peptide arrays: development and application," *Anal Chem.*, 90(1): 266-282, 2008.
Tang et al., "Development and applications of single-cell transcriptome analysis," *Nat Methods.*, 8(4 Suppl):S6-11. doi: 10.1038/nmeth.1557, 2011.
Taylor et al., "Aminopeptidases: structure and function." *FASEB*, 7(2):290-298, 1993.
Tessier et al., "Doubly Orthogonal Labeling of Peptides and Proteins," *Chem*, 5(8): 2243-2263, 2019.
Thakur et al., "Deep and highly sensitive proteome coverage by LC-MS/MS without prefractionation," *Molecular & Cellular Proteomics*, 10(8), 2011.
The Scientist Solution Forum, http://www.scientistsolutions.com/t11153-keratin+contamination.html., 2009.
The University of Cambridge, Michaelis-Menten equation, http://wwwjmg.ch.cam.ac.uk/tools/magnus/michmenten.html., 2009.
Thermo Scientific, "Thermo Scientific Pierce Cross-Linking Reagents Technical Handbook," 1-48, 2005.
Thoma et al., "The ABRF Edman Sequencing Research Group 2008 Study: investigation into homopolymeric amino acid N-terminal sequence tags and their effects on automated Edman degradation," *J. Biomol. Tech.*, 20(4):216-225, 2009.
Tillberg et al., "Protein-retention expansion microscopy of cells and tissues labeled using standard fluorescent proteins and antibodies," *Nat Biotechnol.*, 34(9):987-92, 2016.
Tokeshi et al., "Single-and countable-molecule detection of non-fluorescent molecules in liquid phase," *J. Luminesce.*,83 :261-264, 1999.
Toseland et al., "Fluorescent labeling and modification of proteins" *Journal of chemical biology*, 6(3): 85-95, 2013.
Totaro et al., "Systematic Investigation of EDC/sNHS-Mediated Bioconjugation Reactions for Carboxylated Peptide Substrates", *Bioconjug. Chem.*, 27:994-1004, 2016.

(56) References Cited

OTHER PUBLICATIONS

Tulla-Puche et al., "The (classic concept of) solid support," in the power of functional resins in organic synthesis (Tulla-Puche, J., et al., Eds.), 3-14, Wiley, Weinheim, 2008.
Tung et al., "Preparation of a cathepsin D sensitive near-infrared fluorescence probe for imaging," *Bioconjugate Chemistry*, 10(5): 892-896, 1999.
Tyler et al., "Evaluation of Oxford Nanopore's MinION sequencing device for microbial whole genome sequencing applications," *Sci. Rep.*, 8(1):10931, 2018.
U.S. Appl. No. 14/128,247 Notice of Allowance dated Dec. 6, 2016.
U.S. Appl. No. 14/128,247 Office Action dated Mar. 9, 2016.
U.S. Appl. No. 14/128,247 Office Action dated Oct. 28, 2015.
U.S. Appl. No. 15/461,034 Office Action dated Jun. 29, 2018.
U.S. Appl. No. 15/461,034 Office Action dated Nov. 20, 2018.
U.S. Appl. No. 15/510,962 Notice of Allowance dated Sep. 11, 2019.
U.S. Appl. No. 15/510,962 Office Action dated Dec. 6, 2018.
U.S. Appl. No. 15/510,962 Office Action dated May 3, 2019.
Ulbrich et al., "Subunit counting in membrane-bound proteins," *Nature Methods*, 4(4):319-321, 2007.
Villain et al., "Chemical Ligation of Multiple Peptide Fragments Using a New Protection Strategy", *Chemistry & Biology*, 8(7):673-679, 2001.
Vitiello and Zanetti, "Neoantigen prediction and the need for validation," *Nature Biotechnology*, 35(9):815-7, 2017.
Volkmann et al., "Protein C-terminal labeling and biotinylation using synthetic peptide and split-intein," *PLoS ONE*, 4(12): e8381, 2009.
Wainaina et al., "Fluorescence detection of amino acids in the postcleavage conversions for manual sequencing of a peptide," *Analytical Biochemistry*, 374(2), 423-425, 2008.
Waliczek et al., "Peptides Labeled with Pyridinium Salts for Sensitive Detection and Sequencing by Electrospray Tandem Mass Spectrometry", *Sci Rep*, 6:37720, 2016.
Wan et al., "Panorama of ancient metazoan macromolecular complexes," Nature, 525:339-344, 2015.
Wang et al., "The covalent trimethoprim chemical tag facilitates single molecule imaging with organic fluorophores," *Biophysical Journal*, 106(1):272-278, 2014.
Wiese et al., "Protein labeling by iTRAQ: A new tool for quantitative mass spectrometry in proteome research", *Proteomics*, 7:340-350, 2007.
Wittmann et al., "Combinatorial Solid-Phase Synthesis of Multivalent Cyclic Neoglycopeptides," *Angewandte Chemie International Edition*, 39(23): 4348-4352, 2000.
Xu et al., "Chemoenzymatic labeling of protein C-termini for positive selection of C-terminal peptides," *ACS Chem. Biol.*, 6(10):1015-1020, 2011.
Yadav et al., "Predicting immunogenic tumour mutations by combining mass spectrometry and exome sequencing", *Nature*, 515:572-576, 2014.
Yang et al., "Single-cell, multiplexed protein detection of rare tumor cells based on a beads-on-barcode antibody microarray," *Analytical chemistry*, 88(22):11077-11083, 2016.
Yee & Lizee, "Personalized Therapy: Tumor Antigen Discovery for Adoptive Cellular Therapy", *Cancer J.*, 23:144-148, 2017.
Yee et al., "Endogenous T-Cell Therapy: Clinical Experience", *Cancer J.*, 21:492-500, 2015.
Yewdell et al., "Making sense of mass destruction: quantitating MHC class I antigen presentation," *Nat. Rev. Immunol.*, 3:952-961, 2003.
Yuan et al., "A rational approach to tuning the p K a values of rhodamines for living cell fluorescence imaging," *Organic & Biomolecular Chemistry*, 9(6):1723-1726, 2011.
Zervas et al., "New methods in peptide synthesis. I. Tritylsulfenyl and o-nitrophenylsulfenyl groups as N-protecting groups," *Journal of the American Chemical Society*, 85(22):3660-3666, 1963.
Zhang et al., "Thiol Specific and Tracelessly Removable Bioconjugation via Michael Addition to 5-Methylene Pyrrolones," *J. Am. Chem. Soc.*, 139(17):6146-6151, 2017.
Zhao et al., "Single-molecule spectroscopy of amino acids and peptides by recognition tunnelling," *Nature Nanotechnology*, 9(6): 466-473, 2014.
Zheng et al., "The contribution of reactive oxygen species to the photobleaching of organic fluorophores," *Photochemistry and Photobiology*, 90(2):448-454, 2014.
Zheng et al., "Ultra-stable organic fluorophores for single-molecule research," *Chemical Society Reviews*, 43(4):1044-1056, 2014.
Duffy et al., "Clinical use of biomarkers in breast cancer: Updated guidelines from the European Group on Tumor Markers (BGTM)", *Eur. J. Cancer*, 75:284-298, 2017.
Hernandez et al., "Solution-phase and solid-phase sequential, selective modification of side chains in KDYWEC and KDYWE as models for usage in single-molecule protein sequencing†," *New J. Chem.*, 41(2):462-469, 2017.
Li et al., "N-terminal α-amino group modification of antibodies using a site-selective click chemistry method," *MABS* , 10(5):712-719, 2018.
Roper Scientific, Datasheet for 1-pentarnax camera, www.spectracore.coru/cameras/pdf/ipgeniii.pdf, 2015.
CN 201980074385.7 Office Communication dated Jan. 30, 2024.

* cited by examiner

FIGS. 7A-B

A)
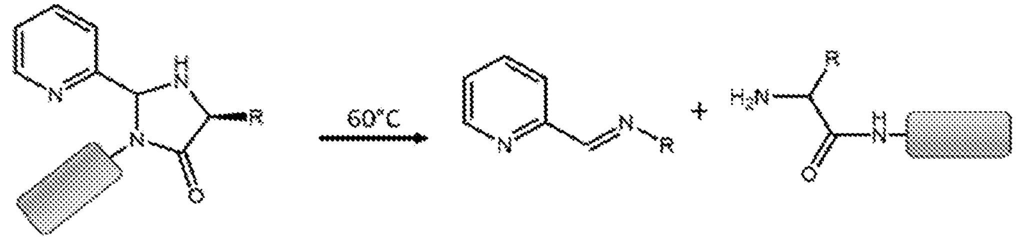
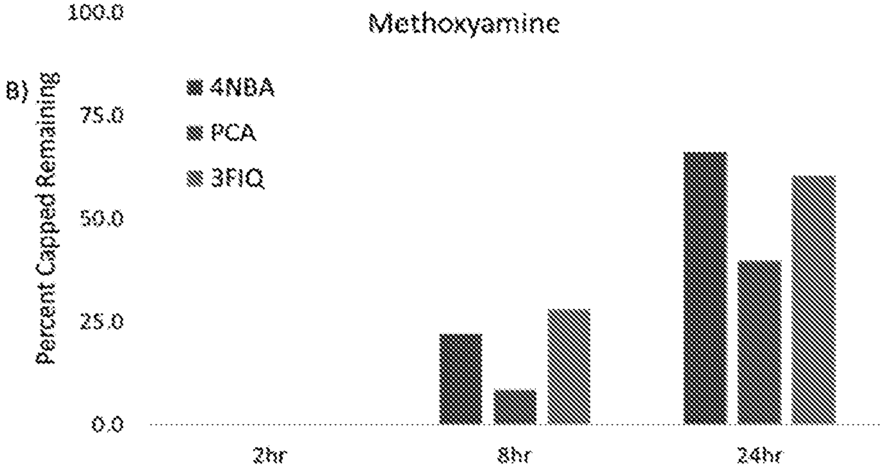
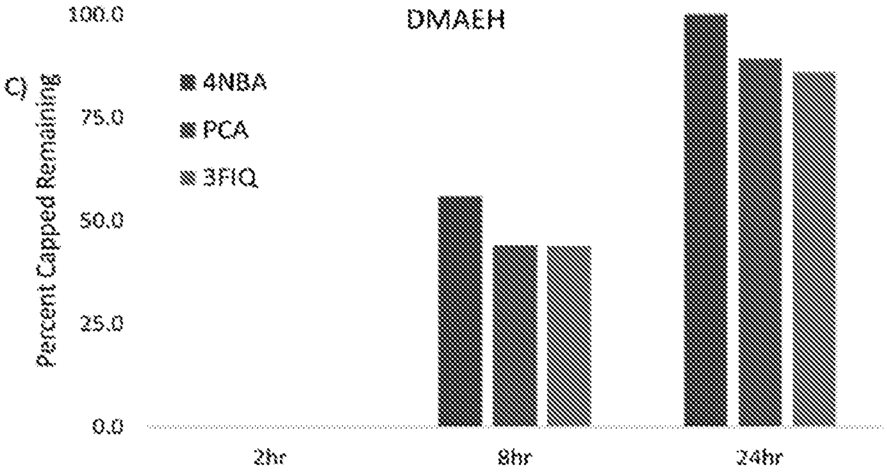
FIGS. 10A-C

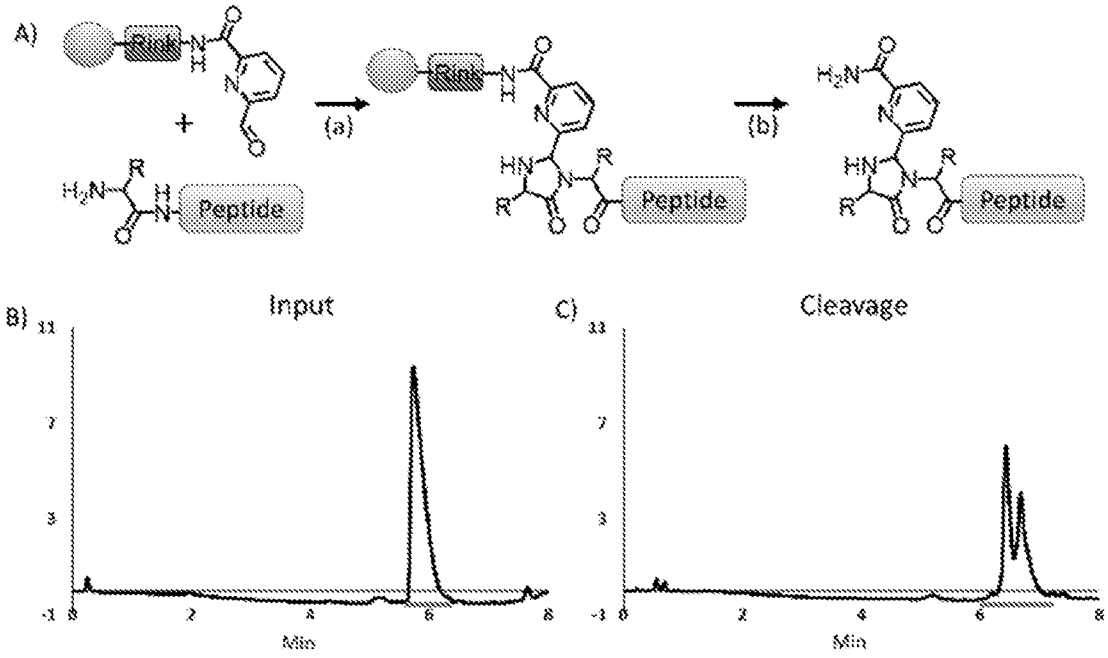
FIGS. 12A-C

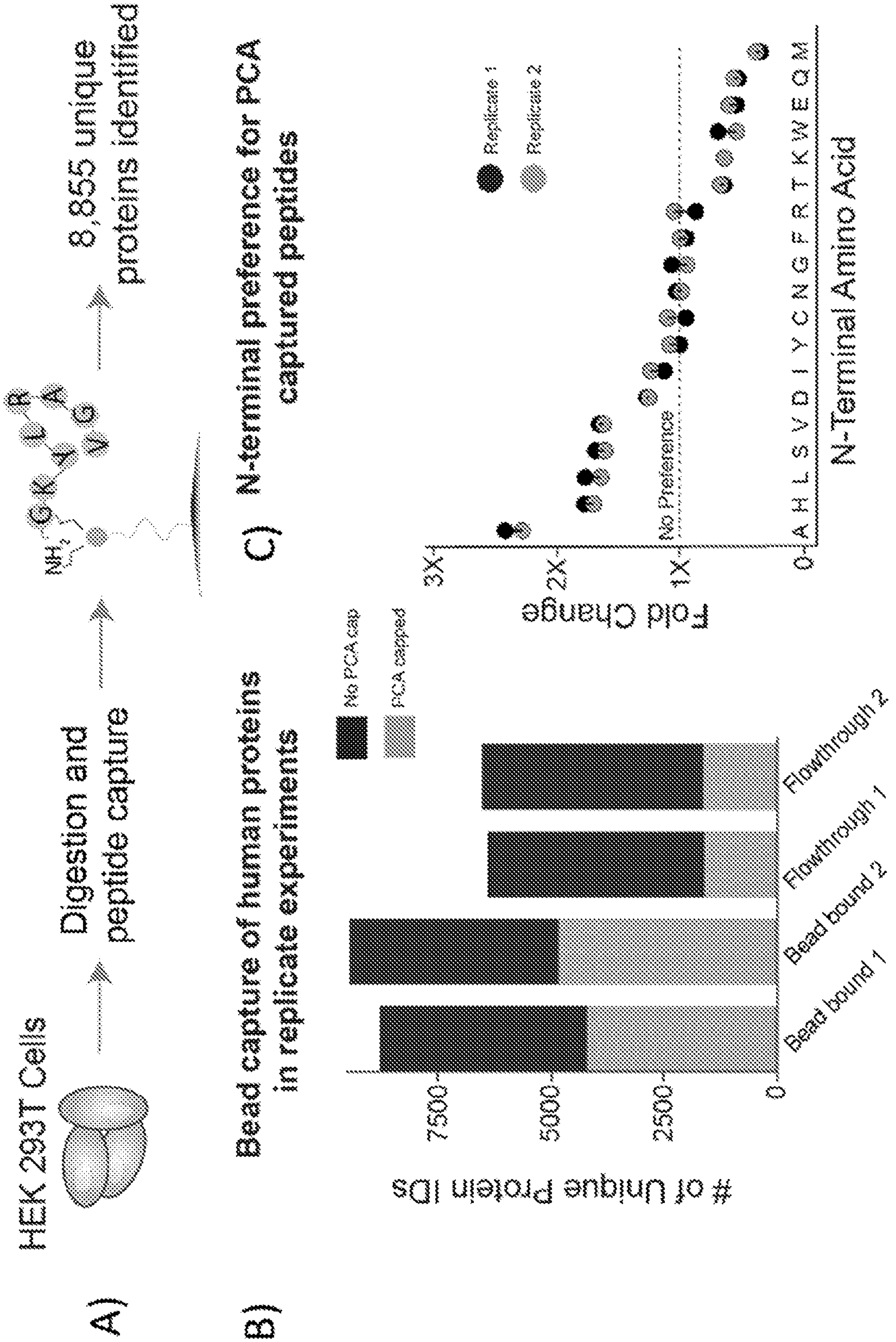
FIGS. 13A-C

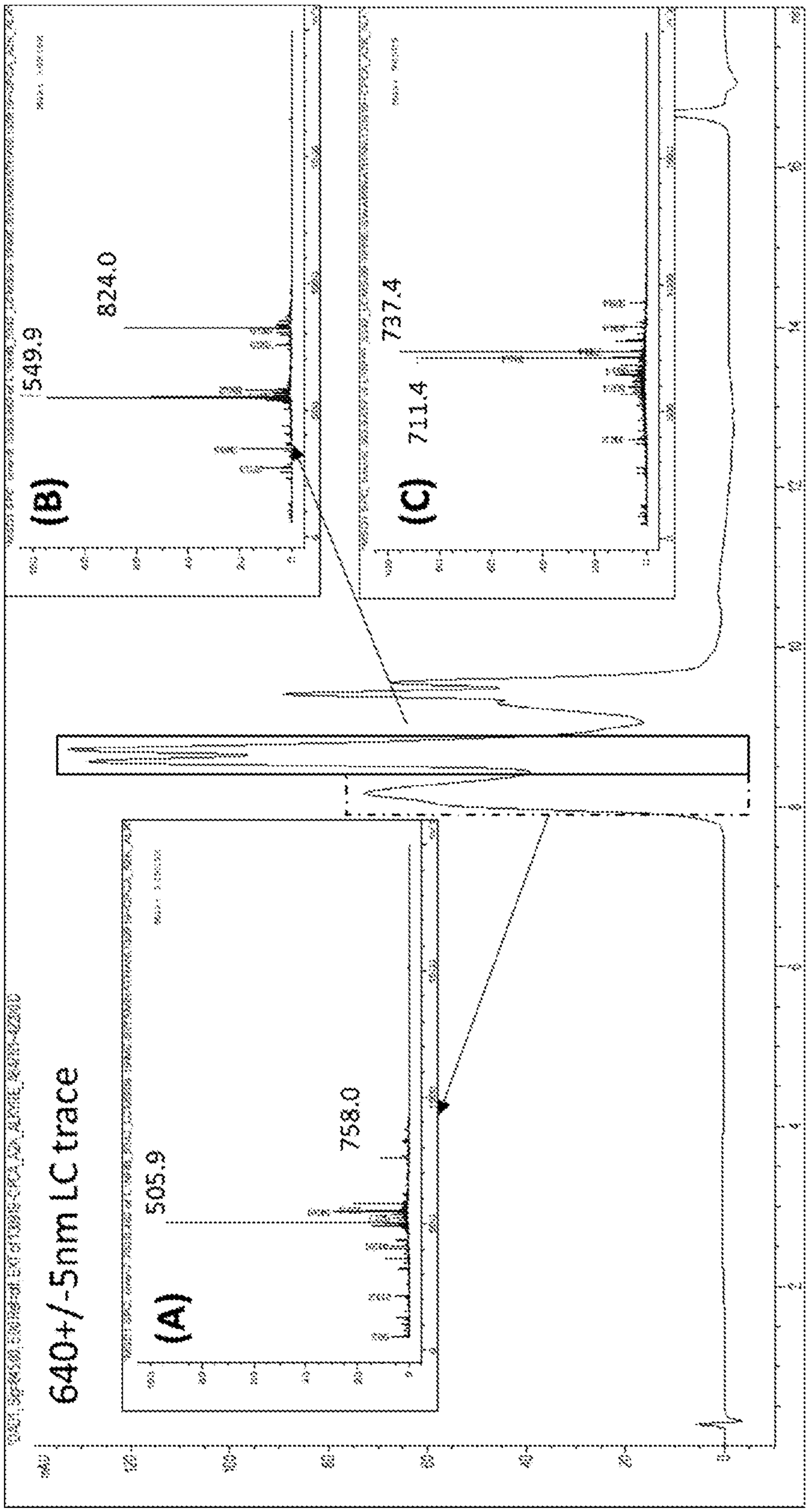
FIGS. 14A-C

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Ser Gly Lys Trp
1


<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Ala Lys Ala Gly Ala Gly Arg Tyr Gly
1               5


<210> SEQ ID NO 3
<211> LENGTH: 19
<212> TYPE: PRT
<213> ORGANISM: Artificial sequence
<220> FEATURE:
<223> OTHER INFORMATION: Synthetic peptide

<400> SEQUENCE: 3

Ala His Leu Ser Val Asp Ile Tyr Cys Asn Gly Phe Arg Thr Lys Trp
1               5                   10                  15

Glu Gln Met
```

SOLID-PHASE N-TERMINAL PEPTIDE CAPTURE AND RELEASE

This application is a national phase application under 35 U.S.C. § 371 of International Application No. PCT/US2019/054702, filed Oct. 4, 2019, which claims the benefit of priority to U.S. Provisional Applications, Ser. No. 62/741,833, filed Oct. 5, 2018, and Ser. No. 62/879,735, filed Jul. 29, 2019, the entire contents of each of which are incorporated herein by reference.

STATEMENT REGARDING FEDERALLY SPONSORED RESEARCH

This invention was made with government support under Grant no. R35 GM122480 awarded by the National Institutes of Health. The government has certain rights in the invention.

BACKGROUND

The chemical manipulation of proteins and peptides is a common process used to attach a variety of linkers, including isobaric moieties or isotopically labeled chemicals for comparative mass spectrometry studies (Weise et al., 2007), fluorescent chemicals that allow for quantitative measurement of binding constants (Andrews et al., 2008), and the installation of purification handles (Klement et al., 2010). For these experiments, the sample must be purified away from the remaining unreacted labels after each chemical manipulation in order to obtain reliable data. Common methods for purification include reverse-phase HPLC (RP-HPLC) and size-exclusion chromatography. However, every purification step can lead to an appreciable loss of sample, which in turn requires larger inputs of samples. To circumvent this problem, it is common for techniques to adopt a methodology that involves the use of solid supports, such as polystyrene resins. This movement from solution-phase to solid-phase has greatly advanced many fields, such as the chemical synthesis of peptides (Merrifield, 1963).

Due to the use of mass spectrometry and similar techniques in the diagnostics of diseases, the input samples are frequently derived from human tissue. Because of this, there is a limit as to what can be obtained, and loss of any sample can be extremely detrimental to the proper analysis. Due to the sample losses that occur during purification steps, such manipulation has limited the use of high-resolution mass spectrometry techniques, which could be used to personalize medicine for diseases. This is important to allow for clinicians to be able to accurately diagnose the exact type of cancer that a patient may have (Duffy et al., 2017). This is done by performing targeted mass spectrometry analysis of biopsies that look for specific biomarkers (e.g., proteins) that are mutated only in one disease state (Gnjatic et al., 2017). The presence and absence of these markers can allow physicians to differentiate cancer types, which can drastically alter the treatment prescribed (Mazzone et al., 2017).

Other related tools all require manipulation of peptides prior to capture, such as chemical reactions, which can remove peptide sequence manipulation for hydrazine capture resins or require the genetic manipulation of target peptides to install a purification handle. For at least the foregoing reasons, technologies that allow for the traceless, reversible, non-specific covalent attachment of native peptides are needed.

SUMMARY

The present disclosure relates to methods for reversibly capturing molecules, such as peptides, on a solid support to prepare the molecules for mass spectrometry, sequencing, single molecule protein sequencing and/or NMR analysis.

Provided herein are methods of molecule capture that can be performed using a solid support by the N-terminal covalent bonding of an aromatic or a heteroaromatic carboxaldehyde (e.g., 2-pyridinylcarboxaldehyde i.e. PCA), which, despite being covalent, is fully reversible under specific conditions. This solid support-bound molecule can be chemically and biologically modified while on the solid support and released when the molecule is prepared for analysis. The molecules can be proteins, peptides, or small molecules containing a 2-aminoacetamide. This method allows for rapid and high yield preparation for peptide/protein analysis techniques that require chemical manipulation.

In one aspect, the present disclosure provides compositions of:

(A) a solid support; and (B) a conjugating group of formula (I):

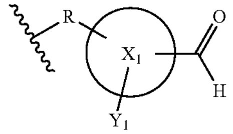

(I)

wherein:

$X_1$ is substituted or unsubstituted arenediyl$_{(C\leq 12)}$ or substituted or unsubstituted heteroarenediyl$_{(C\leq 12)}$;

$Y_1$ is hydrogen or an electron withdrawing group; and

R is a linker that is coupled to the solid support.

In one aspect, the present disclosure provides compositions of:

(A) a solid support; and (B) a conjugating group of the formula (Ia):

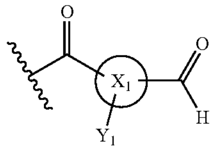

(Ia)

wherein:

$X_1$ is substituted or unsubstituted arenediyl$_{(C\leq 12)}$ or substituted or unsubstituted heteroarenediyl$_{(C\leq 12)}$;

$Y_1$ is hydrogen or an electron withdrawing group;

wherein the conjugating group is attached to the solid support at the open valence of the carbonyl group.

In some embodiments, $X_1$ is arenediyl$_{(C\leq 12)}$ or a substituted arenediyl$_{(C\leq 12)}$. In some embodiments, $X_1$ is arenediyl$_{(C\leq 12)}$, such as benzenediyl. In other embodiments, $X_1$ is a heteroarenediyl$_{(C\leq 12)}$ or a substituted heteroarenediyl$_{(C\leq 12)}$. In some embodiments, $X_1$ is heteroarenediyl$_{(C\leq 12)}$, such as pyridinediyl. In some embodiments, $Y_1$ is hydrogen. In other embodiments, $Y_1$ is an electron withdrawing group. In further embodiments, $Y_1$ is an electron withdrawing group selected from the group consisting of amino, cyano, halo, hydroxy, nitro, or a group of the formula: —$N(R_a)(R_b)(R_c)(R_d)^+$, wherein:

$R_a$, $R_b$, $R_c$, and $R_d$ are each hydrogen, $alkyl_{(C \leq 8)}$, or substituted $alkyl_{(C \leq 8)}$; or
$R_d$ is absent, provided that when $R_d$ is absent then the group is neutrally charged.
In some embodiments, the conjugating group comprises the group selected from:
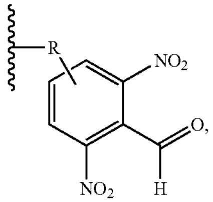
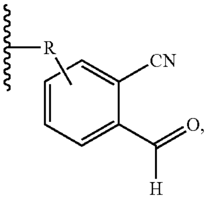
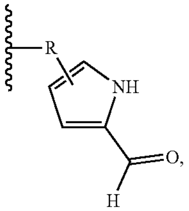
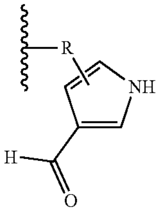
,
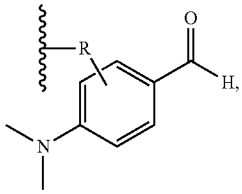
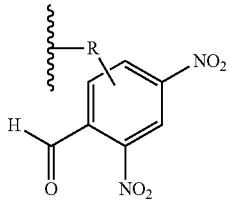
,
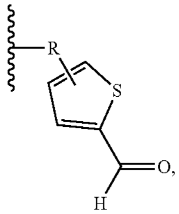
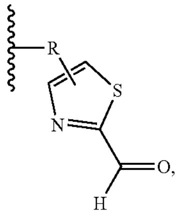
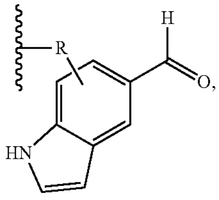
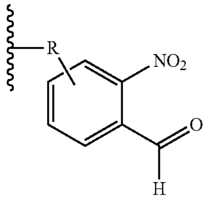
,
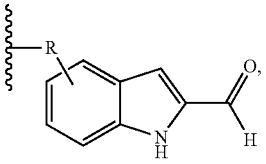
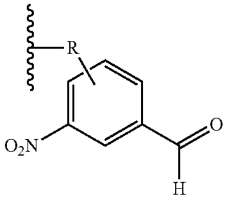
,
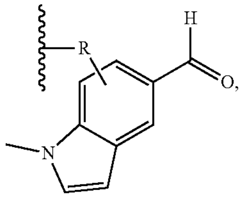
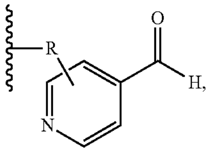
-continued
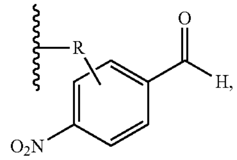
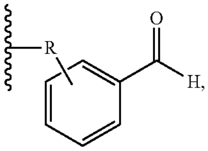
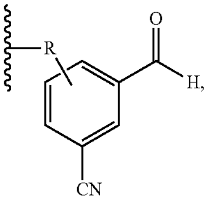
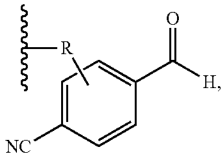
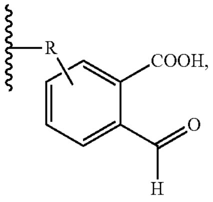
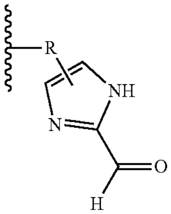
,
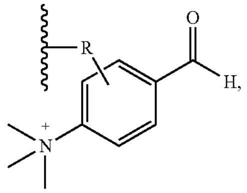
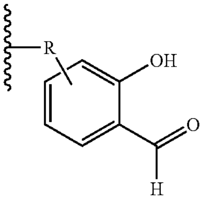
,
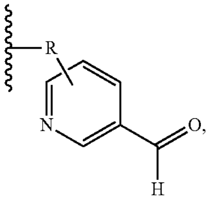
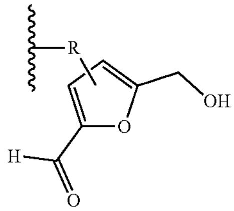
,
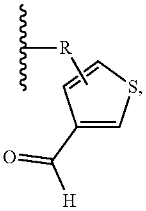
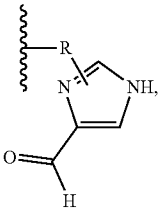
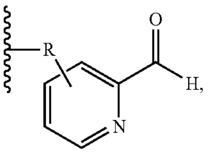
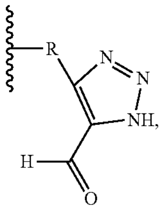
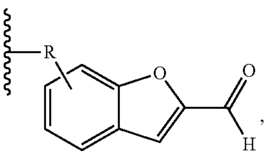
,
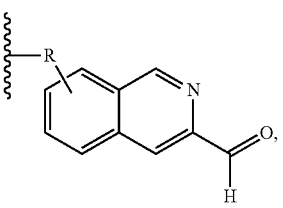
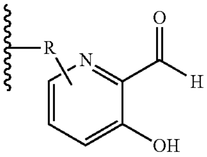
, and -continued

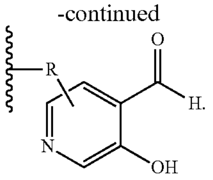

In some embodiments, the linker is a monomer or a polymer. In some embodiments, the linker comprises a polypeptide, a polyethylene glycol, a polyamide, a heterocycle, or any combination thereof. In some embodiments, the linker comprises at least one oxo.

In some embodiments, the conjugating group is further defined by:

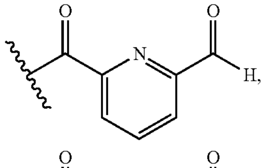
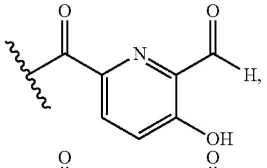
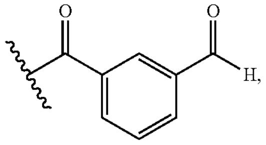
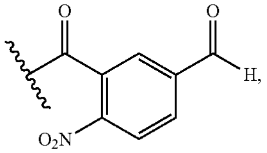
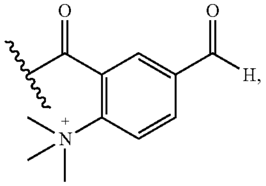
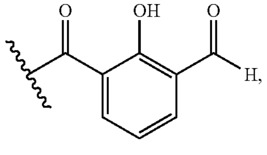
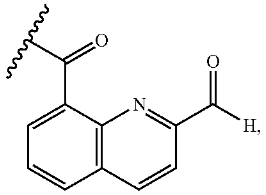
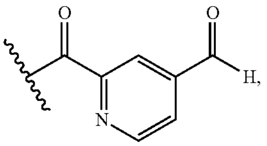
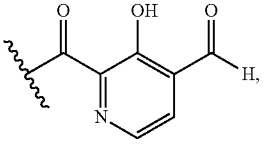
or
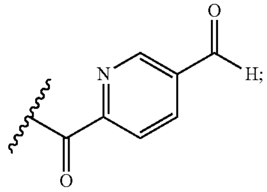

In some embodiments, the conjugating group is further defined by:

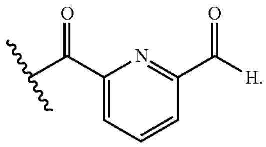

In some embodiments, the solid support comprises an amine group. In some embodiments, the solid support is a bead. In some embodiments, the bead is a polymer bead, such as a polystyrene bead. In some embodiments, the solid support comprises an iron oxide core. In some embodiments, the composition further comprises a metal salt, such as a copper salt, a magnesium salt, a calcium salt, or a manganese salt.

In another aspect, the present disclosure provides compositions comprising:

(A) a solid support; and (B) a conjugating group of the formula:

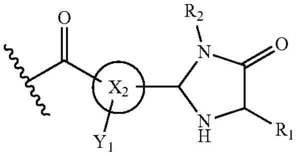

wherein:

$Y_1$ is hydrogen or an electron withdrawing group;

$X_2$ is arenediyl$_{(C\leq 12)}$, heteroarenediyl$_{(C\leq 12)}$, or a substituted version of either of these groups;

$R_1$ is the side chain of an amino acid residue;

$R_2$ is a peptide; and wherein the conjugating group is attached to the solid support at the open valence of the carbonyl group.

In some embodiments, $X_1$ is an arenediyl$_{(C\leq 12)}$ or a substituted arenediyl$_{(C\leq 12)}$. In some embodiments, $X_1$ is arenediyl$_{(C\leq 12)}$, such as benzenediyl. In other embodiments, $X_1$ is a heteroarenediyl$_{(C\leq 12)}$ or a substituted heteroarenediyl$_{(C\leq 12)}$. In some embodiments, $X_1$ is heteroarenediyl$_{(C\leq 12)}$, such as pyridinediyl. In some embodiments, $Y_1$ is hydrogen. In other embodiments, $Y_1$ is an electron withdrawing group. In further embodiments, $Y_1$ is an electron withdrawing group selected from the group consisting of amino, cyano, halo, hydroxy, nitro, or a group of the formula: —$N(R_a)(R_b)(R_c)(R_d)^+$, wherein:

$R_a$, $R_b$, $R_c$, and $R_d$ are each hydrogen, alkyl$_{(C\leq 8)}$, or substituted alkyl$_{(C\leq 8)}$; or $R_d$ is absent, provided that when $R_d$ is absent then the group is neutrally charged.

In some embodiments, the conjugating group is further defined by the formula:

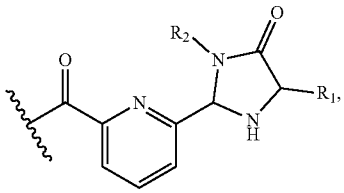
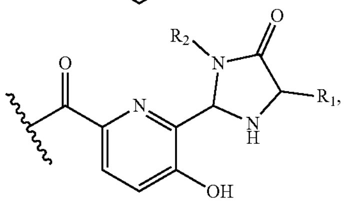
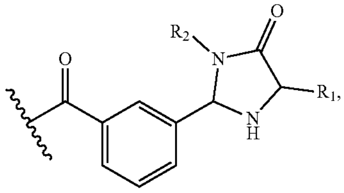

-continued

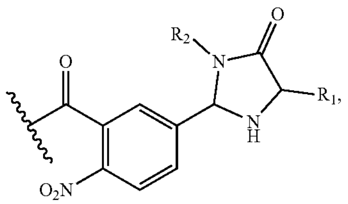

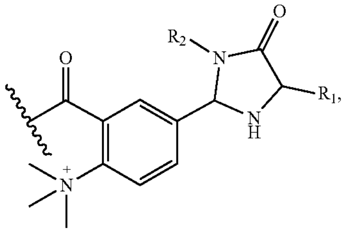

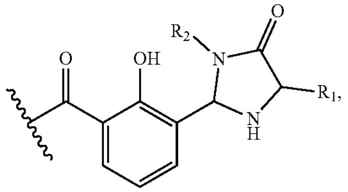

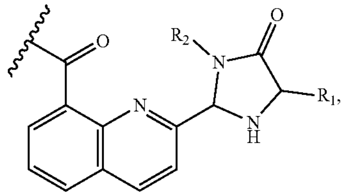

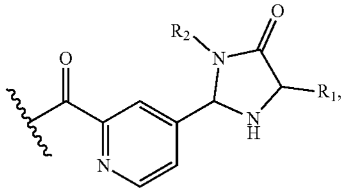

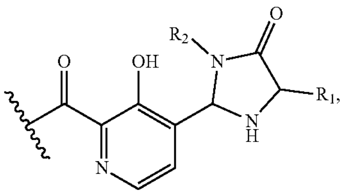

or

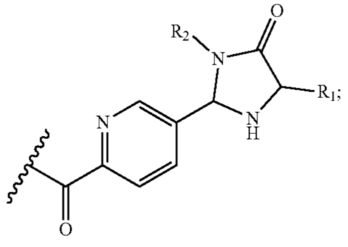

In some embodiments, the conjugating group is further defined by the formula:

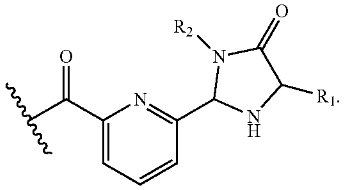

In some embodiments, $R_1$ is alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups. In some embodiments, $R_1$ is alkyl$_{(C\leq12)}$, aryl$_{(C\leq12)}$, aralkyl$_{(C\leq12)}$, heteroaralkyl$_{(C\leq12)}$, or a substituted version of any of these groups. In some embodiments, $R_1$ is the side chain of a canonical amino acid. In some embodiments, $R_2$ is a peptide comprises from 1 to 250 amino acid residues. In further embodiments, $R_2$ is a peptide comprising from 3 to 25 amino acid residues. In still further embodiments, $R_2$ is a peptide comprising from 5 to 14 amino acid residues. In some embodiments, the peptide is from a cell lysate. In other embodiments, the peptide is from a protein mixture. In other embodiments, the peptide is obtained from a digested protein mixture. In other embodiments, the peptide is a polypeptide and considered as a whole protein. In still other embodiments, the peptide is from an intact cell. In yet other embodiments, the peptide is from solid phase synthesis. In other embodiments, the peptide is from the extracellular space. In still other embodiments, the peptide is from a biological sample, such as blood, lymphatic fluid, saliva, or urine.

In some embodiments, the solid support comprises an amine group, an alcohol group, a halide group, or a carboxylic acid group. In some embodiments, the solid support comprises an amine group. In some embodiments, the solid support is a bead. In further embodiments, the bead is a polymer bead, such as a polystyrene bead. In some embodiments, the solid support comprises an iron oxide core. In some embodiments, the composition further comprises a metal salt, such as a copper salt, a magnesium salt, a calcium salt, or a manganese salt.

In still another aspect, the present disclosure provides methods of reversibly immobilizing a polyamide polymer comprising reacting a terminal amine of a polyamide polymer with a composition the present disclosure to form an immobilized polyamide polymer.

In some embodiments, the polyamide polymer comprises an amino acid or amide group backbone with regular spacing. In some embodiments, the polyamide polymer is an aminomethyl pyrrolidine. In other embodiments, the polyamide polymer is a peptide or a protein. In some embodiments, the peptide comprises from 2 to 250 amino acid residues. In further embodiments, the peptide comprising from 4 to 25 amino acid residues. In still further embodiments, $R_2$ is a peptide comprising from 6 to 14 amino acid residues. In some embodiments, the composition comprises a solid support that is a bead, such as a polystyrene bead. In some embodiments, the bead comprises an iron oxide core. In some embodiments, the composition comprises a conjugating group wherein $X_1$ is an arenediyl$_{(C\leq12)}$ or a substituted arenediyl$_{(C\leq12)}$. In some embodiments, $X_1$ is arenediyl$_{(C\leq12)}$, such as benzenediyl. In some embodiments, the composition comprises a conjugating group wherein $X_1$ is a heteroarenediyl$_{(C\leq12)}$ or a substituted heteroarenediyl$_{(C\leq12)}$. In some embodiments, $X_1$ is heteroarenediyl$_{(C\leq12)}$, such as pyridinediyl.

In some embodiments, the methods further comprise reacting the polyamide polymer and the composition in a solution. In some embodiments, the solution is an aqueous solution. In other embodiments, the solution is a buffered solution. In some embodiments, the solution is a buffered aqueous solution. In some embodiments, the solution is a phosphate buffered saline solution. In some embodiments, the solution has a pH from about 6.5-8.5. In further embodiments, the pH of the solution is from about 7.2-7.8. In some embodiments, the reaction of the polyamide polymer and the composition is carried out at a temperature from about 20° C. to about 100° C. In further embodiments, the temperature is from about 30° C. to about 70° C., such as about 37° C. In some embodiments, the method further comprises a catalyst. In some embodiments, the catalyst is a substituted or unsubstituted C1-C12 aryl amine. In some embodiments, the catalyst is an aniline. In other embodiments, the catalyst is a substituted version of aniline, such as 5-methoxyaniline, phenylenediamine, or aminobenzoic acid. In still other embodiments, the catalyst is a C1-C12 amino substituted alkane. In some embodiments, the amino that has been substituted on the alkane may be an amino, a C1-C6 alkylamino, or a C2-C12 dialkylamino.

In some embodiments, the methods further comprise adding a reversing agent to the immobilized polyamide polymer. In some embodiments, the reversing agent is added to the immobilized polyamide polymer in solution. In some embodiments, the reversing agent is a hydrazine, an oxime, methoxylamine, ammonia, or aniline. In some embodiments, the reversing agent removes the PCA group from the solution. In some embodiments, method comprises adding a ratio of the reversing agent to the immobilized polyamide polymer from about 10:1 to about 100,000:1. In further embodiments, the ratio is from about 100:1 to about 10,000:1. In still further embodiments, the ratio is about 1000:1. In some embodiments, the methods further comprise reacting the immobilized polyamide polymer and the reversing agent in a reversing solution. In some embodiments, the reversing solution is an aqueous solution. In other embodiments, the reversing solution is a buffered solution. In some embodiments, the reversing solution is a buffered aqueous solution, such as a phosphate buffered saline solution. In some embodiments, the reversing solution has a pH from about 6.5-8.5. In further embodiments, the pH of the reversing solution is from about 7.2-7.8. In some embodiments, the reaction of the immobilized polyamide polymer and the reversing agent is carried out at a temperature from about 20° C. to about 100° C. In further embodiments, the temperature is from about 30° C. to about 70° C., such as about 37° C. In some embodiments, the method is automated. In further embodiments, the method is carried out in an apparatus capable of admixing and removing the polyamide polymer, the composition, and the removing agent at an appropriate time.

In yet another aspect, the present disclosure provides methods of enriching one or more peptides with an N-terminus comprising:

(A) immobilizing the peptides with the composition of the present disclosure to form an immobilized peptide;
(B) washing the immobilized peptide with a washing solution thereby removing the non-peptide materials to form an enriched solution;
(C) removing the immobilized peptide with a reversing agent to form an enriched peptide.

In some embodiments, the method further comprises reacting the peptides with an enzyme before or after immobilization.

In another aspect, the present disclosure provides methods of enriching one or more peptide with an N-terminus comprising:

(A) immobilizing the peptides with the composition of the present disclosure to form an immobilized peptide;
(B) reacting the immobilized peptide with an enzyme which cleaves one or more peptide bonds to form a cleaved solution; and
(C) reacting the cleaved solution with the composition a second time to form an enriched solution.

In some embodiments, the enzyme is a protease. In some embodiments, the method further comprises removing the immobilized peptides in the enrichment solution by adding a removing agent.

In still another aspect, the present disclosure provides methods of modifying a peptide comprising:

(A) immobilizing the peptides with the composition of the present disclosure to form an immobilized peptide;
(B) reacting the immobilized peptide to a modifying group to form a modified peptide.

In some embodiments, the modifying group is a label, such as a fluorophore. In other embodiments, the modifying group is an enzyme which modifies the peptide. In some embodiments, the enzyme introduces a modification at the C terminus. In other embodiments, the enzyme introduces a modification to an amino acid residue in the peptide. In further embodiments, the enzyme introduces a post-translational modification.

In yet another aspect, the present disclosure provides methods of selectively labeling amine containing amino acid residues in a peptide comprising:

(A) reacting the peptides with a composition of the present disclosure to form a blocked peptide; and
(B) reacting the amine containing amino acid residues with a modifying reagent to form an amino labeled peptide.

In some embodiments, the modifying group is a label, such as a fluorophore. In some embodiments, the method further comprises reacting the amino labeled peptide with a removing agent to form a free amino labeled peptide. In some embodiments, the peptide is from a cell lysate. In other embodiments, the peptide is from a protein mixture. In still other embodiments, the peptide is from an intact cell. In yet other embodiments, the peptide is from solid phase synthesis. In other embodiments, the peptide is from the extracellular space. In still other embodiments, the peptide or protein is from a biological sample. In some embodiments, the peptide or protein is simultaneously digested and captured. In some embodiments, the biological sample is blood, lymphatic fluid, saliva, or urine. In some embodiments, the peptide is present in the sample at an amount of less than 10 nanomoles. In further embodiments, the amount is less than 1 nanomoles. In still further embodiments, the amount is less than 10 picomoles. In yet further embodiments, the amount is less than 1 picomoles. In some embodiments, the peptide is for use in a mass spectroscopy study. In other embodiments, the peptide is for use in fluorosequencing.

In certain aspects, the disclosure provides a method processing or analyzing a protein or peptide, comprising: (A) providing a support and a mixture comprising a cell, wherein said support has coupled thereto (i) a barcode, and (ii) a capture moiety for capturing said protein or peptide of said cell; (B) using said capture moiety to capture said protein or peptide of said cell; and (C) subsequent to (B), (i) identifying said barcode and associating said barcode with said cell, (ii) sequencing said protein or peptide to identify said protein or peptide, or a sequence thereof; and (iii) using said barcode identified in (i) and said protein or peptide, or sequence thereof identified in (ii) to identify said protein or peptide, or sequence thereof as having originated from said cell.

In certain aspects, the disclosure provides a method of processing or analyzing a protein or peptide, comprising: (a) providing a support and a mixture comprising a cell, wherein said support has coupled thereto (i) a nucleic acid barcode sequence, and (ii) said capture moiety for capturing a protein or peptide of said cell; (b) using said capture moiety to capture said protein or peptide of said cell; and (c) subsequent to (b), (i) identifying said nucleic acid barcode sequence and associating said nucleic acid barcode sequence with said cell, (ii) sequencing said protein or peptide to identify said protein or peptide, or a sequence thereof; and (iii) using said barcode sequence identified in (i) and said protein or peptide, or sequence thereof identified in (ii) to identify said protein or peptide, or sequence thereof as having originated from said cell.

In some embodiments, the nucleic acid barcode sequence is coupled to said support through a linker. In some embodiments, the nucleic acid barcode sequence is directly coupled to said support.

In some embodiments, the mixture comprises a plurality of cells, which plurality of cells comprises said cell. In some embodiments, (a) comprises providing a plurality of supports, which plurality of supports comprises said support. In some embodiments, (a) comprises providing a plurality of supports and said mixture comprising a plurality of cells, which plurality of supports comprises said support and said plurality of cells comprises said cell.

In some embodiments, the cells are isolated from a biological sample. In some embodiments, the said biological sample is derived from tissue, blood, urine, saliva, lymphatic fluid, or any combination thereof.

In some embodiments, the support is a solid or semi-solid support. In some embodiments, the support is a bead. In some embodiments, the bead is a gel bead. In some embodiments, the support is a resin.

In some embodiments, the support comprises a pendant group comprising said capture moiety. In some embodiments, the pendant group further comprises a cleavable unit. In some embodiments, the cleavable unit is coupled between said support and said capture moiety. In some embodiments, the pendant group comprises said nucleic acid barcode sequence. In some embodiments, further comprising an additional capture moiety coupled to said support. In some embodiments, the said additional capture moiety is configured to capture a ribonucleic acid (RNA) molecule from said cell. In some embodiments, the support contains a plurality of pendant groups. In some embodiments, the pendant groups of said plurality of pendant groups are identical.

In some embodiments, the nucleic acid barcode sequence is deoxyribonucleic acid (DNA), ribonucleic acid (RNA), a peptide nucleic acid (PNA), or any combination thereof. In some embodiments, the nucleic acid barcode sequence is an oligomer. In some embodiments, the oligomer has a length of at least 10 nucleic acid bases. In some embodiments, the length is at least 100 nucleic acid bases.

In some embodiments, the support comprises a plurality of nucleic acid barcode sequences, which plurality of nucleic acid barcode sequences comprises said nucleic acid barcode sequence. In some embodiments, the plurality of nucleic acid barcode sequences have barcode sequences that are identical.

In some embodiments, the nucleic acid barcode sequence is identified with a probe that interacts with said nucleic acid barcode sequence to yield a signal or change thereof that is detected. In some embodiments, the probe hybridizes to said nucleic acid barcode sequence. In some embodiments, the signal is an optical signal. In some embodiments, the optical signal is a fluorescent signal. In some embodiments, the probe comprises one of an energy donor and an energy acceptor, wherein said nucleic acid barcode sequence is coupled to the other of said energy donor and said energy acceptor, and wherein said optical signal is generated by fluorescence resonance energy transfer (FRET). In some embodiments, the optical signal is a bioluminescent signal. In some embodiments, the probe comprises one of an energy donor and an energy acceptor, wherein said nucleic acid barcode sequence is coupled to the other of said energy donor and said energy acceptor, and wherein said optical signal is generated by bioluminescence resonance energy transfer (BRET). In some embodiments, the optical signal is an electrochemiluminescent signal. In some embodiments, the probe comprises one of an energy donor and an energy acceptor, wherein said nucleic acid barcode sequence is coupled to the other of said energy donor and said energy acceptor, and wherein said optical signal is generated by electrochemiluminescent resonance energy transfer (ECRET). In some embodiments, the probe comprises one of an emitter and a quencher, wherein said nucleic acid barcode sequence is coupled to the other of said emitter and said quencher, and wherein said nucleic acid barcode sequence is identified upon a quenching of said optical signal. In some embodiments, the nucleic acid barcode sequence is identified with nanopore sequencing. In some embodiments, the nucleic acid barcode sequence and protein sequence are identified by nanopore sequencing.

In some embodiments, (c) comprises providing said protein or peptide adjacent to an array, and sequencing said protein or peptide adjacent to said array. In some embodiments, prior to said sequencing, said protein or peptide having coupled thereto said nucleic acid barcode sequence is (a) provided adjacent to an array, (b) identified, and (c) removed from said protein or peptide. In some embodiments, prior to (a), said peptide or protein is labeled with at least one label. In some embodiments, the labels are optical labels. In some embodiments, the optical labels are fluorophores. In some embodiments, the fluorophores couple to select amino acids of said peptide or protein. In some embodiments, the optical labels are used for fluorosequencing said peptide or protein. In some embodiments, the nucleic acid barcode sequence is removed from said protein or peptide by cleaving said capture moiety, thereby producing said protein or peptide to be identified. In some embodiments, the capture moiety is cleaved by a reversing reagent. In some embodiments, the reversing reagent is a hydrazine, an oxime, a methoxylamine, ammonia, or an aniline. In some embodiments, the reversing reagent is said hydrazine.

In some embodiments, the sequencing of said protein or peptide is performed using Edman degradation. In some embodiments, the sequencing said protein or peptide comprises (i) labeling at least a subset of amino acid residues of said protein or peptide with labels, and (ii) sequentially detecting said labels to identify said protein or peptide, or sequence thereof. In some embodiments, the labels are optical labels. In some embodiments, the optical labels are fluorophores. In some embodiments, the optical labels are used for fluorosequencing said peptide or protein. In some embodiments, the prior to (ii), said peptide or protein having said labels is removed or released from said support by cleaving said cleavable group. In some embodiments, the subsequent to removing or releasing said protein or peptide from said support, a location of said protein or peptide adjacent to an array is identified.

In some embodiments, the (a) comprises providing a droplet among a plurality of droplets, which droplet comprises said mixture. In some embodiments, the mixture comprises no more than said cell. In some embodiments, the cell is lysed, thereby forming a lysed cell, wherein said lysed cell releases or makes accessible a plurality of proteins or peptides of said cell, which plurality of proteins or peptides comprises said protein or peptide. In some embodiments, the plurality of proteins or peptides of said cell are digested, thereby forming another plurality of proteins or peptides. In some embodiments, the plurality of proteins or peptides are captured by a plurality of capture moieties coupled to said support. In some embodiments, the (a) comprises providing a well among a plurality of wells, which well comprises said mixture. In some embodiments, the support comprises a pendant group comprising said capture moiety, and wherein said pendant group and said nucleic acid barcode sequence are separately coupled to said support.

In certain aspects, the disclosure provides a composition comprising a support having coupled thereto (i) a nucleic acid barcode sequence and (ii) a capture moiety for capturing a protein or peptide, wherein said capture moiety is not an antibody.

In certain aspects, the disclosure provides a composition comprising a support having coupled thereto (i) a nucleic acid barcode sequence and (ii) a capture moiety comprising an aromatic or a heteroaromatic carboxaldehyde. In certain aspects, the disclosure provides a composition comprising a support having coupled thereto (i) a nucleic acid barcode sequence and (ii) a capture moiety comprising 2-pyridinecarboxaldehyde or a derivative thereof.

In certain aspects, the disclosure provides a method of performing spatial proteomics comprising: introducing a plurality of supports to a tissue comprising a plurality of proteins or peptides, wherein a single support of said plurality of supports contacts an area of said tissue, wherein said single support of said plurality of supports comprises a unique barcode and a capture moiety; using said capture moiety to capture a protein or peptide of said plurality of proteins or peptides; using said unique barcode to identify a location of said tissue from which said protein or peptide was derived; determining a sequence of said protein or peptide; and associating said location identified in (c) with said sequence determined in (d). In some embodiments, the tissue is from a biological sample. In some embodiments, the tissue comprises a plurality of cells.

In certain aspects, the disclosure provides a method of storing or stabilizing a plurality of peptides, proteins, or combinations thereof, comprising using a plurality of supports comprising a plurality of capture moieties to capture said peptides, proteins, or combinations thereof, wherein a capture moiety of said plurality of capture moieties (i) is not an antibody or (ii) comprises an aromatic or a heteroaromatic carboxaldehyde. In certain aspects, the disclosure provides a method of storing or stabilizing a plurality of peptides, proteins, or combinations thereof, comprising using a plurality of supports comprising a plurality of capture moieties to capture said peptides, proteins, or combinations thereof, wherein a capture moiety of said plurality of capture moieties (i) is not an antibody or (ii) comprises 2-pyridinecarboxaldehyde or a derivative thereof. In some embodiments, a support of said plurality of supports comprises a unique nucleic acid barcode sequence. In some embodiments, the method further comprises storing said plurality of peptides, proteins, or combinations thereof captured with said plurality of capture moieties. In some embodiments, the method further comprises washing said plurality of peptides, proteins, or combinations thereof captured with said plurality of capture moieties, thereby removing uncaptured molecules.

In certain aspects, the disclosure provides a method for generating a nucleic acid barcode sequence coupled to a support, comprising: providing said support having coupled thereto a capture moiety configured to capture a protein or peptide and a nucleic acid segment; and combinatorially assembling said nucleic acid barcode sequence to said nucleic acid segment. In some embodiments, the combinatorially assembling comprises subjecting said nucleic acid segment or derivative thereof to one or more split-pool cycles. In some embodiments, the support comprises a pendant group comprising said capture moiety. In some embodiments, the pendant group further comprises a cleavable unit. In some embodiments, the support contains a plurality of pendant groups. In some embodiments, each pendant group of said plurality of pendant groups is identical. In some embodiments, the plurality of pendant groups comprises at least $10^5$ identical pendant groups. In some embodiments, the plurality of pendant groups comprises at least $10^{10}$ identical pendant groups. In some embodiments, the plurality of pendant groups comprises at least $10^{12}$ identical pendant groups. In some embodiments, the plurality of pendant groups comprises at least $10^{15}$ identical pendant groups.

In some embodiments, the support is coupled to a first position of said cleavable unit and said capture moiety is coupled to a second position of said cleavable unit. In some embodiments, the nucleic acid barcode sequence is coupled to said support. In some embodiments, the nucleic acid barcode sequence is assembled using a split and pool technique. In some embodiments, the split and pool technique provides a support with a unique barcode sequence. In some embodiments, the capture moiety comprises formula (I):

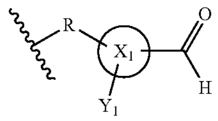

wherein: $X_1$ is substituted or unsubstituted arenediyl$_{(C\leq12)}$ or substituted or unsubstituted heteroarenediyl$_{(C\leq12)}$; $Y_1$ is hydrogen or an electron withdrawing group; and R is a linker that is coupled to the solid support. In some embodiments, the capture moiety comprises formula (Ia):

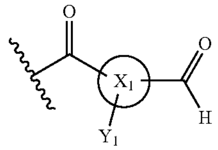

wherein: $X_1$ is substituted or unsubstituted arenediyl$_{(C\leq12)}$ substituted or unsubstituted heteroarenediyl$_{(C\leq12)}$; $Y_1$ is hydrogen or an electron withdrawing group; wherein said capture moiety is attached to said cleavable unit at the open valence of the carbonyl group.

In some embodiments, the support comprises a pendant group comprising said nucleic acid barcode sequence coupled adjacent to said capture moiety. In some embodiments, the pendant group further comprises a cleavable unit. In some embodiments, the support is coupled to a plurality of pendant groups. In some embodiments, each pendant group of said plurality of pendant groups is identical. In some embodiments, the plurality of pendant groups comprises at least identical $10^5$ pendant groups. In some embodiments, the plurality of pendant groups comprises at least identical $10^{10}$ pendant groups. In some embodiments, the plurality of pendant groups comprises at least identical $10^{12}$ pendant groups. In some embodiments, the plurality of pendant groups comprises at least identical $10^{15}$ pendant groups. In some embodiments, the support is coupled to said cleavable unit, wherein said cleavable unit is coupled to a building block for barcoding, wherein said building block for barcoding is coupled to said capture moiety. In some embodiments, the method further comprises (a) said support is coupled to a first position of said cleavable unit, (b) a first position of said building block for barcoding is coupled to a second position of said cleavable unit, (c) said capture moiety is coupled to a second position of said building block for barcoding, and (d) said nucleic acid barcode sequence is coupled to a third position of said building block for barcoding. In some embodiments, the nucleic acid barcode sequence is assembled using a split and pool technique. In some embodiments, the split and pool technique provides a support wherein each pendant group coupled to said support has a unique barcode sequence associated with said support.

In some embodiments, the capture moiety comprises formula (I):

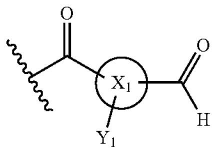

wherein: $X_1$ is arenediyl$_{(C\leq12)}$, heteroarenediyl$_{(C\leq12)}$, or a substituted version of either of these groups; $Y_1$ is hydrogen or an electron withdrawing group; wherein said capture moiety is attached to said cleavable unit at the open valence of the carbonyl group. In some embodiments, each peptide or protein of said cell is captured by said plurality of capture moieties.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10A-10C. Illustration of reversal tests for N-terminally imidazolinone capped SGW peptide with various imidazolinones.

FIG. 12A-12C. A schematic and representative results of a PEG-Rink-FPCA resin and the steps for coupling and releasing peptides.

FIG. 13A-13C. A representation of a one-pot proteome digestion and solid-phase capture strategy.

FIG. 14A-14C. A depiction of multiple derivatizations on resin-captured peptide.

DETAILED DESCRIPTION

Figure 1:
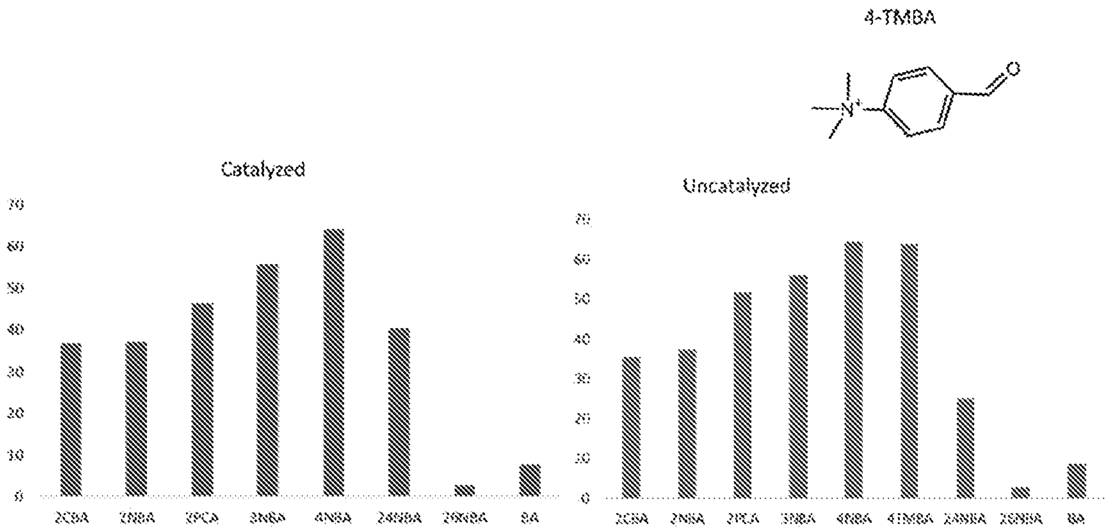
FIG. 1. Screen of benzaldehyde derivatives. Compounds screened were benzaldehyde, pyridinyl carboxaldehyde, 2-nitrobenzaldehyde, 3-nitrobenazldehyde, 4-nitrobenzaldehyde, 2,4-dinitrobenzaldehyde, 2,6-dinitrobenzaldehyde, 4-trimethylaminobenzaldehyde, and 2-cyanobenzaldehyde. Peptide was present at a concentration of 0.1 mM; aldehyde was present at a concentration of 0.3 mM; catalyst was present at a concentration of 1 mM.

In order to process peptides or proteins for analytical methods, such as mass spectrometry, the samples must first be chemically modified or isolated. In another embodiment, even without chemical additions, proteins and peptides must be purified to remove cell debris and/or digestion enzymes. For example, current technologies, such as streptavidin-biotin purification and hydrazine capture resins, which require the installation of a formyl group on the peptides to be captured. However, these processes often require one or more purification processes, which reduce the overall yield of the samples to be analyzed.

With the increasing sensitivity of proteomics methods, a number of new proteins, protein isoforms, and post-translational modifications have been discovered (Hwang et al., 2018; Schwammle et al., 2014). The increase in sensitivity is due to an increase in both improvements to the mass-spectrometer itself, as well as the ability to generate high quality protein/peptide samples that are often highly derivatized (Lin and Garcia, 2012). These methods however often utilize purification techniques that are prone to sample losses, and the inclusion of multiple derivatization/purification cycles can lead to low abundance peptides dropping below the detection thresholds (Lee, 2017). This can lead to a bias against rare or low abundance peptides that may be biologically important, but due to the purification steps drop below the detection threshold (Steen et al., 2006).

The manner that peptides from biological materials are prepared for mass spectrometry analysis is an important consideration in proteomic studies. For example, in bottom-up proteomics, the mode of digestion of proteins is a critical decision. It is routinely done either in-solution, where proteases are added to the proteins directly, or the protease treatment is done to specific gel locations after an initial 1D or 2D polyacrylamide electrophoresis separation. After digestion, the sample is derivatized for several purposes: to eliminate unwanted side products such as disulfides (Baez, et al., 2015), introduce isotopic labels for quantitation (Wiese et al., 2007), or to aid ionization (Waliczek et al., 2016), and add handles that can be cleaved to induce specific cleavage patterns (Quick et al., 2017). With each of these protocols the preparation requires that the sample be purified to separate the peptides from any side-products or unreacted chemicals.

One method that we envisioned could be used to improve sample preparation is to bind the proteins/peptides to a bead or other solid matrix. While this has been attempted before, such immobilization generally relies on either the addition of non-natural amino acids as purification handles (Lang and Chin, 2014) or relies on non-covalent bonding such as nickel affinity chromatography or non-specific precipitation. These properties make them unattractive for studies that are derived from mammalian cultures due to the difficulty with installing non-natural amino acids via amber codon suppression in mammalian cell cultures (Lin et al., 2017), or because of the limitations in solvent/buffer conditions that are compatible with immobilized metal affinity chromatography (Dunn et al., 2009).

A method that allows for the binding of peptides resin support in a covalent manner and reversible manner would enable complex manipulations with higher overall yields. It would allow for the identification, derivatization, and purification of peptides, including important low abundance peptides. Importantly, such a procedure would allow for derivatization schemes that could otherwise never be utilized due to difficulties with chromatographic separations. For example, a capture and release facilities derivatization because the use of excess reagents and washing steps are possible, analogous to peptide synthesis on resin, where experimental procedures are optimized to impart high yield and speed (Merrifield, 1963).

Provided herein are methods of using aromatic or heteroaromic carboxaldehydes (e.g., 2-pyridinecarboxalehyde (PCA)) attached to a solid support, such as, for example, a polystyrene or iron-core resin, for the non-specific purification of peptides, proteins, or other molecules containing a 2-aminoacetamide. Due to the nature of the interaction, the solid support may interact with any or peptides that are incubated with it, allowing for the nondiscriminatory binding of molecules to the support. As peptides can be bound to the capture resin in the early stage of preparation, very low concentrations of sample can be handled without the concern for excessive sample loss due to adsorption to reaction vessels.

The captured molecules can be manipulated, such as, for example, through the use of organic and aqueous solvents, reagents, or enzymes to perform chemistry on the captured molecules. Once a peptide or protein is reversibly attached to a solid support, it can be labeled with a number of chemicals, including fluorescent markers, quencher molecules, biotin, and polymers, including PEG linkers and/or oligonucleotides. These reactions can be performed consecutively with only washing steps in between cycles. Through these steps, molecules can be differentiated from each other without the need for multiple purifications.

After all handling and manipulation steps are complete, the covalent attachment can be released without leaving a trace from the solid support allowing for liberation of the molecules back into solution. Following release, the molecules can be analyzed using mass spectrometry, sequencing, and/or NMR technology. The samples can also be released from the capture resin, and maintain the N-terminal protection if required, and can then be reversed in solution if required.

Once the peptides are bound to the capture resin, it is possible to transfer the sample into an automated liquid handling system. This can then be programmed to perform any number of chemical steps in a wide variety of solvents. It also allows for the utilization of microwave-assisted chemistry, to allow for more rapid reactions to occur. This can also allow for multiple reactions to be run in parallel and decreases the amount of intrinsic knowledge required to perform many important steps for this method.

The present methods can also be used to immobilize small molecules that contain the requisite 2-aminoacetamide such that they can be manipulated on a solid support, and the reactive amine group can be protected during these reactions. Peptides can also be generated and bound to the resin in situ when proteins are digested by proteases while being incubated with the immobilization regent, and afterwards the protease can be removed from the peptide mixture during the routine wash steps.

I. PROTEOMIC METHODS

There exist many methods of identifying the sequence of a peptide, including fluorosequencing, mass spectroscopy, identifying the peptide sequence from the nucleic acid sequence, and Edman degradation.

A. Mass Spectrometry

Mass spectrometry (MS) is an analytical technique that determines the mass of atoms or molecules by means of ion-field (electric or magnetic) interactions. A mass spectrometer consists of three fundamental components: An ionization source, where gas-phase ions are generated; a mass analyzer, where ions of different mass-to-charge ratios (m/z) are separated; and a detector, where the separated ions produce detectable signals.

Over the last several decades, the twin techniques of Matrix-Assisted Laser Desorption/Ionization (MALDI) and Electrospray Ionization (ESI) Mass Spectrometry (MS) were developed. The two techniques differ significantly but are both highly effective in the production of intact, gas-phase, large biomolecule ions. Producing these ions is a required first step for mass spectrometric analysis.

The success of MALDI is based on the use of a matrix compound that absorbs laser irradiation at a wavelength where the analytes do not. In this technique, the analyte is co-crystallized with a small organic compound. Upon excitation by a laser pulse with sufficient energy density, a sudden and explosive phase transition occurs. From among all the analyte molecules desorbed from the matrix, only a small portion ($^{-}10^{4}$) are ionized. Although the mechanism of ion formation in MALDI remains in debate, gas-phase proton transfer is generally believed to be involved in this process. Ions produced in MALDI are usually singly-charged, making MALDI amenable to mixture analysis. Furthermore, the time-of flight (TOF) mass analyzer to which MALDI is most often coupled is robust, simple, sensitive, and capable of detecting proteins as large as 100,000 mass units (amu). Both methods are now established as state-of-the-art analytical tools in proteomics, finding applications in protein identification by mass mapping, and single peptide fragmentation, as well as the identification and characterization of post-translation modifications, such as protein phosphorylation. Perhaps the most popular of these applications is protein identification by mass mapping, in which proteins, once separated by 2-DE or HPLC, are digested by a sequence-specific proteolytic enzyme such as trypsin. Upon digestion by such an enzyme, a specific protein will produce a unique set of polypeptide sequences, which upon detection and analysis by MS, yields a polypeptide mass-map. This mass-map, which is unique, can be used to identify the protein. Mass spectrometry is also used for protein sequencing, replacing Edman sequencing. Mass spectrometry allows for the analysis of sub-femtomole quantities and is not restricted by N-terminal modifications, both problems associated with the Edman-based method.

Electrospray ionization results in a distribution of multiply-charged ions for each analyte present. The basic ESI source consists of a metal needle maintained at high voltage (˜4 kV). The needle is positioned in front of a counter-electrode held at ground or low potential (and which also doubles as the inlet of the mass spectrometer). Sample solution is gently pumped through the needle and is transformed into a mist of micrometer-sized droplets that fly rapidly toward the counter electrode. In addition to the applied voltage, a concentric flow of nitrogen is often used to help nebulize the solution and dissolve the analyte ions. As each droplet decreases in size, the field density on its surface increases. When charge repulsion exceeds the force of surface tension, the parent droplet splits into smaller daughter droplets. This droplet fission continues until naked ions are formed.

MALDI and ESI have been coupled to many different mass analyzer types. The two most common are the Time of Flight (TOF) and the Triple Quadrupole (QqQ). Time-of-flight (TOF) is the simplest mass analyzer, consisting only of a metal flight tube. The mass-to-charge ratios (m/z) of ions are determined by measuring the time it takes the ions to travel from source to detector. In a TOF measurement, an equal amount of kinetic energy is imparted to the analyte ions by placing them in a strong electric field formed by a large DC potential between two plates. Given that all ions of different m/z receive the same kinetic energy ($qV=mv^2/2$), low m/z ions will reach the detector sooner than high m/z ions.

Advantages of TOF MS include the capability to deliver complete mass spectra at high speed and with no mass range limit. The mass-resolving power in TOF measurement is, however, limited by the distribution of initial energy in the analyte molecules and the position of the ions prior to acceleration. Typically, the spatial focusing plane in a single-stage mass spectrometer is only a short distance from the acceleration region (i.e., the apparatus has a relatively short focal length), after which the ions will spread out. A two-stage acceleration system is often utilized to allow spatial focusing at a longer distance from the ion source. The spatial focusing plane can be brought to the detector plane by adjustment of the relative field strength between these acceleration stages. Within a certain mass window, energy focusing can be achieved by the technique of delayed extraction, also known as time-lag focusing. The most successful energy focusing method implemented to date is the "reflectron." In this method, an electrostatic ion mirror (the reflectron) is disposed at the distal end of the flight tube and the electrostatic field within the reflectron is oriented to oppose the acceleration field. Thus, the accelerated ions penetrate into the reflectron, and are ultimately reflected back toward a secondary (or "reflected") focal point. The more energetic ions penetrate more deeply into the reflectron and hence take longer to be reflected back out of the reflectron. Thus, the optics can be adjusted to bring ions of different energies to a space-time focus. While the addition of a mirror provides little improvement in theoretical resolution, it dramatically broadens the mass range of focus.

A triple quadrupole mass spectrometer is comprised of two mass analyzing quadrupoles (Q1 and Q3) and a radiofrequency-only quadrupole, q2. Quadrupole mass filters can be operated in two basic modes: mass-resolving mode and radio frequency only (RF-only) mode. In mass-resolving mode, quadrupoles are operated at a constant ratio. The operation points lie on a straight line in a stability diagram, known as the mass scan line. When all the experimental parameters are fixed, the mass scan line can be viewed as a collection of points representing particles with different mass-to-charge ratios: heavier ions at the left-lower region and lighter ions at the right-upper region. The portion of the mass scan line that is intercepted by the boundary of the stable region represents a transmission window. Only m/z ratios that fall into this window will be transmitted. The length of this segment defines the resolution of transmission. In RF-only mode, the DC voltage is removed. The mass scan line in this case coincides with the q axis. The transmission window is now between the m/z of infinity and the low-mass cut-off value. This operation mode is also known as the high-pass mode.

In a QqQ MS, the RF-only quadrupole (q2) functions as a collision cell in which the buffer gas pressure is maintained at about from 1 to about 119 mTorr. Precursor ions selected by Q1 enter the RF collision quadrupole, q2, where they undergo collision-induced dissociation. Product ions are then mass filtered by scanning the third quadrupole, Q3, to produce the product mass spectrum.

The most commonly used ion detectors are electron multiplier detectors, including channel electron multipliers (CEM) and microchannel plate detectors (MCP). These detectors operate by means of secondary electron generation. Initial secondary electrons generated upon impact of incident ions start an electron avalanche that produces an output signal. Because the response of electron multiplier detectors to ions with a fixed kinetic energy falls off significantly with increasing mass, ion detectors based on different detection mechanisms have been developed. One strategy is to detect the charge directly. Briefly, as ions approach the detector, image charges are formed on the surface of the detector, which are then picked up by an external circuit generating an output signal. The major limitation in this detection scheme is the low sensitivity due to the lack of inherent amplification. In another approach, the energy deposited in a suitable material by impact of an ion can be detected. Using two superconducting layers separated by an insulating layer, ions that strike the detector create non-thermal phonons (lattice vibrations). Phonons with sufficiently high energy can break the weakly bound electron pairs (Cooper pairs) in the superconducting layer, which results in a measurable tunneling current through the insulating baffler. These detectors are more efficient than MCP's, especially for detecting large ions. However, these types of detectors require liquid helium cooling and generally have a small active area, which limits their use in routine applications.

Tandem mass spectrometry (MS-MS) is a related technology where two or more mass spectrometers are coupled together to (i) separate compounds by molecular weight by one mass spectrometer, (ii) fragment the compounds as they exit the mass spectrometer, and (iii) identify the fragments by a second mass spectrometer. Isobaric tags, such as, for example, isobaric tags for relative and absolute quantification (iTRAQ) and tandem mass tags (TMT), can be used to help quantify proteins and peptides. These tags can be attached to probes described herein to aid in the quantification and identification of peptide and proteins in a sample.

B. Fluorosequencing

Fluorosequencing has been found to provide single molecule resolution for the sequencing of proteins of interest (Swaminathan, 2010; U.S. Pat. No. 9,625,469; U.S. patent application Ser. No. 15/461,034; U.S. patent application Ser. No. 15/510,962). One of the hallmarks of fluorosequencing is introduction of a fluorophore or other label into specific amino acid residues of the peptide sequence. This step can involve the introduction of one or more amino acid residues with a unique labeling moiety. One, two, three, four, five, six, or more different amino acids residues may be labeled with a labeling moiety. The labeling moiety that may be used include fluorophores, chromophores, or a quencher. Each of these amino acid residues may include cysteine, lysine, glutamic acid, aspartic acid, tryptophan, tyrosine, serine, threonine, arginine, histidine, methionine, asparagine, and glutamine. Each of these amino acid residues may be labeled with a different labeling moiety. Multiple amino acid residues may be labeled with the same labeling moiety such as aspartic acid and glutamic acid or asparagine and glutamine. While this technique may be used with labeling moieties, such as those described above, other labeling moiety may be used in fluorosequencing-like methods, such as synthetic oligonucleotides or peptide-nucleic acid, may be used. In particular, the labeling moiety used in the instant applications may be suitable to withstand the conditions of removing one or more of the amino acid residues. Some non-limiting examples of potential labeling moieties that may be used in the instant methods include those which emit a fluorescence signal in the red to infrared spectra such as an Alexa Fluor® dye, an Atto dye, Janelia Fluor® dye, a rhodamine dye, or other similar dyes. Examples of each of these dyes which were capable of withstanding the conditions of removing the amino acid residues include Alexa Fluor® 405, Rhodamine B, tetramethyl rhodamine, Janelia Fluor® 549, Alexa Fluor® 555, Atto647N, and (5)6-naptho-fluorescein. The labeling moiety may be a fluorescent peptide or protein or a quantum dot.

Alternatively, synthetic oligonucleotides or oligonucleotide derivatives may be used as the labeling moiety for the peptides. For example, thiolated oligonucleotides are commercially available, and may be coupled to peptides using known methods. Commonly available thiol modifications are 5' thiol modifications, 3' thiol modifications, and dithiol modifications and each of these modifications may be used to modify the peptide. Following oligonucleotide coupling to the peptides as above, the peptides may be subjected to Edman degradation (Edman et al., 1950) and the oligonucleotides may be used to determine the presence of a specific amino acid residue in the remaining peptide sequence. Alternatively, the labeling moiety may be a peptide-nucleic acid. The peptide-nucleic acid may be attached to the peptide sequence on specific amino acid residues.

One element of fluorosequencing is the removal of the labeled peptides through techniques, such as Edman degradation and subsequent visualization, to detect a reduction in fluorescence, indicating a specific amino acid has been cleaved. Removal of each amino acid residue is carried out through a variety of different techniques including Edman degradation and proteolytic cleavage. The techniques may include using Edman degradation to remove the terminal amino acid residue. Alternatively, the techniques may involve using an enzyme to remove the terminal amino acid residue. These terminal amino acid residues may be removed from either the C-terminus or the N-terminus of the peptide chain. In situations in which Edman degradation is used, the amino acid residue at the N-terminus of the peptide chain is removed.

The methods of sequencing or imaging the peptide sequence may comprise immobilizing the peptide on a surface. The peptide may be immobilized using a cysteine residue, the N terminus, or the C terminus. The peptide may be immobilized by reacting the cysteine residue with the surface. The peptide may be immobilized on a surface, such as a surface that is optically transparent across the visible spectra and/or the infrared spectra, possesses a refractive index between 1.3 and 1.6, is between 10 to 50 nm thick, and/or is chemically resistant to organic solvents as well as strong acid such as trifluoroacetic acid. A large range of substrates (like fluoropolymers (Teflon-AF (Dupont), Cytop® (Asahi Glass, Japan)), aromatic polymers (polyxylenes (Parylene, Kisco, Calif.), polystyrene, polymethmethylacrytate) and metal surfaces (Gold coating)), coating schemes (spin-coating, dip-coating, electron beam deposition for metals, thermal vapor deposition and plasma enhanced chemical vapor deposition) and functionalization methodologies (polyallylamine grafting, use of ammonia gas in PECVD, doping of long chain end-functionalized fluorous alkanes etc.) may be used in the methods described herein as a useful surface. A 20 nm thick, optically transparent fluoropolymer surface made of Cytop® may be used in the methods described herein. The surfaces used herein may be further derivatized with a variety of fluoroalkanes that will sequester peptides for sequencing and modified targets for selection. Alternatively, an aminosilane modified surfaces may be used in the methods described herein. The methods may comprise immobilizing the peptides on the surface of beads, resins, gels, quartz particles, glass beads, or combinations thereof. In some non-limiting examples, the methods contemplate using peptides that have been immobilized on the surface of Tentagel® beads, Tentagel® resins, or other similar beads or resins. The surface used herein may be coated with a polymer, such as polyethylene glycol. The surface may be amine functionalized or thiol functionalized.

Finally, each of these sequencing techniques involves imaging the peptide sequence to determine the presence of one or more labeling moiety on the peptide sequence. These images may be taken after each removal of an amino acid residue and used to determine the location of the specific amino acid in the peptide sequence. These methods can result in the elucidation of the location of the specific amino acid in the peptide sequence. These methods may be used to determine the locations of specific amino acid residues in the peptide sequence or these results may be used to determine the entire list of amino acid residues in the peptide sequence. The methods may involve determining the location of one or more amino acid residues in the peptide sequence and comparing these locations to known peptide sequences and determining the entire list of amino acid residues in the peptide sequence.

The imaging methods used in the sequencing techniques may involve a variety of different methods, such as fluorimetry and fluorescence microscopy. The fluorescent methods may employ such fluorescent techniques, such as fluorescence polarization, Forster resonance energy transfer (FRET), or time-resolved fluorescence. Fluorescence microscopy may be used to determine the presence of one or more fluorophores in the single molecule quantity. Such imaging methods may be used to determine the presence or absence of a label on a specific peptide sequence. After repeated cycles of removing an amino acid residue and imaging the peptide sequence, the position of the labeled amino acid residue can be determined in the peptide.

C. Combinatorial Assembly:

Combinatorial assembly may be used to produce barcode sequences, such as, for example, nucleic acid and tandem mass spectrometry barcode sequences. The combinatorial assembly may be a split and pool technique. In some embodiments, for example, a support comprising a primer sequence with an oligonucleotide sequence is pooled together and randomly distributed into a 96, 368, or more well plates. Each well can comprise a particular nucleotide sequence. Strand extension may be used to extend the oligonucleotide sequence, introducing the particular sequence to a set of the supports comprising the primer sequence. The supports may then be pooled together. The pooled supports may be randomly distributed into a new set of wells comprising a particular nucleotide sequence. Repeated cycles of splitting and pooling of the supports can ensure a unique barcoded sequence on individual supports distinct from other beads.

D. Nanopore Sequencing:

Nanopore sequencing is a third-generation sequencing method of biopolymers, such as, for example polynucleotides. Both biological and solid-state methods exist. The method utilizes electrophoresis to transport a polymer through a small orifice, such as, for example, a porn protein or nanometer sized holes in a metal or metal alloy. These small orifices can be embedded in a surface (e.g., a lipid membrane or metal or metal alloy), to create a porous surface. An electric current can be measured from the system, and the difference in electrical signal can be measured for each polymer subunit to determine the identity of that polymer subunit (e.g., DNA and RNA bases). The system can be designed in a way in which changes in electrical signals for each hole can be quantified. Considering the methods and compositions described herein, the biopolymers of nanopore sequencing can be adapted as barcodes.

II. DEFINITIONS

As used herein, the term "amino acid" in general refers to organic compounds that contain at least one amino group, —$NH_2$, which may be present in its ionized form, —$NH_3^+$, and one carboxyl group, —COOH, which may be present in its ionized form, —$COO^-$, where the carboxylic acids are deprotonated at neutral pH, having the basic formula of $NH_2CHRCOOH$. An amino acid and thus a peptide has an N (amino)-terminal residue region and a C (carboxy)-terminal residue region. Types of amino acids include at least 20 that are considered "natural" as they comprise the majority of biological proteins in mammals and include amino acid, such as lysine, cysteine, tyrosine, threonine, etc. Amino acids may also be grouped based upon their side chains, such as those with a carboxylic acid groups (at neutral pH), including aspartic acid or aspartate (Asp; D) and glutamic acid or glutamate (Glu; E); and basic amino acids (at neutral pH), including lysine (Lys; L), arginine (Arg; N), and histidine (His; H).

As used herein, the term "terminal" is referred to as singular terminus and plural termini.

As used herein, the term "side chains" or "R" refers to unique structures attached to the alpha carbon (attaching the amine and carboxylic acid groups of the amino acid) that render uniqueness to each type of amino acid. R groups have a variety of shapes, sizes, charges, and reactivities, such as charged polar side chains, either positively or negatively charged, such as lysine (+), arginine (+), histidine (+), aspartate (−), and glutamate (−); amino acids can also be basic, such as lysine, or acidic, such as glutamic acid; uncharged polar side chains have hydroxyl, amide, or thiol groups, such as cysteine having a chemically reactive side chain, i.e., a thiol group that can form bonds with another cysteine, serine (Ser) and threonine (Thr), that have hydroxylic R side chains of different sizes; asparagine (Asn), glutamine (Gln), and tyrosine (Tyr); non-polar hydrophobic amino acid side chains include the amino acid glycine, alanine, valine, leucine, and isoleucine having aliphatic hydrocarbon side chains ranging in size from a methyl group for alanine to isomeric butyl groups for leucine and isoleucine; methionine (Met) has a thiol ether side chain; proline (Pro) has a cyclic pyrrolidine side group. Phenylalanine (with its phenyl moiety) (Phe) and tryptophan (Trp) (with its indole group) contain aromatic side chains, which are characterized by bulk as well as lack of polarity.

Amino acids can also be referred to by a name or 3-letter code or 1-letter code, for example, Cysteine, Cys, C; Lysine, Lys, K; Tryptophan, Trp, W, respectively.

Amino acids may be classified as nutritionally essential or nonessential, with the caveat that nonessential vs. essential may vary from organism to organism or vary during different developmental stages. Nonessential or conditional amino acids for a particular organism are those that are synthesized adequately in the body, typically in a pathway using enzymes encoded by several genes, as substrates to meet the needs for protein synthesis. Essential amino acids are amino acids that the organism is not able to produce or not able to produce enough of naturally, via de novo pathways, for example lysine in humans. Humans obtain essential amino acids through their diet, including synthetic supplements, meat, plants and other organisms.

"Unnatural" amino acids are those not naturally encoded or found in the genetic code nor produced via de novo pathways in mammals and plants. They can be synthesized by adding side chains not normally found or rarely found on amino acids in nature.

As used herein, β amino acids, which have their amino group bonded to the β carbon rather than the α carbon as in the 20 standard biological amino acids, are unnatural amino acids. The only common naturally occurring β amino acid is β-alanine.

As used herein, the terms "amino acid sequence", "peptide", "peptide sequence", "polypeptide", and "polypeptide sequence" are used interchangeably herein to refer to at least two amino acids or amino acid analogs that are covalently linked by a peptide (amide) bond or an analog of a peptide bond. The term peptide includes oligomers and polymers of amino acids or amino acid analogs. The term peptide also includes molecules that may be referred to as peptides, which may contain from about two (2) to about twenty (20) amino acids. The term peptide also includes molecules that are commonly referred to as polypeptides, which generally contain from about twenty (20) to about fifty amino acids (50). The term peptide also includes molecules that are commonly referred to as proteins, which may contain at least about fifty (50) amino acids. The amino acids of the peptide may be L-amino acids or D-amino acids. A peptide, polypeptide, or protein may be synthetic, recombinant, or naturally occurring. A synthetic peptide is a peptide that is produced by artificial means in vitro.

As used herein, the term “subset” refers to the N-terminal amino acid residue of an individual peptide molecule. A “subset” of individual peptide molecules with an N-terminal lysine residue is distinguished from a “subset” of individual peptide molecules with an N-terminal residue that is not lysine.

As used herein, the term “fluorescence” refers to the emission of visible light by a substance that has absorbed light of a different wavelength. Fluorescence may provide a non-destructive means of tracking and/or analyzing biological molecules based on the fluorescent emission at a specific wavelength. Proteins (including antibodies), peptides, nucleic acid, oligonucleotides (including single stranded and double stranded primers) may be “labeled” with a variety of extrinsic fluorescent molecules referred to as fluorophores.

As used herein, sequencing of peptides “at the single molecule level” refers to amino acid sequence information obtained from individual (i.e., single) peptide molecules in a mixture of diverse peptide molecules. It is not necessary that the present invention be limited to methods where the amino acid sequence information obtained from an individual peptide molecule is the complete or contiguous amino acid sequence of an individual peptide molecule. It may be sufficient that only partial amino acid sequence information is obtained, allowing for identification of the peptide or protein. Partial amino acid sequence information, including for example, the pattern of a specific amino acid residue (i.e., lysine) within individual peptide molecules, may be sufficient to uniquely identify an individual peptide molecule. For example, a pattern of amino acids such as X-X-X-Lys-X-X-X-X-Lys-X-Lys, which indicates the distribution of lysine molecules within an individual peptide molecule, may be searched against a known proteome of a given organism to identify the individual peptide molecule. It is not intended that sequencing of peptides at the single molecule level be limited to identifying the pattern of lysine residues in an individual peptide molecule; sequence information for any amino acid residue (including multiple amino acid residues) may be used to identify individual peptide molecules in a mixture of diverse peptide molecules.

As used herein, “single molecule resolution” refers to the ability to acquire data (including, for example, amino acid sequence information) from individual peptide molecules in a mixture of diverse peptide molecules. In one non-limiting example, the mixture of diverse peptide molecules may be immobilized on a solid surface (including, for example, a glass slide, or a glass slide whose surface has been chemically modified). This may include the ability to simultaneously record the fluorescent intensity of multiple individual (i.e., single) peptide molecules distributed across the glass surface. Optical devices are commercially available that can be applied in this manner. For example, a conventional microscope equipped with total internal reflection illumination and an intensified charge-couple device (CCD) detector is available (see Braslaysky et al., 2003). Imaging with a high sensitivity CCD camera allows the instrument to simultaneously record the fluorescent intensity of multiple individual (i.e., single) peptide molecules distributed across a surface. Image collection may be performed using an image splitter that directs light through two band pass filters (one suitable for each fluorescent molecule) to be recorded as two side-by-side images on the CCD surface. Using a motorized microscope stage with automated focus control to image multiple stage positions in the flow cell may allow millions of individual single peptides (or more) to be sequenced in one experiment.

The term “single-cell proteomics”, as used herein, refers to the study of the proteome of a cell. The proteome may be of a single cell. The proteome may be of a cluster of cells. The cluster of cells may be at least two cells. The cluster of cells may be 2, 5, 10, 20, 30, 40, 50, 60, 70, 80, 90, 100, or more cells. The cluster of cells may be from 2 to 10 cells. In some embodiments, the proteome of a single cell comprises proteins, peptides, or a combination thereof. In some embodiments, studying the proteome comprises determining the amino acid sequence for at least one peptide, protein, or combination thereof. In some embodiments, the amino acid sequence is determined by sequencing peptides, proteins, or a combination thereof. The cells may be eukaryotic, prokaryotic, or archaean.

The term “support”, as used herein, refers to as a solid or semi-solid support. In some embodiments, the support is a bead or a resin.

The term “pendant” or “pendant group”, as used herein, refers to a molecule or group of molecules attached to a scaffold molecule. In some embodiments, the scaffold molecule comprises the support. In some embodiments, a plurality of pendant groups are attached to the support. In some embodiments, the plurality of pendant groups attached to a particular support are substantially identical.

The term “capture moiety” or “conjugating group”, as used herein, refers to a molecule that may react to a peptide or protein. In some embodiments, the capture moiety reacts with the N-terminus of the peptide or protein. In some embodiments, the capture moiety reacts with the C-terminus of the peptide or protein. In some embodiments, the capture moiety reacts with the side chain cysteine of the peptide or protein.

The term “cleavable unit”, as used herein, refers to a molecule that can be split into at least two molecules. Non-limiting examples of cleavage conditions to split a cleavable unit include: enzymes, nucleophilic or basic reagents, reducing agents, photo-irradiation, electrophilic or acidic reagents, organometallic or metal reagents, and oxidizing reagents.

The term “barcode” or “barcode sequence” as used herein, refers to a molecule that can be identified to distinguish a probe, a peptide, a protein, or any combination thereof from another probe, peptide, protein, or any combination thereof. In general, a barcode or barcode sequence labels a molecule or provides a molecule with an identity. The barcode can be an artificial molecule or a naturally occurring molecule. In some embodiments, at least a portion of the barcodes in a population of barcodes comprise barcodes that are different from another barcode in the population of barcodes. In some embodiments, at least about 10%, 20%, 30%, 40%, 50%, 60%, 70%, 80%, 90%, 95%, 99%, or more of the barcodes are different. The diversity of different barcodes in a population of barcodes can be randomly generated or non-randomly generated.

The term “nucleic acid barcode sequence”, as used herein, refers to a molecule with a particular sequence of nucleic acid. Generally, a nucleic acid barcode sequence can include one or more nucleotide sequences that can be used to identify one or more particular nucleic acids. The nucleic acid barcode sequence can be an artificial sequence or can be a naturally occurring sequence. A nucleic acid barcode sequence can comprise at least about 1, 2, 3, 4, 5, 6, 7, 8, 9, 10, 11, 12, 13, 14, 15, 16, 17, 18, 19, 20 or more consecutive nucleotides. In some embodiments, a nucleic acid barcode sequence comprises at least about 10, 20, 30, 40, 50, 60, 70, 80, 90, 100 or more consecutive nucleotides. In some embodiments, at least a portion of the nucleic acid barcode sequences in a population of nucleic acids comprising barcodes is different. In some embodiments, at least about 10%, 20%, 30%, 40%, 50%, 60%, 70%, 80%, 90%, 95%, 99%, or more of the nucleic acid barcode sequences are different. The diversity of different nucleic acid barcode sequences in a population of nucleic acids comprising nucleic acid barcode sequences can be randomly generated or non-randomly generated.

The term "linker", as described herein couples at least two molecules. In some embodiments, a linker couples at least two molecules directly or indirectly.

The term "reversing agent", "reversing reagent", or "releasing agent" as described herein refers to a reagent that cleaves at least one bond to cause the release of a peptide or protein from a probe or a component of the probe. The reversing agent may be a chemical or an enzyme. The reversing or releasing agent may cleave a cleavable unit, an imidazolinone, or a combination thereof.

The term "nucleic acid" as used herein generally refers to a polymeric form of nucleotides of any length, either ribonucleotides (RNA), deoxyribonucleotides (DNA) or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus, the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule.

The sequencing reactions may comprise, for example, capillary sequencing, next generation sequencing, Sanger sequencing, sequencing by synthesis, single molecule nanopore sequencing, sequencing by ligation, sequencing by hybridization, sequencing by nanopore current restriction, or a combination thereof. Sequencing by synthesis may comprise reversible terminator sequencing, processive single molecule sequencing, sequential nucleotide flow sequencing, or a combination thereof. The single molecule sequencing may provide single molecule resolution. Sequential nucleotide flow sequencing may comprise pyrosequencing, pH-mediated sequencing, semiconductor sequencing or a combination thereof. Conducting one or more sequencing reactions may comprise whole genome sequencing or exome sequencing.

The hybridization reactions may comprise, for example, fluorescent in-situ hybridization (FISH), DNA paint, multi-barcode identification (e.g., MER-FISH).

The sequencing reactions or hybridization reactions may comprise one or more capture probes or libraries of capture probes. At least one of the one or more capture probe libraries may comprise one or more capture probes to 1, 2, 3, 4, 5, 6, 7, 8, 9, 10, 11, 12, 13, 14, 15 or more genomic regions. The libraries of capture probes may be at least partially complementary. The libraries of capture probes may be fully complementary. The libraries of capture probes may be at least about 5%, 10%, 15%, 20%, %, 25%, 30%, 35%, 40%, 45%, 50%, 55%, 60%, 70%, 80%, 90%, 95%, 97% or more complementary.

The methods and systems disclosed herein may further comprise conducting one or more sequencing reactions or hybridization reactions on one or more capture probe free nucleic acid molecules. The methods and systems disclosed herein may further comprise conducting one or more sequencing reactions or hybridization reactions on one or more subsets on nucleic acid molecules comprising one or more capture probe free nucleic acid molecules.

The term "label" as used herein is the introduction of a chemical group to the molecule, which generates some form of measurable signal. Such a signal may include, but is not limited to, fluorescence, visible light, mass, radiation, or a nucleic acid sequence.

Attribution probability mass function—for a given fluorosequence, the posterior probability mass function of its source proteins, i.e. the set of probabilities $P(p_i/f_i)$ of each source protein $p_i$, given an observed fluorosequence When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means =NH; "cyano" means —CN; "isocyanate" means —N=C=O; "azido" means —$N_3$; in a monovalent context "phosphate" means —$OP(O)(OH)_2$ or a deprotonated form thereof in a divalent context "phosphate" means —OP(O)(OH)O— or a deprotonated form thereof "mercapto" means —SH; and "thio" means=S; "sulfonyl" means —$S(O)_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "═══" represents a single bond or a double bond. Thus, the formula

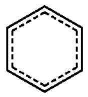

covers, for example,

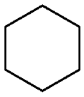, 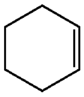, 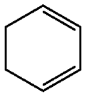, 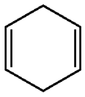 and 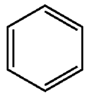.

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol “ ” means a single bond where the group attached to the thick end of the wedge is “out of the page.” The symbol “ ” means a single bond where the group attached to the thick end of the wedge is “into the page”. The symbol “ ” means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

“Electron withdrawing group”, as described herein, refers to a group that draws electrons away from a reaction center. In some embodiments, the electron withdrawing group draws electrons away from a reaction center by inductive effects. In some embodiments, the electron withdrawing group draws electrons away from a reaction center by resonance effects. In some embodiments, the electron withdrawing group draws electrons away from a reaction center by inductive effects and resonance effects. In some embodiments, the group can have partial electron withdrawing characteristics. In some embodiments, the electron withdrawing group is positioned ortho, meta, or para from the reaction center. In some embodiments, the position of the group in relation to the reaction center determines the group’s electron withdrawing characteristic. More than one electron withdrawing group can be in proximity to a reaction center. Examples of electron withdrawing groups are: H, $-NO_2$, —CN, —COOH, substituted or unsubstituted alkyl, substituted or unsubstituted heteroalkyl (e.g., $-NMe_2$, $-NMe_3^+$), heteroaromatic atom (e.g., O, N, S), halo, haloalkyl, and —OH. In another examples of electron withdrawing groups include $-NO_2$, —CN, —COOH, substituted or unsubstituted alkyl, substituted or unsubstituted heteroalkyl (e.g., $-NMe_2$, $-NMe_3^+$), heteroaromatic atom (e.g., O, N, S), halo, haloalkyl, and —OH.

When a variable is depicted as a “floating group” on a ring system, for example, the group “R” in the formula:

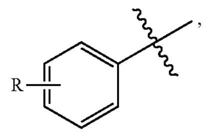

then the variable may replace any hydrogen atom attached to any of the ring atoms, including a depicted, implied, or expressly defined hydrogen, so long as a stable structure is formed. When a variable is depicted as a “floating group” on a fused ring system, as for example the group “R” in the formula:

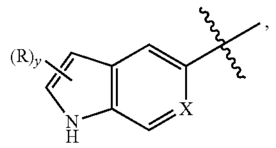

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter “y” immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: “Cn” defines the exact number (n) of carbon atoms in the group/class. “Cn” defines the maximum number (n) of carbon atoms that can be in the group/class, with the minimum number as small as possible for the group/class in question. For example, it is understood that the minimum number of carbon atoms in the groups “alkyl$_{(C\leq 8)}$”, “cycloalkanediyl$_{(C\leq 8)}$”, “heteroaryl$_{(C\leq 8)}$”, and “acyl$_{(C\leq 8)}$” is one, the minimum number of carbon atoms in the groups “alkenyl$_{(C\leq 8)}$”, “alkynyl$_{(C\leq 8)}$”, and “heterocycloalkyl$_{(C\leq 8)}$” is two, the minimum number of carbon atoms in the group “cycloalkyl$_{(C\leq 8)}$” is three, and the minimum number of carbon atoms in the groups “aryl$_{(C\leq 8)}$” and “arenediyl$_{(C\leq 8)}$” is six. “Cn-n'” defines both the minimum (n) and maximum number (n') of carbon atoms in the group. Thus, “alkyl$_{(C2\text{-}10)}$” designates those alkyl groups having from 2 to 10 carbon atoms. These carbon number indicators may precede or follow the chemical groups or class it modifies and it may or may not be enclosed in parenthesis, without signifying any change in meaning. Thus, the terms “C5 olefin”, “C5-olefin”, “olefin$_{(C5)}$”, and “olefin$_{C5}$” are all synonymous. When any of the chemical groups or compound classes defined herein is modified by the term “substituted”, any carbon atom in the moiety replacing the hydrogen atom is not counted. Thus methoxyhexyl, which has a total of seven carbon atoms, is an example of a substituted alkyl$_{(C1\text{-}6)}$ Unless specified otherwise, any chemical group or compound class listed in a claim set without a carbon atom limit has a carbon atom limit of less than or equal to twelve.

The term “saturated” when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term “saturated” is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

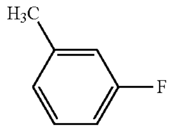

is also taken to refer to

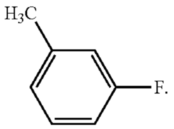

Aromatic compounds may also be depicted using a circle to represent the delocalized nature of the electrons in the fully conjugated cyclic π system, two non-limiting examples of which are shown below:

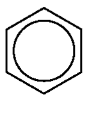 and 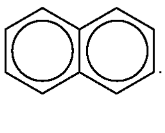.

The term "alkyl" when used without the "substituted" modifier refers to a monovalent saturated aliphatic group with a carbon atom as the point of attachment, a linear or branched acyclic structure, and no atoms other than carbon and hydrogen. The groups $—CH_3$ (Me), $—CH_2CH_3$ (Et), $—CH_2CH_2CH_3$ (n-Pr or propyl), $—CH(CH_3)_2$ (i-Pr, Tr or isopropyl), $—CH_2CH_2CH_2CH_3$ (n-Bu), $—CH(CH_3)CH_2CH_3$ (sec-butyl), $—CH_2CH(CH_3)_2$ (isobutyl), $—C(CH_3)_3$ (tert-butyl, t-butyl, t-Bu or Bu), and $—CH_2C(CH_3)_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups $—CH_2—$ (methylene), $—CH_2CH_2—$, $—CH_2C(CH_3)_2CH_2—$, and $—CH_2CH_2CH_2—$ are non-limiting examples of alkanediyl groups. The term "alkylidene" when used without the "substituted" modifier refers to the divalent group $=CRR'$ in which R and R' are independently hydrogen or alkyl. Non-limiting examples of alkylidene groups include: $=CH_2$, $=CH(CH_2CH_3)$, and $=C(CH_3)_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$. The following groups are non-limiting examples of substituted alkyl groups: $—CH_2OH$, $—CH_2C_1$, $—CF_3$, $—CH_2CN$, $—CH_2C(O)OH$, $—CH_2C(O)OCH_3$, $—CH_2C(O)NH_2$, $—CH_2C(O)CH_3$, $—CH_2OCH_3$, $—CH_2OC(O)CH_3$, $—CH_2NH_2$, $—CH_2N(CH_3)_2$, and $—CH_2CH_2C_1$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, $—CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups $—CH_2F$, $—CF_3$, and $—CH_2CF_3$ are non-limiting examples of fluoroalkyl groups.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, $—C_6H_4CH_2CH_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

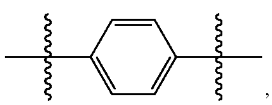, 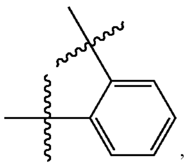,

-continued

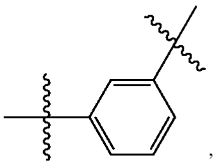

,

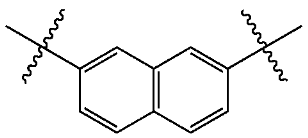

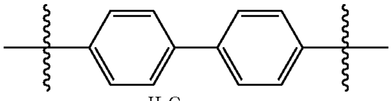

, and

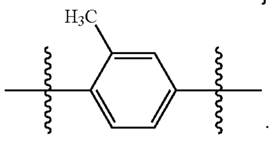

.

An "arene" refers to the class of compounds having the formula H—R, wherein R is aryl as that term is defined above. Benzene and toluene are non-limiting examples of arenes. When any of these terms is used with the "substituted" modifier, one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

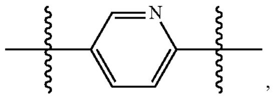

,

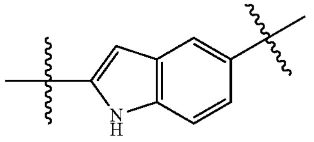

and

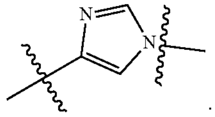

.

When any of these terms is used with the "substituted" modifier, one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$.

The term "alkoxy" when used without the "substituted" modifier refers to the group —OR, in which R is an alkyl, as that term is defined above. Non-limiting examples include: $—OCH_3$ (methoxy), $—OCH_2CH_3$ (ethoxy), $—OCH_2CH_2CH_3$, $—OCH(CH_3)_2$ (isopropoxy), or $—OC(CH_3)_3$ (tert-butoxy). The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$.

The term "alkylamino" when used without the "substituted" modifier refers to the group —NHR, in which R is an alkyl, as that term is defined above. Non-limiting examples include: $—NHCH_3$ and $—NHCH_2CH_3$. The term "dialkylamino" when used without the "substituted" modifier refers to the group —NRR', in which R and R' can be the same or different alkyl groups. Non-limiting examples of dialkylamino groups include: $—N(CH_3)_2$ and $—N(CH_3)(CH_2CH_3)$. When any of these terms is used with the "substituted" modifier, one or more hydrogen atom attached to a carbon atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$. The groups $—NHC(O)OCH_3$ and $—NHC(O)NHCH_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects. Unless otherwise specified based upon the above values, the term "about" means±5% of the listed value.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

The term "effective," as that term is used in the specification and/or claims, means adequate to accomplish a desired, expected, or intended result.

As used herein, the term "patient" or "subject" refers to a living animal organism, such as a human, monkey, cow, horse, sheep, goat, dog, cat, mouse, rat, guinea pig, chicken, turkey, duck, fish, or transgenic species thereof. In some embodiments, the patient is a mammalian organism such as a human, monkey, cow, horse, sheep, goat, dog, cat, mouse, rat, guinea pig, or transgenic species thereof. In certain embodiments, the patient or subject is a primate. Non-limiting examples of human patients are adults, juveniles, infants and fetuses.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The above definitions supersede any conflicting definition in any reference that is incorporated by reference herein. The fact that certain terms are defined, however, should not be considered as indicative that any term that is undefined is indefinite.

Rather, all terms used are believed to describe the disclosure in terms such that one of ordinary skill can appreciate the scope and practice the present disclosure.

In certain aspects, the disclosure provides a method of performing proteomics, comprising: (a) providing a support and a mixture comprising a cell, wherein the support has coupled thereto (i) a barcode and (ii) a capture moiety for capturing a protein or peptide of said cell; (b) using the capture moiety to capture the protein or peptide of the cell; and (c) subsequent to (b), (i) identifying the barcode and associating the barcode with the cell, (ii) sequencing the protein or peptide to identify the protein or peptide, or a sequence thereof; and (iii) using the barcode identified in (i) and the protein or peptide, or sequence thereof identified in (ii) to identify the protein or peptide, or sequence thereof as having originated from the cell.

The barcode may be a nucleic acid barcode sequence, an isobaric mass-tag (e.g., tandem mass tag (TMT)), amino acid sequences (e.g., arginine or poly arginine), ammonium, fluorophores, halogens (e.g., fluorine, chlorine, bromine, and iodine), biotin, polyethylene glycol (PEG), or any combination thereof. The barcode may be identified using optical detection, sequencing (e.g., sequencing by synthesis, fluorosequencing, nanopore sequencing), mass spectrometry, or any combination thereof. The barcode may improve the detection of the peptide or protein. The barcode may improve the ionization of the peptide or protein. The barcode may improve the ionization of the peptide or protein in positive ion mode or negative ion mode. The barcode may be a poly-arginine chain. The barcode may bind and improve nanopore translocation. The barcode may be an oligonucleotide-peptide hybrid.

In certain aspects, the disclosure provides a method of performing single-cell proteomics, comprising: (a) providing a support and a mixture comprising a cell, wherein the support has coupled thereto (i) a nucleic acid barcode sequence, and (ii) a capture moiety for capturing a protein or peptide of said cell; (b) using the capture moiety to capture the protein or peptide of the cell; and (c) subsequent to (b), (i) identifying the nucleic acid barcode sequence and associating the nucleic acid barcode sequence with the cell, (ii) sequencing the protein or peptide to identify the protein or peptide, or a sequence thereof; and (iii) using the barcode sequence identified in (i) and the protein or peptide, or sequence thereof identified in (ii) to identify the protein or peptide, or sequence thereof as having originated from the cell. In some embodiments, (ii) may comprise, instead of sequencing the protein or peptide, identifying or determining the mass of the protein or peptide. Determining the mass of the peptide or protein may be by mass spectrometry.

The barcode may be coupled to the support through a linker. The nucleic acid barcode sequence may be coupled to the support through a linker. The linker may couple at least two molecules or more. The linker may be coupled to at least three molecules or more. The linker may include a cleavable unit and a building block for barcoding a nucleic acid sequence. The linker may be a homofunctional or a heterofunctional linker. The linker may be a cleavable linker, cross-linker, a bifunctional linker, a trifunctional linker, a multi-functional linker, or any combination thereof. The linker may include functional groups, such as, for example, amines, sulfhydryls, acids, alcohols, bromides, maleamides, succinimidyl esters (NHS), sulfosuccinimidyl esters, disulfides, azides, alkynes, isothiocyanates (ITC), or combinations thereof. The linker may include protected functional groups, such as, for example, Boc, Fmoc, alkyl ester, Cbz, or combinations thereof. The barcode may be directly coupled to said support. The nucleic acid barcode sequence may be directly coupled to said support.

The mixture may comprise one cell. The mixture may comprise a plurality of cells, which plurality of cells may comprise the cell. The plurality of cells may be at least two cells, or more. The plurality of cells may be about 2, 5, 10, 15, 20, 40, 60, 80, 100, 200, 300, 400, 500, 600, 700, 800, 900, 1000, or more cells. The plurality of cells may be from about 2 to about 60 cells. The plurality of cells may be from about 2 to about 40 cells. The plurality of cells may be from about 2 to about 20 cells. The plurality of cells may be from about 2 to about 10 cells. The plurality of cells may be from about 5 to about 10 cells. The cell or the plurality of cells may be isolated from a biological sample. The biological sample may be derived from tissue, blood, urine, saliva, lymphatic fluid, or any combination thereof.

In some embodiments, (a) may comprise a single support. In some embodiments, (a) may comprise providing a plurality of supports, which plurality of supports may comprise the support. The plurality of supports may be at least two supports, or more. The plurality of supports may be about 2, 5, 10, 15, 20, 40, 60, 80, 100, 200, 300, 400, 500, 600, 700, 800, 900, 1000, or more supports. The plurality of supports may be from about 2 to about 60 supports. The plurality of supports may be from about 2 to about 40 supports. The plurality of supports may be from about 2 to about 20 supports. The plurality of supports may be from about 2 to about 10 supports. The plurality of supports may be from about 2 to about 5 supports.

In some embodiments, (a) may comprise providing a plurality of supports and the mixture comprising a plurality of cells, which plurality of supports comprises the support and the plurality of cells comprises the cell. The plurality of cells may be at least two cells, or more. The plurality of cells may be about 2, 5, 10, 15, 20, 40, 60, 80, 100, 200, 300, 400, 500, 600, 700, 800, 900, 1000, or more cells. The plurality of cells may be from about 2 to about 60 cells. The plurality of cells may be from about 2 to about 40 cells. The plurality of cells may be from about 2 to about 20 cells. The plurality of cells may be from about 2 to about 10 cells. The plurality of cells may be from about 5 to about 10 cells. The cell or plurality of cells may be isolated from a biological sample. The biological sample may be derived from tissue, blood, urine, saliva, lymphatic fluid, or any combination thereof. The plurality of supports may be at least two supports, or more. The plurality of supports may be about 2, 5, 10, 15, 20, 40, 60, 80, 100, 200, 300, 400, 500, 600, 700, 800, 900, 1000, or more supports. The plurality of supports may be from about 2 to about 60 supports. The plurality of supports may be from about 2 to about 40 supports. The plurality of supports may be from about 2 to about 20 supports. The plurality of supports may be from about 2 to about 10 supports. The plurality of supports may be from about 2 to about 5 supports.

The support may be a solid support or a semi-solid support. The solid support or semi-solid support may be a bead. The bead may be a gel bead. The bead may be a polymer bead. The support may be a resin. Non-limiting supports may comprise, for example, agarose, sepharose, polystyrene, polyethylene glycol (PEG), or any combination thereof. The support may be a polystyrene bead. The support may include functional groups, such as, for example, amines, sulfhydryls, acids, alcohols, bromides, maleamides, succinimidyl esters (NHS), sulfosuccinimidyl esters, disulfides, azides, alkynes, isothiocyanates (ITC), or combinations thereof. The support may be a PEGA resin. The support may be an amino PEGA resin. The support may comprise an amine group. The support may include protected functional groups, such as, for example, Boc, Fmoc, alkyl ester, Cbz, or combinations thereof. The bead may contain a metal core. The bead may be a polymer magnetic bead. The polymer magnetic bead may comprise a metal-oxide. The support may comprise at least one iron oxide core.

The support may have coupled thereto a barcode. The support may have coupled thereto a nucleic acid barcode sequence. The support may have directly coupled thereto a barcode. The support may have directly coupled thereto a nucleic acid barcode sequence. The support may have coupled thereto a plurality of barcodes. The support may have coupled thereto a plurality of nucleic acid barcode sequences. The support may have directly coupled thereto a plurality of barcodes. The support may have directly coupled thereto a plurality of nucleic acid barcode sequence. The support may be coupled to a pendant group. The support may be coupled to a plurality of pendant groups. The support may be coupled to a barcode and to a pendant group. The support may be coupled to a nucleic acid barcode sequence and to a pendant group. The support may be directly coupled to a barcode and to a pendant group. The support may be directly coupled to a nucleic acid barcode sequence and to a pendant group. The support may be coupled to a barcode and to a plurality of pendant groups. The support may be coupled to a nucleic acid barcode sequence and to a plurality of pendant groups. The support may be directly coupled to a barcode and to a plurality of pendant groups. The support may be directly coupled to a nucleic acid barcode sequence and to a plurality of pendant groups. The support may be coupled to a plurality of barcodes and to a plurality of pendant groups. The support may be coupled to a plurality of nucleic acid barcode sequences and to a plurality of pendant groups. The support may be directly coupled to a plurality of barcodes and to a plurality of pendant groups. The support may be directly coupled to a plurality of nucleic acid barcode sequences and to a plurality of pendant groups.

A pendant group may comprise at least one capture moiety. A pendant group may comprise at least one cleavable unit. A pendant group may comprise at least one barcode. A pendant group may comprise at least one nucleic acid barcode sequence. A pendant group may comprise at least one building block for the barcode(s). A pendant group may comprise at least one building block for the nucleic acid barcode sequence(s). A pendant group may comprise at least one capture moiety and at least one cleavable unit. A pendant group may comprise at least one capture moiety and at least one barcode. A pendant group may comprise at least one capture moiety and at least one nucleic acid barcode sequence. A pendant may comprise at least one capture moiety and at least one building block for the barcode(s). A pendant may comprise at least one capture moiety and at least one building block for the nucleic acid barcode sequence(s). A pendant group may comprise at least one cleavable unit and at least one barcode. A pendant group may comprise at least one cleavable unit and at least one nucleic acid barcode sequence. A pendant group may comprise at least one cleavable unit and at least one building block for the barcode(s). A pendant group may comprise at least one cleavable unit and at least one building block for the nucleic acid barcode sequence(s). A pendant group may comprise at least one barcode and at least one building block for the barcode(s). A pendant group may comprise at least one nucleic acid barcode sequence and at least one building block for the nucleic acid barcode sequence(s). A pendant group may comprise at least one capture moiety, at least one cleavable unit, and at least one barcode. A pendant group may comprise at least one capture moiety, at least one cleavable unit, and at least one nucleic acid barcode sequence. A pendant group may comprise at least one capture moiety, at least one barcode, and at least one building block for the barcode(s). A pendant group may comprise at least one capture moiety, at least one nucleic acid barcode sequence, and at least one building block for the nucleic acid barcode sequence(s). A pendant group may comprise at least one cleavable unit, at least one barcode, and at least one building block for the barcode(s). A pendant group may comprise at least one cleavable unit, at least one nucleic acid barcode sequence, and at least one building block for the nucleic acid barcode sequence(s). A pendant group may comprise at least one capture moiety, at least one cleavable unit, and at least one building block for the barcode(s). A pendant group may comprise at least one capture moiety, at least one cleavable unit, and at least one building block for the nucleic acid barcode sequence(s). A pendant group may comprise at least one capture moiety, at least one cleavable unit, at least one barcode, and at least one building block for the barcode(s). A pendant group may comprise at least one capture moiety, at least one cleavable unit, at least one nucleic acid barcode sequence, and at least one building block for the nucleic acid barcode sequence(s).

The support may be coupled to at least one pendant. The support may be coupled to a plurality of pendants. The support may be coupled to a plurality of pendants, wherein pendant groups of said plurality of pendants may be substantially identical. The support may be coupled to at least one barcode. The support may be coupled to at least one nucleic acid barcode sequence. The support may be coupled to at least one pendant and at least one barcode. The support may be coupled to at least one pendant and at least one nucleic acid barcode sequence. The support may be coupled to a first position of the cleavable unit and the capture moiety may be coupled to a second position of the cleavable unit. A first position of the support may be coupled at least one barcode, and a second position of the support may be coupled to a first position of the cleavable unit and the capture moiety may be coupled to a second position of the cleavable unit. A first position of the support may be coupled at least one nucleic acid barcode sequence, and a second position of the support may be coupled to a first position of the cleavable unit and the capture moiety may be coupled to a second position of the cleavable unit.

A support may be coupled to at least one pendant. The support may be coupled to a plurality of pendants. The support may be coupled to a plurality of pendants, wherein pendant groups of said plurality of pendants may be substantially identical. A support may comprise at least one pendant group comprising at least one capture moiety and at least one barcode. A support may comprise at least one pendant group comprising at least one capture moiety and at least one nucleic acid barcode sequence. A support may comprise at least one pendant group comprising at least one capture moiety and at least one barcode, and wherein the at least one pendant group and the at least one barcode are separately coupled to said support. A support may comprise at least one pendant group comprising at least one capture moiety and at least one nucleic acid barcode sequence, and wherein the at least one pendant group and the at least one nucleic acid barcode sequence are separately coupled to said support. The support may be coupled to at least one cleavable unit. The support may be coupled to at least one cleavable unit, wherein the cleavable unit is coupled to at least one building block for barcoding. The support may be coupled to at least one cleavable unit, wherein the cleavable unit is coupled to at least one building block for barcoding, wherein the building block for barcoding is coupled to at least one capture moiety. The support may be coupled to at least one cleavable unit, wherein the cleavable unit is coupled to at least one building block for barcoding, wherein the building block for barcoding is coupled to at least one barcode and at least one capture moiety. The support may be coupled to at least one cleavable unit, wherein the cleavable unit is coupled to at least one building block for barcoding, wherein the building block for barcoding is coupled to at least one nucleic acid barcode sequence and at least one capture moiety. The support may be coupled to (a) at a first position of at least one cleavable unit, (b) a first position of at least one building block for barcoding may be coupled to a second position of the at least one cleavable unit, (c) at least one capture moiety may be coupled to a second position of the at least one building block for barcoding, and (d) at least one barcode may be coupled to a third position of the at least one building block for barcoding. The support may be coupled to (a) at a first position of at least one cleavable unit, (b) a first position of at least one building block for barcoding may be coupled to a second position of the at least one cleavable unit, (c) at least one capture moiety may be coupled to a second position of the at least one building block for barcoding, and (d) at least one nucleic acid barcode sequence may be coupled to a third position of the at least one building block for barcoding.

A support may be coupled to at least one pendant. The support may be coupled to a plurality of pendants. The support may be coupled to a plurality of pendants, wherein pendant groups of said plurality of pendants may be substantially identical. The plurality of pendant groups may comprise at least two identical pendant groups. The plurality of pendant groups may comprise at least two identical pendant groups. The plurality of pendant groups may comprise at least 10 identical pendant groups. The plurality of pendant groups may comprise at least 100 identical pendant groups. The plurality of pendant groups may comprise at least 1000 identical pendant groups. The plurality of pendant groups may comprise at least 10000 identical pendant groups. The plurality of pendant groups may comprise at least $10^5$ identical pendant groups. The plurality of pendant groups may comprise at least $10^{10}$ identical pendant groups.

The plurality of pendant groups may comprise at least $10^{12}$ identical pendant groups. The plurality of pendant groups may comprise at least $10^{15}$ identical pendant groups.

A capture moiety may react with at least one peptide or protein. A capture moiety may react with the N-terminus of at least one peptide or protein. A capture moiety may react with the C-terminus of at least one peptide or protein. A capture moiety may react with one peptide or protein. A capture moiety may react with the N-terminus of one peptide or protein. A capture moiety may react with the C-terminus of one peptide or protein. Each peptide or protein of a cell may be captured by a plurality of capture moieties. The support may further comprise a capture moiety that can capture a molecule that is not a peptide or protein molecule. The support may further comprise a capture moiety that can capture a nucleic acid molecule. The support may further comprise a capture moiety that can capture a ribonucleic acid molecule. A capture moiety may react with at least one nucleic acid molecule. A capture moiety may react with at least one ribonucleic acid (RNA) molecule. The capture moiety may capture RNA by primer extension. The captured RNA may be amplified.

A capture moiety may not comprise an antibody. A capture moiety may comprise an aromatic or a heteroaromatic carboxaldehyde. A capture moiety may comprise 2-pyridinecarboxaldehyde or a derivative thereof. A capture moiety may comprise formula (I):

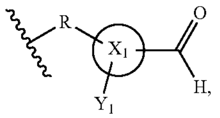

wherein $X_1$ is substituted or unsubstituted arenediyl$_{(C\leq 12)}$ or substituted or unsubstituted heteroarenediyl$_{(C\leq 12)}$; $Y_1$ is hydrogen or an electron withdrawing group; and R is a linker that is coupled to the solid support. The linker may comprise a monomer or a polymer. The linker may comprise a polypeptide, a polyethylene glycol, a polyamide, a heterocycle, or any combination thereof. The linker may comprise at least one oxo.

A capture moiety may comprise formula (Ia):

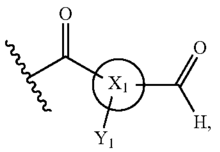

wherein $X_1$ is arenediyl$_{(C\leq 12)}$, heteroarenediyl$_{(C\leq 12)}$, or a substituted version of either of these groups; $Y_1$ is hydrogen or an electron withdrawing group; wherein said capture moiety is attached to said cleavable unit at the open valence of the carbonyl group. In some embodiments, $X_1$ is arenediyl$_{(C\leq 12)}$ or a substituted arenediyl$_{(C\leq 12)}$. In some embodiments, $X_1$ is arenediyl$_{(C\leq 12)}$. In some embodiments, $X_1$ is benzenediyl. In some embodiments, $X_1$ is a heteroarenediyl$_{(C\leq 12)}$ or a substituted heteroarenediyl$_{(C\leq 12)}$. In some embodiments, $X_1$ is heteroarenediyl$_{(C\leq 12)}$. In some embodiments, $X_1$ is pyridinediyl. In some embodiments, $Y_1$ is hydrogen. In some embodiments, $Y_1$ is an electron withdrawing group. In some embodiments, $Y_1$ is an electron withdrawing group selected from the group consisting of amino, cyano, halo, hydroxy, nitro, or a group of the formula: $—N(R_a)(R_b)(R_c)(R_d)^+$, wherein: $R_a$, $R_b$, $R_c$, and $R_d$ are each hydrogen, alkyl$_{(C\leq 8)}$, or substituted alkyl$_{(C\leq 8)}$; or $R_d$ is absent, wherein if $R_d$ is absent, the group is neutral.

In some embodiments, the capture moiety may comprise the group selected from:

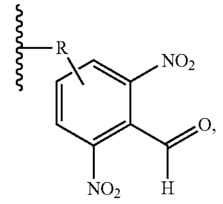

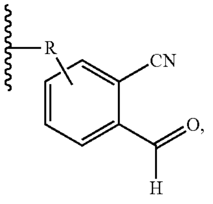

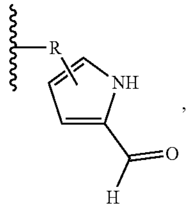

,

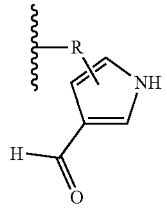

,

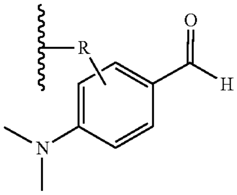

,

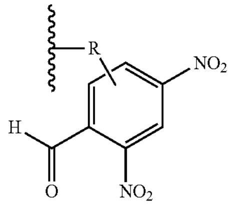

,

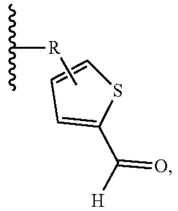

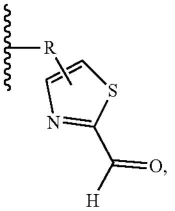

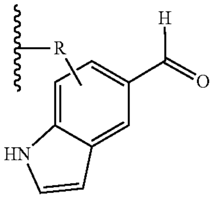

,

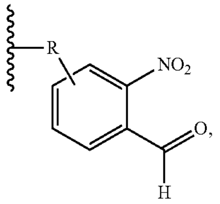

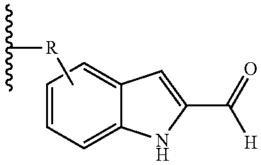

,

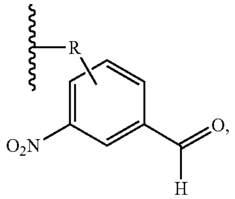

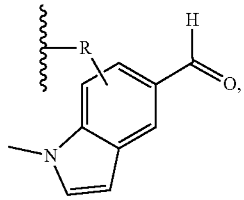

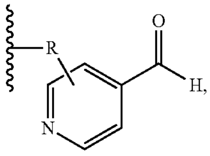

-continued
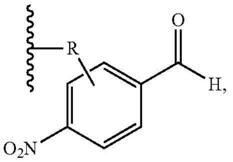
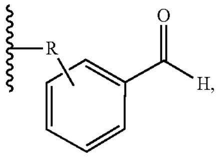
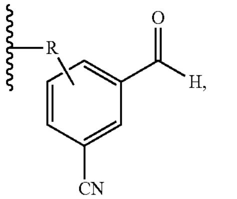
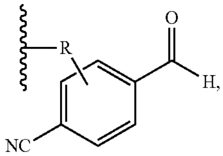
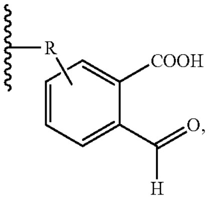
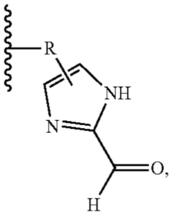
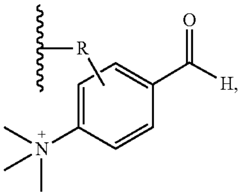
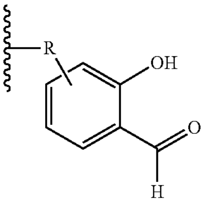
,
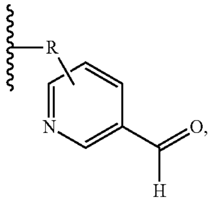
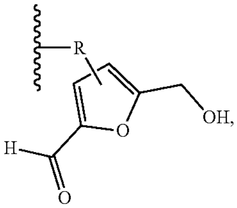
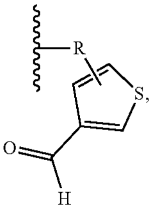
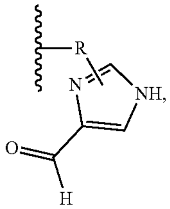
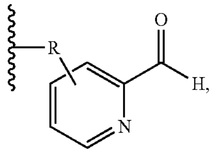
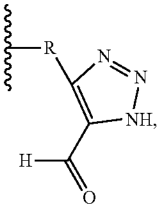
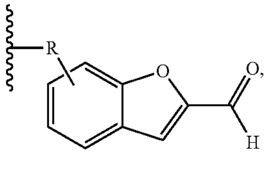
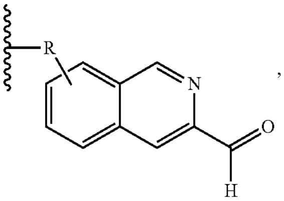
,
-continued
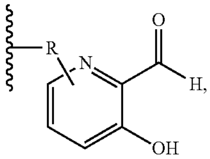
and
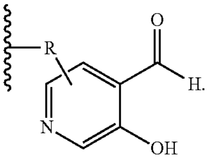
In some embodiments, the capture moiety may comprise the group selected from:
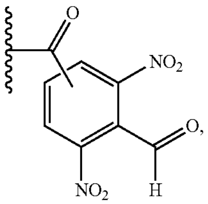
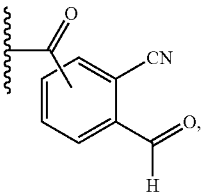
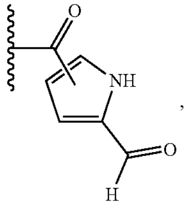
,
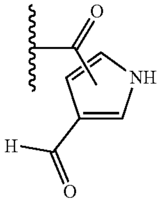
,
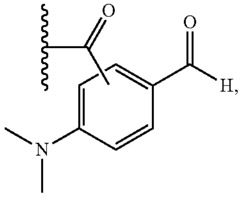
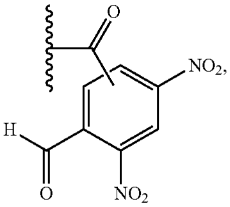
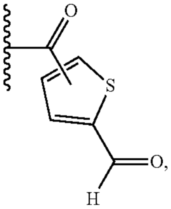
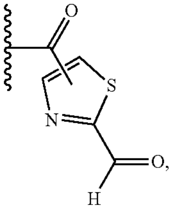
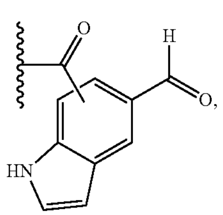
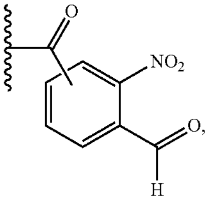
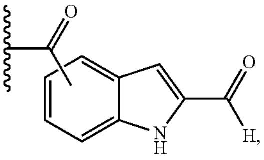
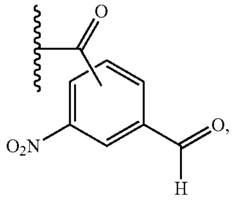

-continued

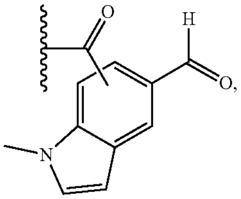

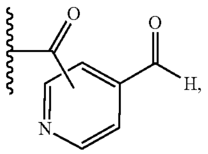

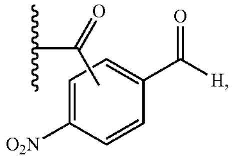

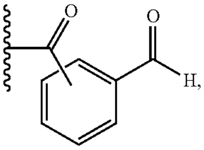

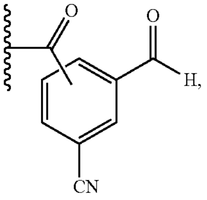

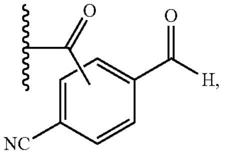

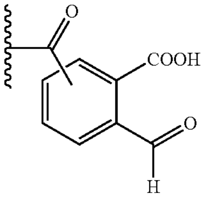

,

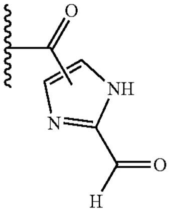

,

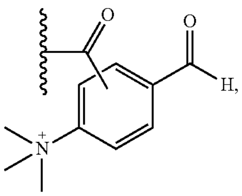

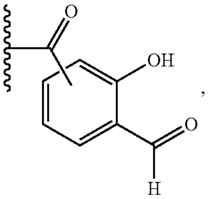

,

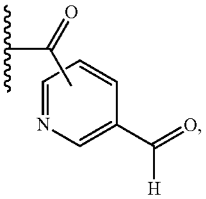

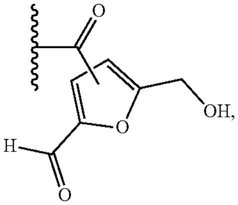

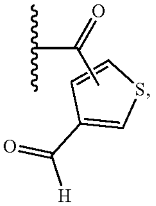

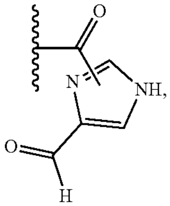

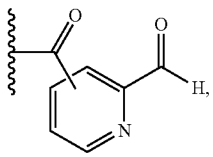

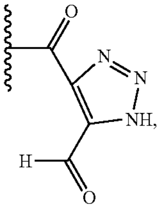

-continued

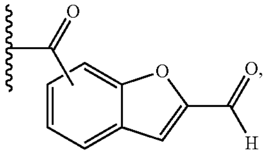

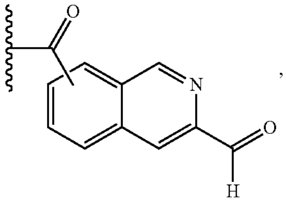

,

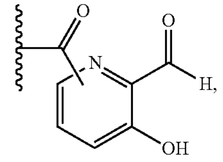

and

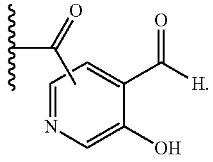

In some embodiments, the capture moiety may comprise:

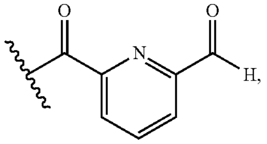

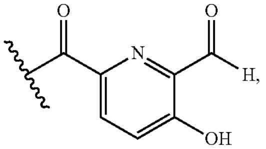

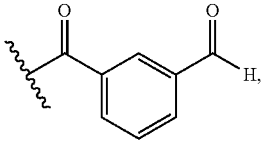

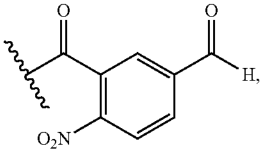

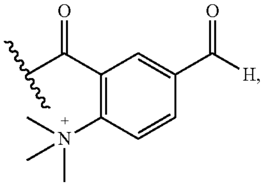

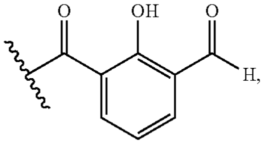

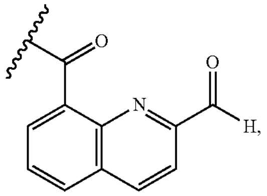

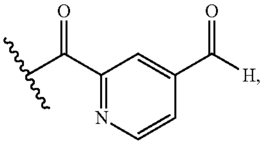

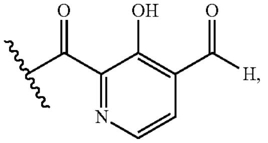

or

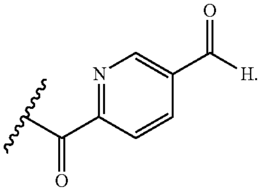

In some embodiments, the capture moiety may comprise

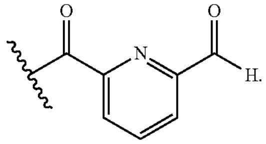

A support may comprise a plurality of barcodes, which plurality of barcodes comprises the barcode. A support may comprise a plurality of nucleic acid barcode sequences, which plurality of nucleic acid barcode sequences comprises the nucleic acid barcode sequence. The plurality of barcodes may have barcodes that are substantially identical. The plurality of nucleic acid barcode sequences may have barcode sequences that are substantially identical. The barcode may be a nucleic acid barcode sequence, an isobaric mass-tag (e.g., tandem mass tag (TMT)), amino acid sequences (e.g., arginine or poly arginine), ammonium, fluorophores, halogens (e.g., fluorine, chlorine, bromine, and iodine), or any combination thereof (e.g., oligonucleotide-peptide hybrids). The nucleic acid barcode sequence may be deoxyribonucleic acid (DNA), ribonucleic acid (RNA), a peptide nucleic acid (PNA), or any combination thereof. The nucleic acid barcode sequence may be an oligomer. The nucleic acid barcode sequence may be a polymer. The length of the nucleic acid barcode sequence may be at least 10, 20, 30, 40, 50, 60, 70, 80, 90, 100, 150, 200, 250, 300, 350, 400, 450, 500, 600, 700, 800, 900, 1,000, 10,000, or more nucleic acid bases. The length of the nucleic acid barcode sequence may be at most 10,000, 1,000, 900, 800, 700, 600, 500, 450, 400, 350, 300, 250, 200, 150, 100, 90, 80, 70, 60, 50, 40, 30, 20, 10, or less nucleic acid bases. The length of the nucleic acid barcode sequence may be from about 10 to about 10,000 nucleic acid bases. The length of the nucleic acid barcode sequence may be from about 10 to about 1,000 nucleic acid bases. The length of the nucleic acid barcode sequence may be from about 10 to about 100 nucleic acid bases. The amino acid barcode sequence may be an oligomer. The amino acid barcode sequence may be a polymer. The length of the amino acid barcode sequence may be at least 5, 10, 20, 30, 40, 50, 60, 70, 80, 90, 100, 150, 200, 250, 300, 350, 400, 450, 500, 600, 700, 800, 900, 1,000, 10,000, or more amino acid residues. The length of the amino acid barcode sequence may be at most 10,000, 1,000, 900, 800, 700, 600, 500, 450, 400, 350, 300, 250, 200, 150, 100, 90, 80, 70, 60, 50, 40, 30, 20, 10, 5, or less amino acid residues. The length of the amino acid barcode sequence may be from about 5 to about 10,000 amino acid residues. The length of the amino acid barcode sequence may be from about 5 to about 100 amino acid residues. The length of the amino acid barcode sequence may be from about 5 to about 20 amino acid residues. The isobaric mass-tag may enable identification and quantitation of proteins in different samples using tandem mass spectrometry (MS). The isobaric mass-tag may be a tandem mass tag (TMT). A tandem mass-tag may have a different ionization mass than another tandem mass-tag.

A cleavable unit may comprise functional groups, such as, for example, disulfides, A cleavable unit may be cleaved by, for example, enzymes, nucleophilic or basic reagents, reducing agents, photo-irradiation, electrophilic or acidic reagents, organometallic or metal reagents, oxidizing reagents, or combinations thereof. The cleavable group can be an acid cleavable aminomethyl group (e.g., rink-amide, Sieber, peptide amide linker (PAL)), hydroxymethyl (Wang-type), trityl or chlorotrityl, aryl-hydrazide linker. The cleavable group can be a metal cleavable group, such as, for example, an alloc linker, hydrazine cleavable group, or photo-labile cleavable group, such as, for example, nitrobenzyl based (e.g., 4-[4-(1-(Fmoc-amino)ethyl)-2-methoxy-5-nitrophenoxy]butanoic acid) or a carbonyl-based linker.

The cleavable unit may be cleaved with TFA.

The linker may comprise the building block for the barcode. The linker may comprise the building block for the nucleic acid barcode sequence. The building block for the barcode may comprise, for example, an amine (e.g., lysine), an azide (e.g., azidolysine), an alkyne (e.g., propargylglycine) or a thiol (e.g., cysteine). The building block for the nucleic acid barcode sequence may comprise, for example, an amine (e.g., lysine), an azide (e.g., azidolysine), an alkyne (e.g., propargylglycine) or a thiol (e.g., cysteine). A sequence of the barcode may be coupled to the building block for the barcode. A sequence for the nucleic acid barcode sequence may be coupled to the building block for the nucleic acid barcode sequence. A primer sequence for the nucleic acid barcode sequence may be coupled to the building block for the nucleic acid barcode sequence. The sequence may comprise a primer sequence. A primer sequence for the nucleic acid barcode sequence may be coupled to the building block for the nucleic acid barcode sequence. A primer sequence for the nucleic acid barcode sequence may be directly coupled to the building block for the nucleic acid barcode sequence. The nucleic acid barcode sequence may be coupled to the primer sequence.

The barcode may be combinatorially assembled. The nucleic acid barcode sequence may be combinatorially assembled. The barcode may be combinatorially assembled using a primer sequence coupled to the support. The nucleic acid barcode sequence may be combinatorially assembled using a primer sequence coupled to the support. The primer sequence may be indirectly coupled to the support. The primer sequence may be indirectly coupled to the support through the building block for the barcode. The primer sequence may be indirectly coupled to the support through the building block for the nucleic acid barcode sequence. The combinatorial assembly may be accomplished using split-pool cycles, strand extension on precoated oligonucleotide beads, or a combination thereof.

The probe may interact with the barcode. The barcode may be identified with a probe that interacts with the barcode to yield a signal or change thereof that is detected. A nucleic acid barcode sequence may be identified with a probe that interacts with the nucleic acid barcode sequence to yield a signal or change thereof that is detected. The probe may hybridize to the nucleic acid barcode sequence. The signal may be an electrochemical signal, optical signal, or any combination thereof. The optical signal may be a florescent signal, a bioluminescent signal, electrochemiluminescent signal, or any combination thereof. The probe may comprise one of an energy donor and an energy acceptor. The probe may comprise one of an energy donor and an energy acceptor, wherein the barcode may couple to the other of the energy donor and the energy acceptor. The probe may comprise one of an energy donor and an energy acceptor, wherein the nucleic acid barcode sequence may couple to the other of the energy donor and the energy acceptor. The probe may comprise one of an emitter and a quencher. The probe may comprise one of an emitter and a quencher, wherein the barcode may be coupled to the other of the emitter and the quencher. The probe may comprise one of an emitter and a quencher, wherein the nucleic acid barcode sequence may be coupled to the other of the emitter and the quencher. The probe may comprise one of an emitter and a quencher, wherein the barcode may be coupled to the other of the emitter and the quencher, and wherein the barcode may be identified upon a quenching of the optical signal. The probe may comprise one of an emitter and a quencher, wherein the nucleic acid barcode sequence may be coupled to the other of the emitter and the quencher, and wherein the nucleic acid barcode sequence may be identified upon a quenching of the optical signal. The probe may comprise one of an energy donor and an energy acceptor, wherein the barcode may couple to the other of the energy donor and the energy acceptor, and wherein the optical signal is generated by fluorescence resonance energy transfer (FRET). The probe may comprise one of an energy donor and an energy acceptor, wherein the nucleic acid barcode sequence may couple to the other of the energy donor and the energy acceptor, and wherein the optical signal is generated by fluorescence resonance energy transfer (FRET). The probe may comprise one of an energy donor and an energy acceptor, wherein the barcode may couple to the other of the energy donor and the energy acceptor, and wherein the optical signal is generated by bioluminescence resonance energy transfer (BRET). The probe may comprise one of an energy donor and an energy acceptor, wherein the nucleic acid barcode sequence may couple to the other of the energy donor and the energy acceptor, and wherein the optical signal is generated by bioluminescence resonance energy transfer (BRET). The probe may comprise one of an energy donor and an energy acceptor, wherein the barcode may couple to the other of the energy donor and the energy acceptor, and wherein the optical signal is generated by electrochemiluminescent resonance energy transfer (ECRET). The probe may comprise one of an energy donor and an energy acceptor, wherein the nucleic acid barcode sequence may couple to the other of the energy donor and the energy acceptor, and wherein the optical signal is generated by electrochemiluminescent resonance energy transfer (ECRET). The barcode may be identified with sequencing, such as, for example, nanopore sequencing, FRET, BRET, ECRET, fluorescent in-situ hybridization (FISH), DNA-PAINT, multi-barcode identification (e.g., MER-FISH), or any combination thereof. The nucleic acid barcode sequence may be identified with sequencing, such as, for example, nanopore sequencing, FRET, BRET, ECRET, fluorescent in-situ hybridization (FISH), DNA-PAINT, multi-barcode identification (e.g., MER-FISH), or any combination thereof.

In some embodiments, (c) may comprise providing at least one protein or peptide adjacent to an array. The protein or peptide may be immobilized to the assay. In some embodiments, (c) may comprise providing a plurality of proteins or a plurality of peptides adjacent to an array. In some embodiments, prior to sequencing, the at least one protein or peptide having coupled thereto the nucleic acid barcode sequence may be (a) provided adjacent to an array, (b) identified, and (c) removed from the at least one protein or peptide. In some embodiments, prior to sequencing, the plurality of proteins or plurality of peptides having coupled thereto the nucleic acid barcode sequence may be (a) provided adjacent to an array, (b) identified, and (c) removed from the plurality of proteins or peptides. In some embodiments, prior to (a), the peptide or protein may be labeled with at least one label. The labels may be optical labels. The optical labels may be fluorophores. The fluorophores may couple to select amino acids of the peptide or protein. The optical labels may be used for fluorosequencing the peptide or protein. The barcode may be removed from the at least one protein or peptide by cleaving the capture moiety, thereby producing at least one protein or peptide to be identified. The barcode may be removed from the plurality of proteins or peptides by cleaving the capture moiety, thereby producing a plurality of proteins or peptides to be identified. The nucleic acid barcode sequence may be removed from the at least one protein or peptide by cleaving the capture moiety, thereby producing at least one protein or peptide to be identified. The nucleic acid barcode sequence may be removed from the plurality of proteins or peptides by cleaving the capture moiety, thereby producing a plurality of proteins or peptides to be identified. The capture moiety may be cleaved with a reversing reagent or a releasing reagent. The releasing reagent may be a hydrazine, an oxime, a methoxylamine, ammonia, trifluoroacetic acid (TFA), or an aniline. The reversing reagent may be a hydrazine, an oxime, a methoxylamine, ammonia, or an aniline. The reversing reagent may be hydrazine. The releasing reagent may be TFA. The releasing reagent may be hydrazine and TFA. The reversing or releasing reagent may be applied multiple times. The releasing conditions may be a two-step process. The first step may comprise cleaving the cleavable unit, and the second step may comprise cleaving the imidazolinone adduct. The releasing conditions in the first step may comprise TFA, and the releasing conditions in the second step may comprise hydrazine. The releasing conditions may be a single-step process. The cleavable unit may be cleaved with TFA. The imidazolinone adduct may be cleaved with hydrazine.

Sequencing at least one protein or peptide may comprise (i) labeling at least a subset of amino acid residues of the at least one protein or peptide with labels, and (ii) sequentially detecting the labels to identify the at least one protein or peptide, or sequence thereof. Sequencing a plurality of proteins or peptides may comprise (i) labeling at least a subset of amino acid residues of the plurality of proteins or peptides with labels, and (ii) sequentially detecting the labels to identify the plurality of proteins or peptides, or sequences thereof. The labels may be optical labels. The optical labels may be fluorophores. The fluorophores may couple to select amino acids of at least one peptide or protein. The optical labels may be used for fluorosequencing the at least one peptide or protein. In some embodiments, prior to (ii), at least one peptide or protein having the labels may be removed or released from the support by cleaving the cleavable group. In some embodiments, subsequent to removing or releasing the at least one protein or peptide from the support, a location of at least one protein or peptide adjacent to the array may be identified. The protein or peptide may be immobilized to the assay. The location of at least 50%, 55%, 60%, 65%, 70%, 75%, 80%, 85%, 90%, 95%, 99%, or more proteins or peptides adjacent to the array are identified. The location of at least one protein or peptide adjacent to the array may be identified by microscopy. In some embodiments, prior to microscopy, at least one protein or peptide coupled thereto the barcode is spread over a glass slide. The at least one protein or peptide coupled thereto the barcode may comprise a solution. In some embodiments, prior to microscopy, at least one protein or peptide coupled thereto the nucleic acid barcode sequence is spread over a glass slide. The at least one protein or peptide coupled thereto the nucleic acid barcode sequence may comprise a solution. The solution may be diluted to a concentration of at most 1 M, 1 mM, 1 μM, 0.9 μM, 0.8 μM, 0.7 μM, 0.6 μM, 0.5 μM, 0.4 μM, 0.3 μM, 0.2 μM, 0.1 μM, 90 nM, 80 nM, 70 nM, 60 nM, 50 nM, 40 nM, 30 nM, 20 nM, 10 nM, 1 nM 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, 0.009 nM, 0.008 nM, 0.007 nM, 0.006 nM, 0.005 nM, 0.004 nM, 0.003 nM, 0.002 nM, 0.001 nM, 0.0001 nM, or less, or any range derivable therein. The solution may be diluted to a concentration from about 100 nM to about 0.0001 nM. The solution may be diluted to a concentration from about 10 nM to about 0.0001 nM. The solution may be diluted to a concentration from about 1 nM to about 0.0001 nM. The solution may be diluted to a concentration from about 0.1 nM to about 0.0001 nM. The solution may be diluted to a concentration from about 0.1 nM to about 0.001 nM. The identity of at least 50%, 55%, 60%, 65%, 70%, 75%, 80%, 85%, 90%, 95%, 99%, or ore proteins or peptides may be identified.

Sequencing the protein or peptide may be performed using a degradation reagent. Sequencing the protein or peptide may be performed by using a degradation reagent that cleaves the N-terminus of the protein or peptide. Sequencing the protein or peptide may be performed by using a degradation reagent that cleaves the C-terminus of the protein or peptide. The peptide or protein may be identified using, for example, SINGLE molecule fingerprinting, nanopore sequencing, single molecule sequencing (e.g., N-terminal affinity antibody sequencing), antibody on immobilized peptide or protein on resin, or any combination thereof. Single molecule sequencing can provide single molecule resolution.

In some embodiments. (a) comprises providing a droplet among a plurality of droplets, which droplet comprises the mixture. The mixture may comprise no more than the cell. The mixture may comprise no more than the plurality of cells. The cell may be lysed, thereby forming a lysed cell. The cell may be lysed, thereby forming a lysed cell, wherein the lysed cell releases or makes accessible a plurality of proteins or peptides of the cell, which plurality of proteins or peptides comprises the protein or peptide. The plurality of proteins or peptides of the cell may be digested, thereby forming another plurality of proteins or peptides. The plurality of proteins or peptides may be captured by a plurality of capture moieties coupled to the support.

In some embodiments. (a) comprises providing a well among a plurality of well, which well comprises the mixture. The mixture may comprise no more than the cell. The mixture may comprise no more than the plurality of cells. The cell may be lysed, thereby forming a lysed cell. The cell may be lysed, thereby forming a lysed cell, wherein the lysed cell releases or makes accessible a plurality of proteins or peptides of the cell, which plurality of proteins or peptides comprises the protein or peptide. The plurality of proteins or peptides of the cell may be digested, thereby forming another plurality of proteins or peptides. The plurality of proteins or peptides may be captured by a plurality of capture moieties coupled to the support.

In certain aspects, the disclosure provides a composition comprising a support having coupled thereto (i) a barcode and (ii) a capture moiety for capturing a protein or peptide, wherein the capture moiety is not an antibody. In other aspects, the disclosure provides a composition comprising a support having coupled thereto (i) a nucleic acid barcode sequence and (ii) a capture moiety for capturing a protein or peptide, wherein the capture moiety is not an antibody.

In certain aspects, the disclosure provides a composition comprising a support having coupled thereto (i) a barcode and (ii) a capture moiety comprising an aromatic or a heteroaromatic carboxaldehyde. In certain aspects, the disclosure provides a composition comprising a support having coupled thereto (i) a nucleic acid barcode sequence and (ii) a capture moiety comprising an aromatic or heteroaromatic carboxaldehyde. In certain aspects, the disclosure provides a composition comprising a support having coupled thereto (i) a nucleic acid barcode sequence and (ii) a capture moiety comprising 2-pyridinecarboxaldehyde or a derivative thereof.

The barcode may be coupled to the support through a linker. The nucleic acid barcode sequence may be coupled to the support through a linker. The linker may couple at least two molecules, or more. The linker may be coupled to at least three molecules, or more. The linker may include a cleavable unit and a building block for barcoding a nucleic acid sequence. The linker may be a homofunctional or a heterofunctional linker. The linker may be a cleavable linker, cross-linker, a bifunctional linker, a trifunctional linker, a multi-functional linker, or any combination thereof. The linker may include functional groups, such as, for example, amines, sulfhydryls, acids, alcohols, bromides, maleamides, succinimidyl esters (NHS), sulfosuccinimidyl esters, disulfides, azides, alkynes, isothiocyanates (ITC), or combinations thereof. The linker may include protected functional groups, such as, for example, Boc, Fmoc, alkyl ester, Cbz, or combinations thereof. The nucleic acid barcode sequence may be directly coupled to said support.

The linker may comprise a conjugating group (e.g., oxo) that is covalently bound to a bead. The linker may provide a spacer between any component of the probe (e.g., the capture moiety, the solid support, the building block for barcode sequencing, the barcode, or the cleavable unit). The linker may provide a spacer between the solid support and the capture moiety. The linker may be, for example, a mono or polymeric form of an alkane, alkene, heterocycle, ethylene glycol, amide, or peptide (e.g., poly-arginine). The linker may comprise a cleavable group, such as, for example, a rink linker, photocleavable functional group, or a base cleavable functional group. The linker may comprise at least one internal functional group to enhance properties for downstream analysis (e.g., at least one charged functional group built in the linker (e.g., arginine to increase ionization), a nucleic acid barcode (e.g., for single molecule sequencing), or (c) amino acids with isobaric labels (e.g., for mass spectrometry quantification).

The support may be a solid support or a semi-solid support. The solid support or semi-solid support may be a bead. The bead may be a gel bead. The bead may be a polymer bead. The support may be a resin. Non-limiting supports may comprise, for example, agarose, sepharose, polystyrene, polyethylene glycol (PEG), or any combination thereof. The support may be a polystyrene bead. The support may include functional groups, such as, for example, amines, sulfhydryls, acids, alcohols, bromides, maleamides, succinimidyl esters (NHS), sulfosuccinimidyl esters, disulfides, azides, alkynes, isothiocyanates (ITC), or combinations thereof. The support may be a PEGA resin. The support may be an amino PEGA resin. The support may comprise an amine group. The support may include protected functional groups, such as, for example, Boc, Fmoc, alkyl ester, Cbz, or combinations thereof. The bead may contain a metal core. The bead may be a polymer magnetic bead. The polymer magnetic bead may comprise a metal-oxide. The support may comprise at least one iron oxide core.

The support may have coupled thereto a nucleic acid barcode sequence. The support may have directly coupled thereto a nucleic acid barcode sequence. The support may have coupled thereto a plurality of nucleic acid barcode sequences. The support may have directly coupled thereto a plurality of nucleic acid barcode sequences. The support may be coupled to a pendant group. The support may be coupled to a plurality of pendant groups. The support may be coupled to a nucleic acid barcode sequence and to a pendant group. The support may be directly coupled to a nucleic acid barcode sequence and to a pendant group. The support may be coupled to a nucleic acid barcode sequence and to a plurality of pendant groups. The support may be directly coupled to a nucleic acid barcode sequence and to a plurality of pendant groups. The support may be coupled to a plurality of nucleic acid barcode sequences and to a plurality of pendant groups. The support may be directly coupled to a plurality of nucleic acid barcode sequences and to a plurality of pendant groups.

A pendant group may comprise at least one capture moiety. A pendant group may comprise at least one cleavable unit. A pendant group may comprise at least one nucleic acid barcode sequence. A pendant group may comprise at least one building block for the nucleic acid barcode sequence(s). A pendant group may comprise at least one capture moiety and at least one cleavable unit. A pendant group may comprise at least one capture moiety and at least one nucleic acid barcode sequence. A pendant may comprise at least one capture moiety and at least one building block for the nucleic acid barcode sequence(s). A pendant group may comprise at least one cleavable unit and at least one nucleic acid barcode sequence. A pendant group may comprise at least one cleavable unit and at least one building block for the nucleic acid barcode sequence(s). A pendant group may comprise at least one nucleic acid barcode sequence and at least one building block for the nucleic acid barcode sequence(s). A pendant group may comprise at least one capture moiety, at least one cleavable unit, and at least one nucleic acid barcode sequence. A pendant group may comprise at least one capture moiety, at least one nucleic acid barcode sequence, and at least one building block for the nucleic acid barcode sequence(s). A pendant group may comprise at least one cleavable unit, at least one nucleic acid barcode sequence, and at least one building block for the nucleic acid barcode sequence(s). A pendant group may comprise at least one capture moiety, at least one cleavable unit, and at least one building block for the nucleic acid barcode sequence(s). A pendant group may comprise at least one capture moiety, at least one cleavable unit, at least one nucleic acid barcode sequence, and at least one building block for the nucleic acid barcode sequence(s).

The support may be coupled to at least one pendant. The support may be coupled to a plurality of pendants. The support may be coupled to a plurality of pendants, wherein pendant groups of said plurality of pendants may be substantially identical. The support may be coupled to at least one nucleic acid barcode sequence. The support may be coupled to at least one pendant and at least one nucleic acid barcode sequence. The support may be coupled to a first position of the cleavable unit and the capture moiety may be coupled to a second position of the cleavable unit. A first position of the support may be coupled at least one nucleic acid barcode sequence, and a second position of the support may be coupled to a first position of the cleavable unit and the capture moiety may be coupled to a second position of the cleavable unit.

A support may be coupled to at least one pendant. The support may be coupled to a plurality of pendants. The support may be coupled to a plurality of pendants, wherein pendant groups of said plurality of pendants may be substantially identical. A support may comprise at least one pendant group comprising at least one capture moiety and at least one nucleic acid barcode sequence. A support may comprise at least one pendant group comprising at least one capture moiety and at least one nucleic acid barcode sequence, and wherein the at least one pendant group and the at least one nucleic acid barcode sequence are separately coupled to said support. The support may be coupled to at least one cleavable unit. The support may be coupled to at least one cleavable unit, wherein the cleavable unit is coupled to at least one building block for barcoding. The support may be coupled to at least one cleavable unit, wherein the cleavable unit is coupled to at least one building block for barcoding, wherein the building block for barcoding is coupled to at least one capture moiety. The support may be coupled to at least one cleavable unit, wherein the cleavable unit is coupled to at least one building block for barcoding, wherein the building block for barcoding is coupled to at least one nucleic acid barcode sequence and at least one capture moiety. The support may be coupled to (a) at a first position of at least one cleavable unit, (b) a first position of at least one building block for barcoding may be coupled to a second position of the at least one cleavable unit, (c) at least one capture moiety may be coupled to a second position of the at least one building block for barcoding, and (d) at least one nucleic acid barcode sequence may be coupled to a third position of the at least one building block for barcoding.

A support may be coupled to at least one pendant. The support may be coupled to a plurality of pendants. The support may be coupled to a plurality of pendants, wherein pendant groups of said plurality of pendants may be substantially identical. The plurality of pendant groups may comprise at least two identical pendant groups. The plurality of pendant groups may comprise at least two identical pendant groups. The plurality of pendant groups may comprise at least 10 identical pendant groups. The plurality of pendant groups may comprise at least 100 identical pendant groups. The plurality of pendant groups may comprise at least 1000 identical pendant groups. The plurality of pendant groups may comprise at least 10000 identical pendant groups. The plurality of pendant groups may comprise at least $10^5$ identical pendant groups. The plurality of pendant groups may comprise at least $10^{10}$ identical pendant groups. The plurality of pendant groups may comprise at least $10^{12}$ identical pendant groups. The plurality of pendant groups may comprise at least $10^{15}$ identical pendant groups.

A capture moiety may react with at least one peptide or protein. A capture moiety may react with the N-terminus of at least one peptide or protein. A capture moiety may react with the C-terminus of at least one peptide or protein. A capture moiety may react with one peptide or protein. A capture moiety may react with the N-terminus of one peptide or protein. A capture moiety may react with the C-terminus of one peptide or protein. Each peptide or protein of a cell may be captured by a plurality of capture moieties. The support may further comprise a capture moiety that can capture a molecule that is not a peptide or protein. The support may further comprise a capture moiety that can capture a nucleic acid molecule. The support may further comprise a capture moiety that can capture a ribonucleic acid molecule. A capture moiety may react with at least one nucleic acid molecule. A capture moiety may react with at least one ribonucleic acid (RNA) molecule. The capture moiety may capture RNA by primer extension. The captured RNA may be amplified.

A capture moiety may not comprise an antibody. A capture moiety may comprise an aldehyde. A capture moiety may comprise an aldehyde protecting group. The aldehyde protecting group may be an acetal. The aldehyde protecting group may be a 1,3-dioxane or a 1,3-dioxolane. A capture moiety may comprise formula (I):

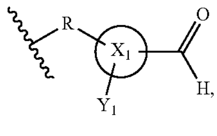

wherein $X_1$ is substituted or unsubstituted arenediyl$_{(C\leq 12)}$ or substituted or unsubstituted heteroarenediyl$_{(C\leq 12)}$; $Y_1$ is hydrogen or an electron withdrawing group; and R is a linker that is coupled to the solid support. The linker may comprise a monomer or a polymer. The linker may comprise a polypeptide, a polyethylene glycol, a polyamide, a heterocycle, or any combination thereof. The linker may comprise at least one oxo.

A capture moiety may comprise 2-pyridinecarboxaldehyde or a derivative thereof. A capture moiety may comprise formula (Ia):

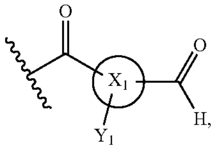

wherein $X_1$ is arenediyl$_{(C\leq12)}$, heteroarenediyl$_{(C\leq12)}$, or a substituted version of either of these groups; $Y_1$ is hydrogen or an electron withdrawing group; wherein said capture moiety is attached to said cleavable unit at the open valence of the carbonyl group. In some embodiments, $X_1$ is arenediyl$_{(C\leq12)}$ or a substituted arenediyl$_{(C\leq12)}$. In some embodiments, $X_1$ is arenediyl$_{(C\leq12)}$. In some embodiments, $X_1$ is benzenediyl. In some embodiments, $X_1$ is a heteroarenediyl$_{(C\leq12)}$ or a substituted heteroarenediyl$_{(C\leq12)}$. In some embodiments, $X_1$ is heteroarenediyl$_{(C\leq12)}$. In some embodiments, $X_1$ is pyridinediyl. In some embodiments, $Y_1$ is hydrogen. In some embodiments, $Y_1$ is an electron withdrawing group. In some embodiments, $Y_1$ is an electron withdrawing group selected from the group consisting of amino, cyano, halo, hydroxy, nitro, or a group of the formula: —$N(R_a)(R_b)(R_c)(R_d)^+$, wherein: $R_a$, $R_b$, $R_c$, and $R_d$ are each hydrogen, alkyl$_{(C\leq8)}$, or substituted alkyl$_{(C\leq8)}$; or $R_d$ is absent, wherein when $R_d$ is absent, the group is neutral.

In some embodiments, the capture moiety may comprise the group selected from:

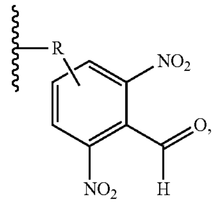
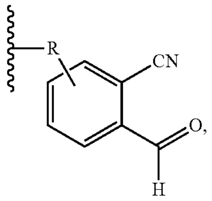

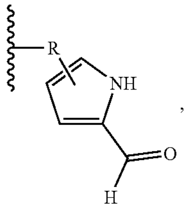
,
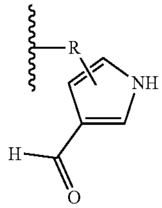
,

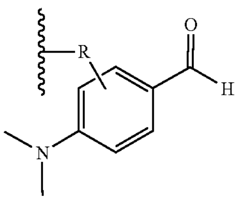
,
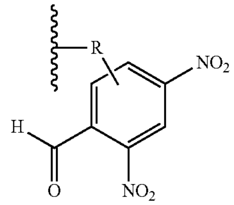
,

-continued

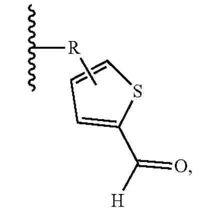
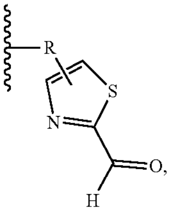

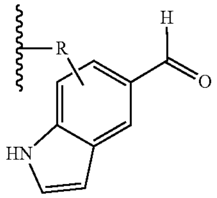
,
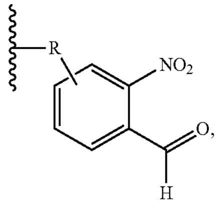

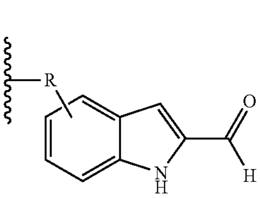
,
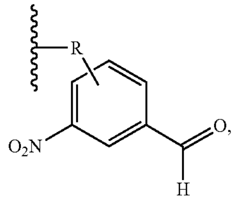

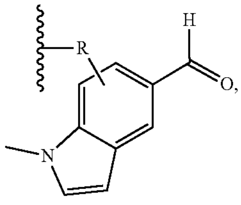
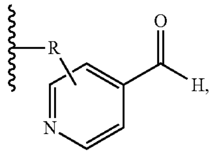

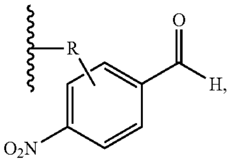
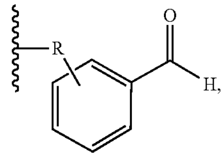

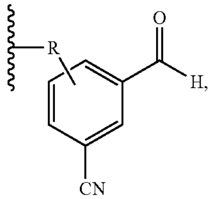
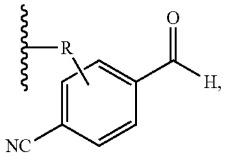

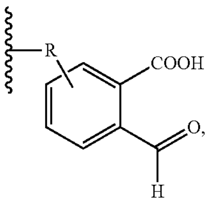
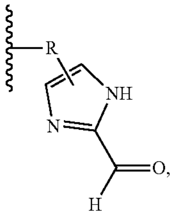

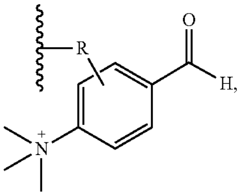
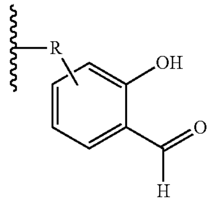
,

-continued
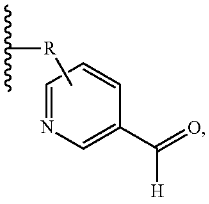 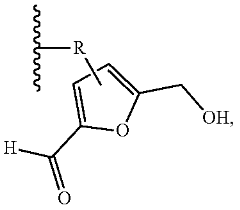
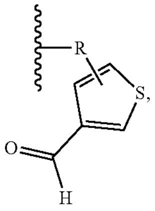 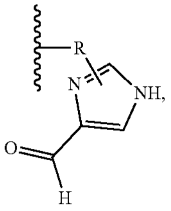
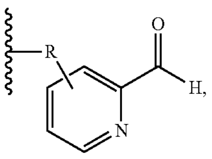 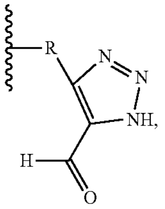
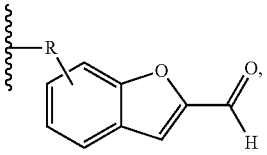 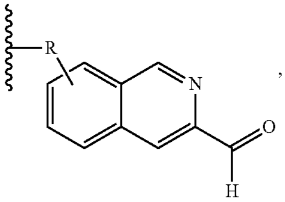 ,
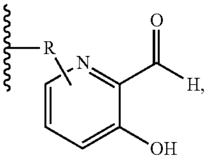 and 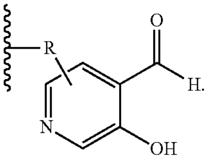
In some embodiments, the capture moiety may comprise the group selected from:
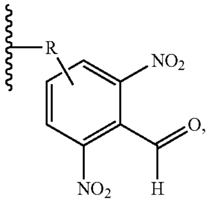 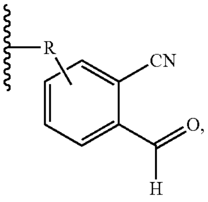
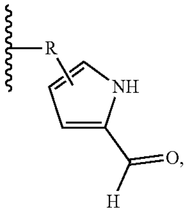 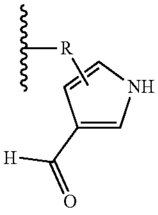 ,
-continued
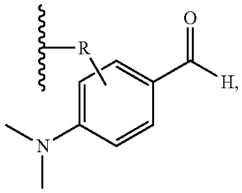 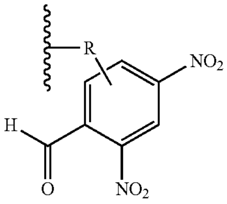 ,
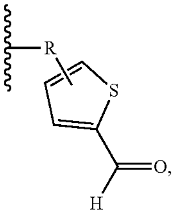 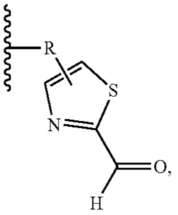
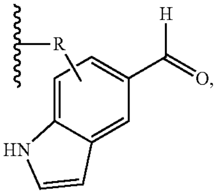 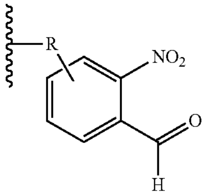 ,
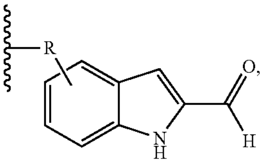 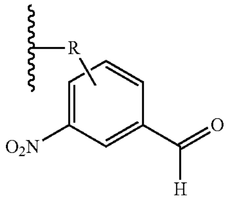 ,
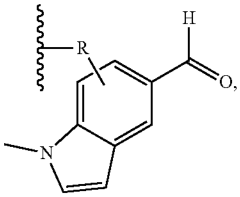 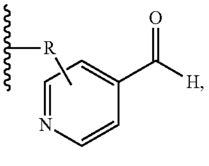
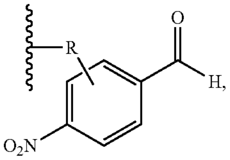 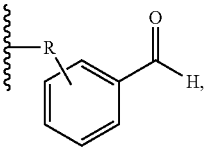
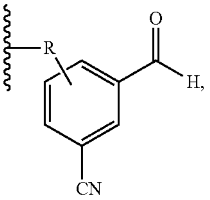 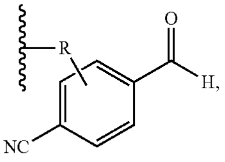
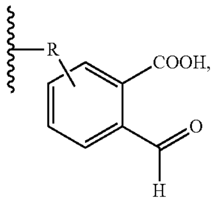 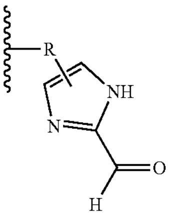 , -continued

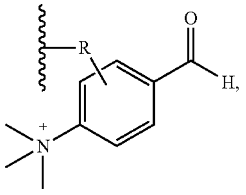
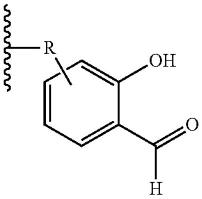
,

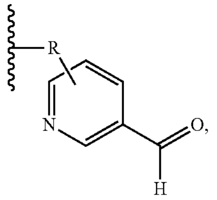
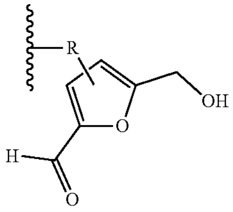
,

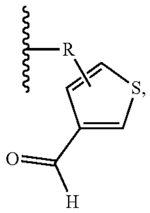
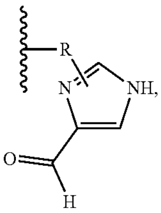
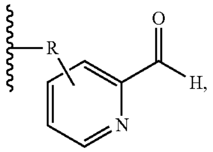

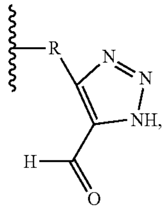
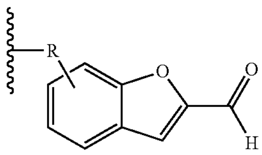
,

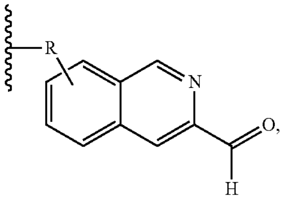
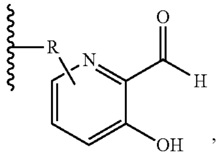
, and

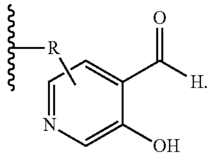

In some embodiments, R is a linker. In some embodiments, the linker is a monomer or a polymer. In some embodiments, the linker comprises a polypeptide, a polyethylene glycol, a polyamide, a heterocycle, or any combination thereof. In some embodiments, the linker comprises at least one oxo.

In some embodiments, the capture moiety may comprise the group selected from:

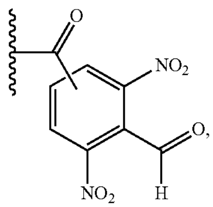
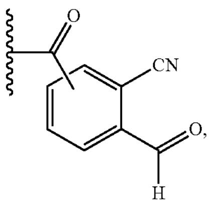

-continued

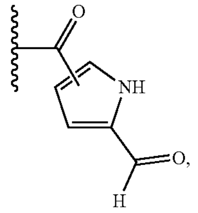
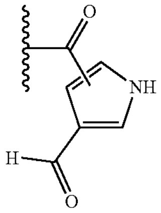
,

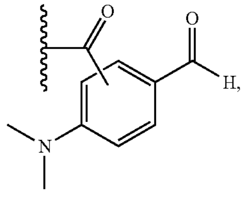
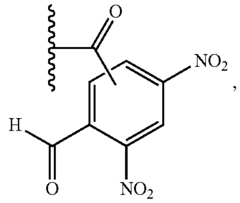
,

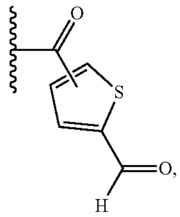
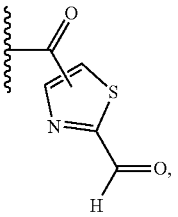

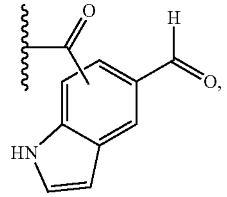
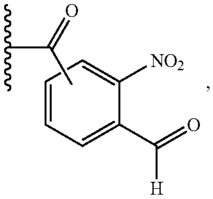
,

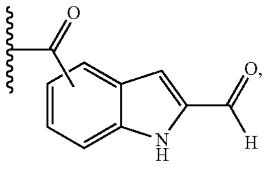
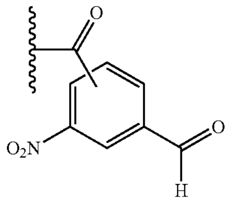
,

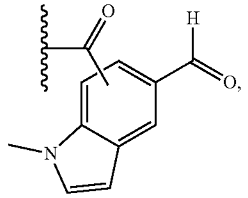
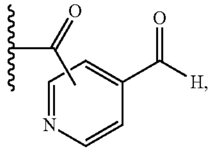

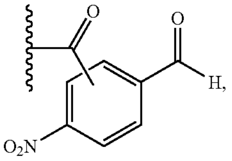
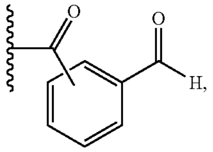

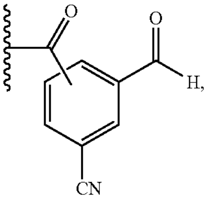
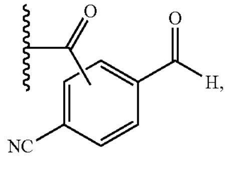

-continued

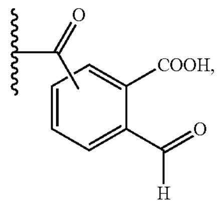
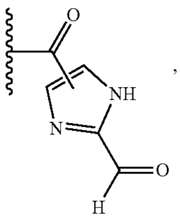
,

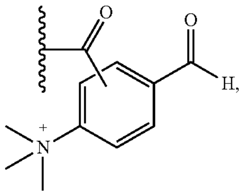
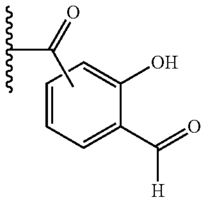
,

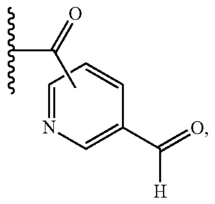
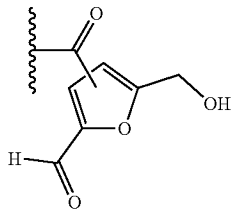
,

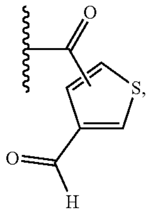
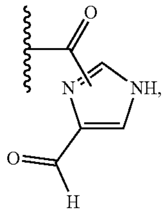
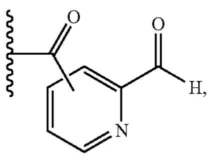

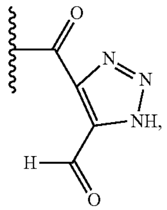
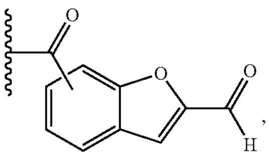
,

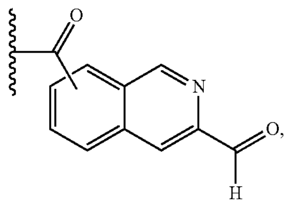
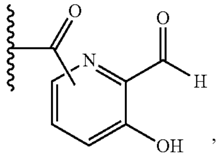
, and

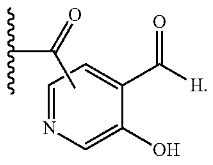

In some embodiments, the capture moiety may comprise the group selected from:

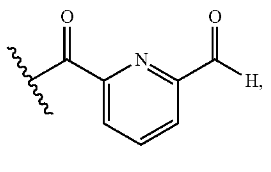
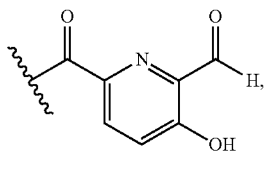

-continued

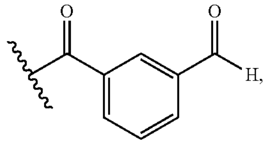
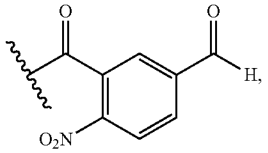

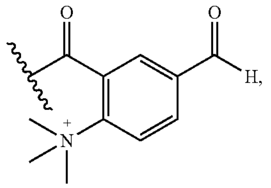
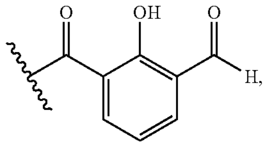

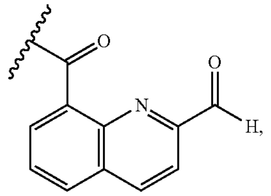
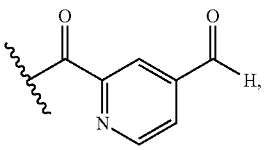

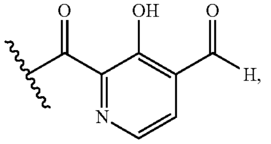
or
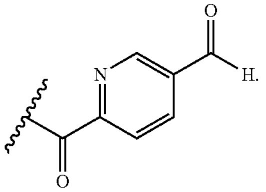

In some embodiments, the capture moiety may comprise

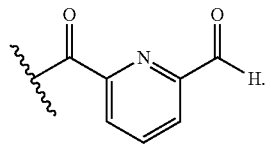

A support may comprise a plurality of nucleic acid barcode sequences, which plurality of nucleic acid barcode sequences comprises the nucleic acid barcode sequence. The plurality of nucleic acid barcode sequence may have barcode sequences that are substantially identical. The nucleic acid barcode sequence may be deoxyribonucleic acid (DNA), ribonucleic acid (RNA), a peptide nucleic acid (PNA), or any combination thereof. The nucleic acid barcode sequence may be an oligomer. The nucleic acid barcode sequence may be a polymer. The length of the nucleic acid barcode sequence may be at least 10, 20, 30, 40, 50, 60, 70, 80, 90, 100, 150, 200, 250, 300, 350, 400, 450, 500, 600, 700, 800, 900, 1,000, 10,000, or more nucleic acid bases. The length of the nucleic acid barcode sequence may be at most 10,000, 1,000, 900, 800, 700, 600, 500, 450, 400, 350, 300, 250, 200, 150, 100, 90, 80, 70, 60, 50, 40, 30, 20, 10, or less nucleic acid bases. The length of the nucleic acid barcode sequence may be from about 10 to about 10,000 nucleic acid bases. The length of the nucleic acid barcode sequence may be from about 10 to about 1,000 nucleic acid bases. The length of the nucleic acid barcode sequence may be from about 10 to about 100 nucleic acid bases.

A cleavable unit may comprise functional groups, such as, for example, disulfides, A cleavable unit may be cleaved by, for example, enzymes, nucleophilic or basic reagents, reducing agents, photo-irradiation, electrophilic or acidic reagents, organometallic or metal reagents, oxidizing reagents, or combinations thereof. The cleavable group can be an acid cleavable aminomethyl group (e.g., rink-amide, Sieber, peptide amide linker (PAL)), hydroxymethyl (Wang-type), trityl or chlorotrityl, aryl-hydrazide linker. The cleavable group can be a metal cleavable group, such as, for example, an alloc linker, hydrazine cleavable group, or photo-labile cleavable group, such as, for example, nitrobenzyl based (e.g., 4-[4-(1-(Fmoc-amino)ethyl)-2-methoxy-5-nitrophenoxy]butanoic acid), an ether-based linker, or a carbonyl based linker.

The linker may comprise the building block for the nucleic acid barcode sequence. The building block for the nucleic acid barcode sequence may comprise, for example, an amine (e.g., lysine), an azide (e.g., azidolysine), an alkyne (e.g., propargylglycine) or a thiol (e.g., cysteine). A sequence for the nucleic acid barcode sequence may be coupled to the building block for the nucleic acid barcode sequence. A primer sequence for the nucleic acid barcode sequence may be coupled to the building block for the nucleic acid barcode sequence. The sequence may comprise a primer sequence. A primer sequence for the nucleic acid barcode sequence may be coupled to the building block for the nucleic acid barcode sequence. A primer sequence for the nucleic acid barcode sequence may be directly coupled to the building block for the nucleic acid barcode sequence. The nucleic acid barcode sequence may be coupled to the primer sequence. The nucleic acid barcode sequence may be combinatorially assembled. The nucleic acid barcode sequence may be combinatorially assembled using a primer sequence coupled to the support. The primer sequence may be indirectly coupled to the support. The primer sequence may be indirectly coupled to the support through the building block for the nucleic acid barcode sequence. The combinatorial assembly may be accomplished using split-pool cycles, strand extension on precoated oligonucleotide beads, or a combination thereof.

In certain aspect, the disclosure provides a method of performing spatial proteomics comprising: (a) introducing a plurality of supports to a tissue comprising a plurality of proteins or peptides, wherein a single support of the plurality of supports contacts an area of the tissue, wherein the single support of the plurality of supports comprises a unique barcode and a capture moiety; (b) using the capture moiety to capture a protein or peptide of the plurality of proteins or peptides; (c) using the unique barcode to identify a location of the tissue from which the protein or peptide was derived; (d) determining a sequence of the protein or peptide; and associating the location identified in (c) with the sequence determined in (d).

The tissue may be from a biological sample. The biological sample may be derived from any organism. The biological sample may be derived from any organ of an organism. The biological sample may include, for example, tissue derived from the brain, heart, lung, respiratory system, skin, integumentary system, breast, eye, bone, gastrointestinal system, spine, musculoskeletal system, urinary system, renal system, reproductive system, sinus tract, pancreas, liver, gall bladder, lymphatic system, nervous system, circulatory system, endocrine system, or any combination thereof. The tissue may comprise a plurality of cells. The tissue or cell may be modified with cross-linkers. The tissue or cells may be expanded, such as described in expansion microscopy.

The support may be coupled directly to a glass slide. The support may not comprise a nucleic acid barcode sequence. The support may comprise a cleavable group. The tissue, or the cells derived thereof, may be contacted with the glass slide comprising the support. A plurality of peptides or proteins derived from the tissue, or the cells derived thereof, may be coupled a capture moiety coupled to the support. The cells derived from the tissue may be lysed. The cells derived from the tissue may be lysed, and the proteins or peptides derived from the cells may be digested. The capture moiety may comprise a molecule that can capture the N-terminus of a peptide or protein. The capture moiety may comprise a molecule that can capture the C-terminus of a peptide or protein. The capture moiety may comprise a molecule that can capture internal amino acid, such as, for example cysteine or lysine, of a peptide or protein. The captured peptide(s), protein(s), or combinations thereof may be captured by a capture moiety or a plurality of capture moieties. The captured peptide(s), protein(s), or a combination thereof may be immobilized to the support coupled to the glass slide. The peptides or proteins immobilized to the support may be labeled. The peptides or proteins may be labeled with molecules that provide a measurable signal. The peptides or proteins may be labeled with optical labels. The optical labels may be fluorescent labels. The optical labels may be fluorophores. The captured and labeled peptide(s), protein(s), or combinations thereof may be identified on the glass slide. The identification may be done by microscopy. The captured and labeled peptide(s), protein(s), or combinations thereof may be sequenced on the glass slide. The captured and labeled peptide(s), protein(s), or combinations thereof may be cleaved from the glass slide by cleaving the cleavable group. The cleaved, captured, and labeled peptide(s), protein(s), or combinations thereof may be sequenced. The peptide(s), protein(s), or combinations thereof may be sequenced using fluorosequencing.

In certain aspects, the disclosure provides a method of storing or stabilizing a plurality of peptides, proteins, or combinations thereof, comprising using a plurality of supports comprising a plurality of capture moieties to capture the peptides, proteins, or combinations thereof, wherein a capture moiety of the plurality of capture moieties (i) is not an antibody or (ii) comprises 2-pyridinecarboxaldehyde or a derivative thereof. A support of said plurality of supports may comprise a unique nucleic acid barcode sequence. In some embodiments, the method further comprises storing the plurality of peptides, proteins, or combinations thereof captured with the plurality of capture moieties. In some embodiments, the method further comprises washing the plurality of peptides, proteins, or combinations thereof captured with the plurality of capture moieties, thereby removing uncaptured molecules.

In certain aspects, the disclosure provides a method for generating a nucleic acid barcode sequence coupled to a support, comprising: (a) providing said support having coupled thereto a capture moiety configured to capture a protein or peptide and a nucleic acid segment; and (b) combinatorially assembling said nucleic acid barcode sequence to said nucleic acid segment. The combinatorially assembling may comprise subjecting the nucleic acid segment or derivative thereof to one or more split-pool cycles.

The support may be a solid support or a semi-solid support. The solid support or semi-solid support may be a bead. The bead may be a gel bead. The bead may be a polymer bead. The support may be a resin. Non-limiting supports may comprise, for example, agarose, sepharose, polystyrene, polyethylene glycol (PEG), or any combination thereof. The support may be a polystyrene bead. The support may include functional groups, such as, for example, amines, sulfhydryls, acids, alcohols, bromides, maleamides, succinimidyl esters (NHS), sulfosuccinimidyl esters, disulfides, azides, alkynes, isothiocyanates (ITC), or combinations thereof. The support may be a PEGA resin. The support may be an amino PEGA resin. The support may comprise an amine group. The support may include protected functional groups, such as, for example, Boc, Fmoc, alkyl ester, Cbz, or combinations thereof. The bead may contain a metal core. The bead may be a polymer magnetic bead. The polymer magnetic bead may comprise a metal-oxide. The support may comprise at least one iron oxide core.

The support may have coupled thereto a nucleic acid barcode sequence. The support may have directly coupled thereto a nucleic acid barcode sequence. The support may have coupled thereto a plurality of nucleic acid barcode sequences. The support may have directly coupled thereto a plurality of nucleic acid barcode sequence. The support may be coupled to a pendant group. The support may be coupled to a plurality of pendant groups. The support may be coupled to a nucleic acid barcode sequence and to a pendant group. The support may be directly coupled to a nucleic acid barcode sequence and to a pendant group. The support may be coupled to a nucleic acid barcode sequence and to a plurality of pendant groups. The support may be directly coupled to a nucleic acid barcode sequence and to a plurality of pendant groups. The support may be coupled to a plurality of nucleic acid barcode sequences and to a plurality of pendant groups. The support may be directly coupled to a plurality of nucleic acid barcode sequences and to a plurality of pendant groups.

A pendant group may comprise at least one capture moiety. A pendant group may comprise at least one cleavable unit. A pendant group may comprise at least one nucleic acid barcode sequence. A pendant group may comprise at least one building block for the nucleic acid barcode sequence(s). A pendant group may comprise at least one capture moiety and at least one cleavable unit. A pendant group may comprise at least one capture moiety and at least one nucleic acid barcode sequence. A pendant may comprise at least one capture moiety and at least one building block for the nucleic acid barcode sequence(s). A pendant group may comprise at least one cleavable unit and at least one nucleic acid barcode sequence. A pendant group may comprise at least one cleavable unit and at least one building block for the nucleic acid barcode sequence(s). A pendant group may comprise at least one nucleic acid barcode sequence and at least one building block for the nucleic acid barcode sequence(s). A pendant group may comprise at least one capture moiety, at least one cleavable unit, and at least one nucleic acid barcode sequence. A pendant group may comprise at least one capture moiety, at least one nucleic acid barcode sequence, and at least one building block for the nucleic acid barcode sequence(s). A pendant group may comprise at least one cleavable unit, at least one nucleic acid barcode sequence, and at least one building block for the nucleic acid barcode sequence(s). A pendant group may comprise at least one capture moiety, at least one cleavable unit, and at least one building block for the nucleic acid barcode sequence(s). A pendant group may comprise at least one capture moiety, at least one cleavable unit, at least one nucleic acid barcode sequence, and at least one building block for the nucleic acid barcode sequence(s).

The support may be coupled to at least one pendant. The support may be coupled to a plurality of pendants. The support may be coupled to a plurality of pendants, wherein pendant groups of said plurality of pendants may be substantially identical. The support may be coupled to at least one nucleic acid barcode sequence. The support may be coupled to at least one pendant and at least one nucleic acid barcode sequence. The support may be coupled to a first position of the cleavable unit and the capture moiety may be coupled to a second position of the cleavable unit. A first position of the support may be coupled at least one nucleic acid barcode sequence, and a second position of the support may be coupled to a first position of the cleavable unit and the capture moiety may be coupled to a second position of the cleavable unit.

A support may be coupled to at least one pendant. The support may be coupled to a plurality of pendants. The support may be coupled to a plurality of pendants, wherein pendant groups of said plurality of pendants may be substantially identical. A support may comprise at least one pendant group comprising at least one capture moiety and at least one nucleic acid barcode sequence. A support may comprise at least one pendant group comprising at least one capture moiety and at least one nucleic acid barcode sequence, and wherein the at least one pendant group and the at least one nucleic acid barcode sequence are separately coupled to said support. The support may be coupled to at least one cleavable unit. The support may be coupled to at least one cleavable unit, wherein the cleavable unit is coupled to at least one building block for barcoding. The support may be coupled to at least one cleavable unit, wherein the cleavable unit is coupled to at least one building block for barcoding, wherein the building block for barcoding is coupled to at least one capture moiety. The support may be coupled to at least one cleavable unit, wherein the cleavable unit is coupled to at least one building block for barcoding, wherein the building block for barcoding is coupled to at least one nucleic acid barcode sequence and at least one capture moiety. The support may be coupled to (a) at a first position of at least one cleavable unit, (b) a first position of at least one building block for barcoding may be coupled to a second position of the at least one cleavable unit, (c) at least one capture moiety may be coupled to a second position of the at least one building block for barcoding, and (d) at least one nucleic acid barcode sequence may be coupled to a third position of the at least one building block for barcoding.

A support may be coupled to at least one pendant. The support may be coupled to a plurality of pendants. The support may be coupled to a plurality of pendants, wherein pendant groups of said plurality of pendants may be substantially identical. The plurality of pendant groups may comprise at least two identical pendant groups. The plurality of pendant groups may comprise at least two identical pendant groups. The plurality of pendant groups may comprise at least 10 identical pendant groups. The plurality of pendant groups may comprise at least 100 identical pendant groups. The plurality of pendant groups may comprise at least 1000 identical pendant groups. The plurality of pendant groups may comprise at least 10000 identical pendant groups. The plurality of pendant groups may comprise at least $10^5$ identical pendant groups. The plurality of pendant groups may comprise at least $10^{10}$ identical pendant groups. The plurality of pendant groups may comprise at least $10^{12}$ identical pendant groups. The plurality of pendant groups may comprise at least $10^{15}$ identical pendant groups.

A capture moiety may react with at least one peptide or protein. A capture moiety may react with the N-terminus of at least one peptide or protein. A capture moiety may react with the C-terminus of at least one peptide or protein. A capture moiety may react with one peptide or protein. A capture moiety may react with the N-terminus of one peptide or protein. A capture moiety may react with the C-terminus of one peptide or protein. Each peptide or protein of a cell may be captured by a plurality of capture moieties. The support may further comprise a capture moiety that can capture a molecule that is not a peptide or protein. The support may further comprise a capture moiety that can capture a nucleic acid molecule. The support may further comprise a capture moiety that can capture a ribonucleic acid molecule. A capture moiety may react with at least one nucleic acid molecule. A capture moiety may react with at least one ribonucleic acid (RNA) molecule. The capture moiety may capture RNA by primer extension. The captured RNA may be amplified.

A capture moiety may not comprise an antibody. A capture moiety may comprise 2-pyridinecarboxaldehyde or a derivative thereof. A capture moiety may comprise formula (I):

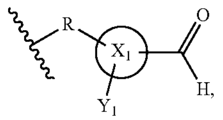

wherein $X_1$ is substituted or unsubstituted arenediyl$_{(C\leq12)}$ or substituted or unsubstituted heteroarenediyl$_{(C\leq12)}$; $Y_1$ is hydrogen or an electron withdrawing group; and R is a linker that is coupled to the solid support. The linker may comprise a monomer or a polymer. The linker may comprise a polypeptide, a polyethylene glycol, a polyamide, a heterocycle, or any combination thereof. The linker may comprise at least one oxo.

A capture moiety may comprise formula (Ia):

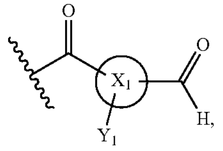

wherein $X_1$ is arenediyl$_{(C\leq12)}$, heteroarenediyl$_{(C\leq12)}$, or a substituted version of either of these groups; $Y_1$ is hydrogen or an electron withdrawing group; wherein said capture moiety is attached to said cleavable unit at the open valence of the carbonyl group. In some embodiments, $X_1$ is arenediyl$_{(C\leq12)}$ or a substituted arenediyl$_{(C\leq12)}$. In some embodiments, $X_1$ is arenediyl$_{(C\leq12)}$. In some embodiments, $X_1$ is benzenediyl. In some embodiments, $X_1$ is a heteroarenediyl$_{(C\leq12)}$ or a substituted heteroarenediyl$_{(C\leq12)}$. In some embodiments, $X_1$ is heteroarenediyl$_{(C\leq12)}$. In some embodiments, $X_1$ is pyridinediyl. In some embodiments, $Y_1$ is hydrogen. In some embodiments, $Y_1$ is an electron withdrawing group. In some embodiments, $Y_1$ is an electron withdrawing group selected from the group consisting of amino, cyano, halo, hydroxy, nitro, or a group of the formula: $—N(R_a)(R_b)(R_c)(R_d)^+$, wherein: $R_a$, $R_b$, $R_c$, and $R_d$ are each hydrogen, alkyl$_{(C\leq8)}$, or substituted alkyl$_{(C\leq8)}$; or $R_d$ is absent, wherein when $R_d$ is absent, then the group is neutral.

In some embodiments, the capture moiety may comprise the group selected from:

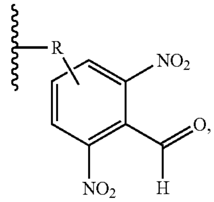
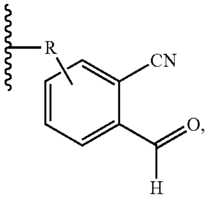
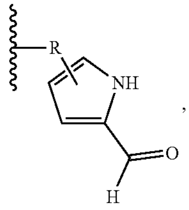
,
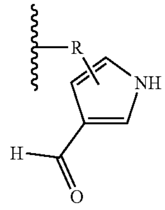
,
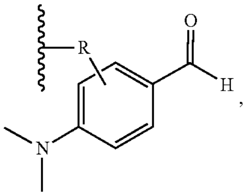
,
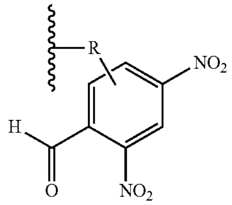
,
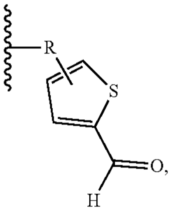
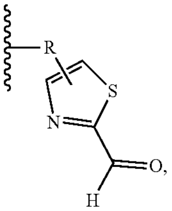
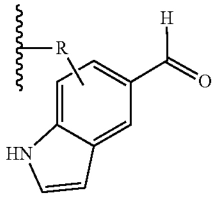
,
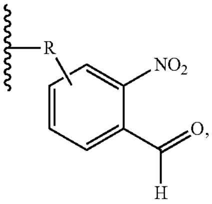
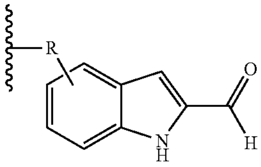
,
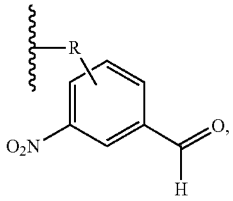
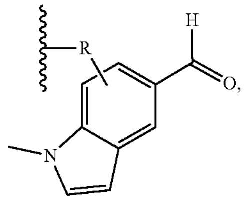
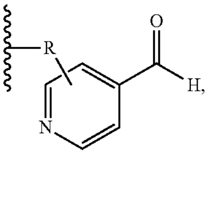
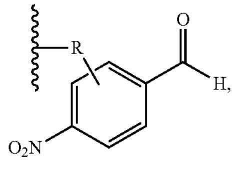
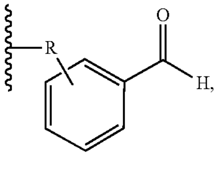

-continued
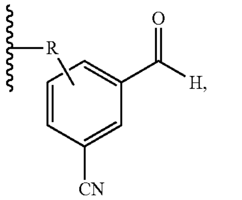
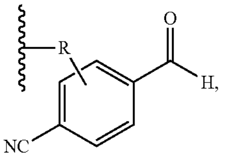
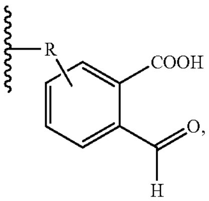
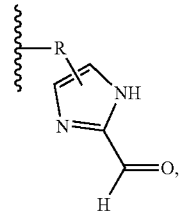
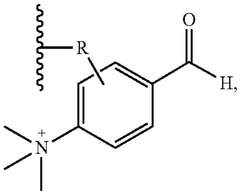
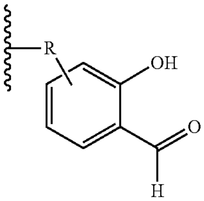
,
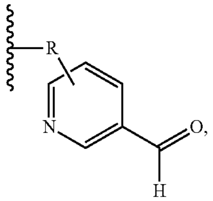
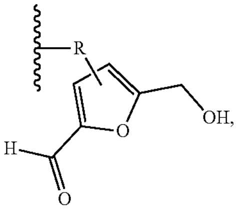
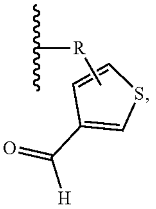
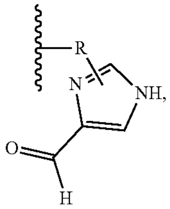
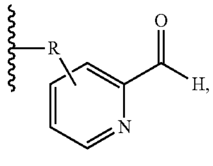
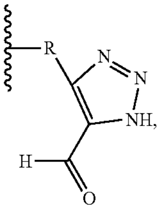
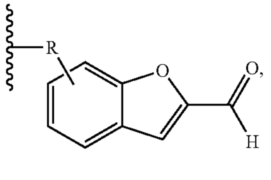
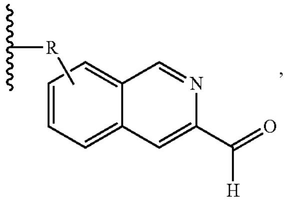
,
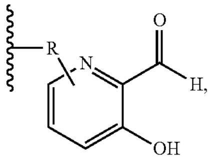
and
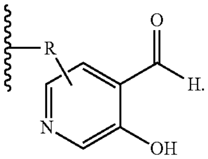
In some embodiments, the capture moiety may comprise the group selected from:
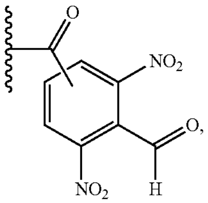
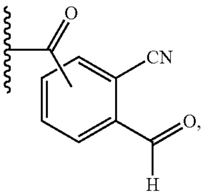
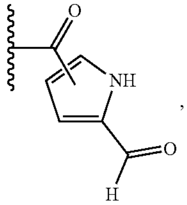
,
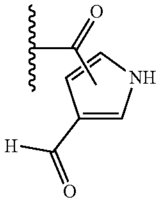
,
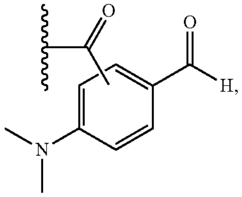
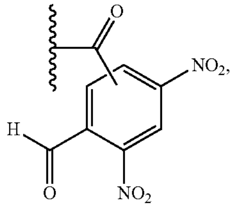
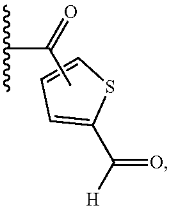
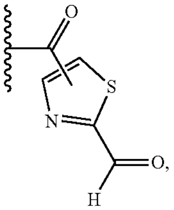
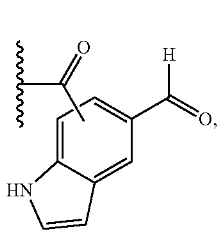
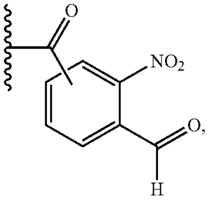
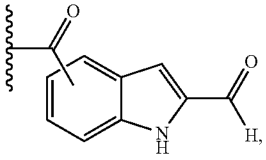
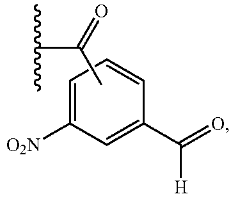
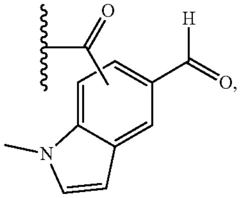
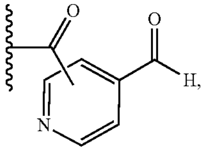
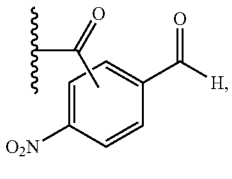
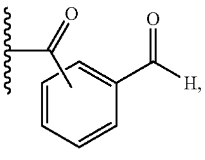

-continued

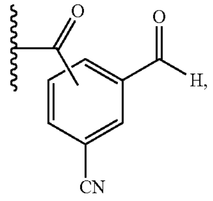

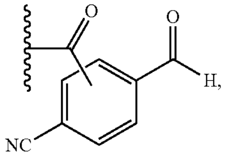

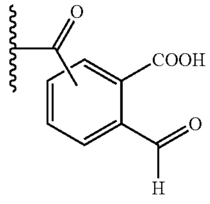

,

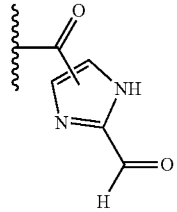

,

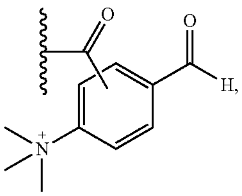

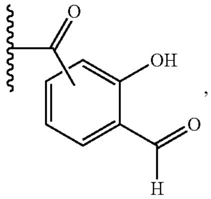

,

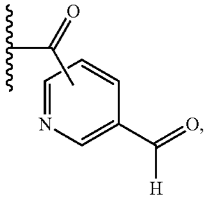

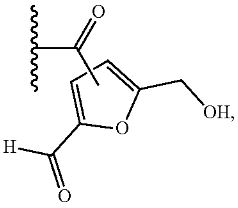

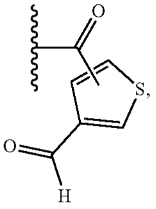

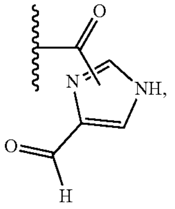

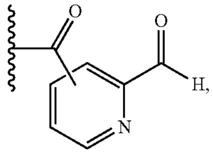

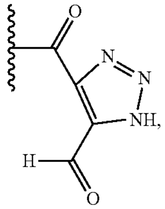

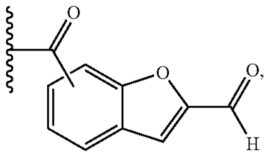

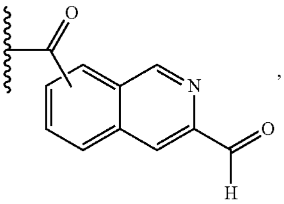

,

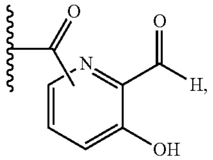

and

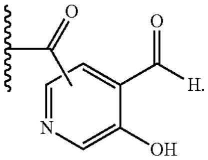

In some embodiments, the capture moiety may comprise the group selected from:

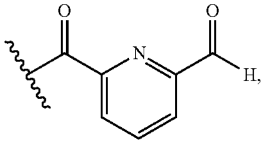

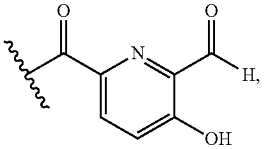

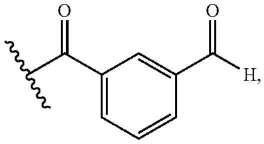

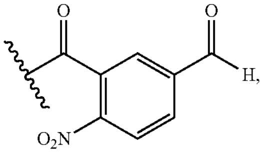

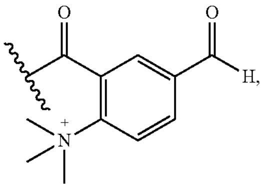

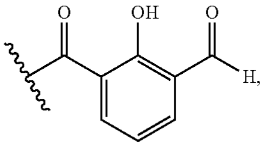

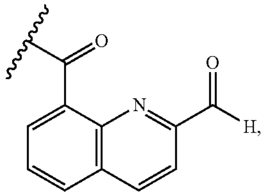

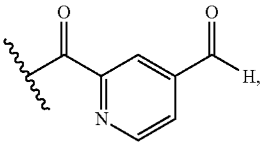

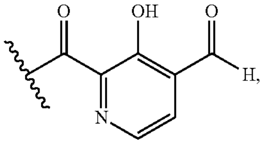

or

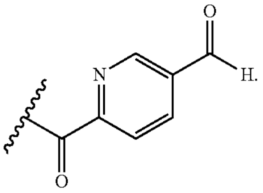

In some embodiments, the capture moiety may comprise

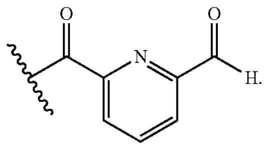

A support may comprise a plurality of nucleic acid barcode sequences, which plurality of nucleic acid barcode sequences comprises the nucleic acid barcode sequence. The plurality of nucleic acid barcode sequence may have barcode sequences that are substantially identical. The nucleic acid barcode sequence may be deoxyribonucleic acid (DNA), ribonucleic acid (RNA), a peptide nucleic acid (PNA), or any combination thereof. The nucleic acid barcode sequence may be an oligomer. The nucleic acid barcode sequence may be a polymer. The length of the nucleic acid barcode sequence may be at least 10, 20, 30, 40, 50, 60, 70, 80, 90, 100, 150, 200, 250, 300, 350, 400, 450, 500, 600, 700, 800, 900, 1,000, 10,000, or more nucleic acid bases, or any range derivable therein. The length of the nucleic acid barcode sequence may be at most 10,000, 1,000, 900, 800, 700, 600, 500, 450, 400, 350, 300, 250, 200, 150, 100, 90, 80, 70, 60, 50, 40, 30, 20, 10, or less nucleic acid bases, or any range derivable therein. The length of the nucleic acid barcode sequence may be from about 10 to about 10,000 nucleic acid bases. The length of the nucleic acid barcode sequence may be from about 10 to about 1,000 nucleic acid bases. The length of the nucleic acid barcode sequence may be from about 10 to about 100 nucleic acid bases. The nucleic acid barcode sequence may be assembled using a combinatorial assembly technique. The combinatorial assembly technique may be a split and pool technique. The split and pool technique may provide a support with a unique barcode sequence. The unique barcode sequence may directly coupled to the support. The unique barcode sequence may be coupled indirectly to the support through a pendant group. The split and pool technique may provide a support wherein each pendant group coupled to the support has a unique barcode sequence associated with the support.

A cleavable unit may comprise functional groups, such as, for example, disulfides. A cleavable unit may be cleaved by, for example, enzymes, nucleophilic or basic reagents, reducing agents, photo-irradiation, electrophilic or acidic reagents, organometallic or metal reagents, oxidizing reagents, or combinations thereof. The cleavable group can be an acid cleavable aminomethyl group (e.g., rink-amide, Sieber, peptide amide linker (PAL)), hydroxymethyl (Wang-type), trityl or chlorotrityl, aryl-hydrazide linker. The cleavable group can be a metal cleavable group, such as, for example, an alloc linker, hydrazine cleavable group, or photo-labile cleavable group, such as, for example, nitrobenzyl based (e.g., 4-[4-(1-(Fmoc-amino)ethyl)-2-methoxy-5-nitrophenoxy]butanoic acid) or a carbonyl-based linker.

The linker may comprise the building block for the nucleic acid barcode sequence. The building block for the nucleic acid barcode sequence may comprise, for example, an amine (e.g., lysine), an azide (e.g., azidolysine), an alkyne (e.g., propargylglycine) or a thiol (e.g., cysteine). A sequence for the nucleic acid barcode sequence may be coupled to the building block for the nucleic acid barcode sequence. A primer sequence for the nucleic acid barcode sequence may be coupled to the building block for the nucleic acid barcode sequence. The sequence may comprise a primer sequence. A primer sequence for the nucleic acid barcode sequence may be coupled to the building block for the nucleic acid barcode sequence. A primer sequence for the nucleic acid barcode sequence may be directly coupled to the building block for the nucleic acid barcode sequence. The nucleic acid barcode sequence may be coupled to the primer sequence.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Peptide Synthesis—Method 1. Test peptides were synthesized using a Liberty Blue Microwave Peptide Synthesizer (CEM Corporation). All amino acids were incorporated as common Fmoc protected derivatives (P3 Biosystems), using DIC/Oxyma coupling strategies using dimethylformamide (DMF) as a solvent (1:1:1). The peptides were coupled for 120 seconds at 90° C. The Fmoc group is removed with 20% piperidine at 90° C. for 60 seconds. Peptides were cleaved from the resin using a standard cocktail containing trifluoroacetic acid, triisopropylsilane, and $H_2O$ (95:2.5:2.5 eq) for 2.5 hours at room temperature, afterwards the peptide mixture was concentrated under a nitrogen stream, the sample was precipitated by adding 10 volumes of diethyl ether, and collected by centrifuging at 7,000 g for 10 minutes. The peptides were purified using reverse phase high-pressure liquid chromatography (RP-HPLC) using a Grace-Vydac C18 column (4.6×250 mm) and a 0-50% acetonitrile (0.1% formic acid) over 60 minutes. The fractions were analyzed by mass spectrometry and pure peptide was lyophilized to dryness.

Peptide Synthesis—Method 2: All peptides were synthesized using automated microwave-assisted solid-phase peptide synthesis (Liberty Blue Microwave Synthesizer, CEM Corporation). Synthesis was performed using standard Fmoc chemistry using DIC/Oxyma coupling strategies (1:1:1 ratio with amino acids). Coupling steps were performed at 90° C. for 120 seconds, and deprotection was performed using 20% piperidine in DMF at 90° C. for 60 seconds. All peptides were cleaved from resin using trifluoroacetic acid (TFA), triisopropylsilane (TIS), and $H_2O$ (95:2.5:2.5) for 2.5 hours prior to the cleavage solution being concentrated under nitrogen stream. The peptide is precipitated with ice cold diethyl ether and collected by centrifugation at 12,000 g for 10 minutes. Peptides were purified using a Grace-Vydac C18 column (Buffer A: $H_2O$+0.1% formic acid; Buffer B: Methanol+0.1% formic acid) over a 10-60% gradient.

Immobilization Condition Screen. The best conditions for immobilization were determined by mixing peptide (5 μM) solubilized in dPBS with 6-formylpyridine-2-carboxylic acid (15 μM) in dPBS. The conditions tested were temperatures 37° C. vs 60° C., pHs 7-9, and the presence or absence of 1 mM 5-methoxyaniline as a catalyst. The samples were incubated at the appropriate conditions for 16 hours. The supernatant was separated from the resin, analyzed by RP-HPLC, and compared to an RP-HPLC of the input.

Preparation of Immobilization Resin—Method A. Protide-Amine Polystyrene resin (CEM Corporation) was coupled with 3 different linkers: (1) Fmoc-Rink Linker, (2) No Linker, or (3) three glycine residues. The linkers were coupled at 4.4eq with HCTU (4eq) and DIEA (8eq) for 20 minutes each. To these linkers, 6-formylpyridine-2-carboxylic acid (Enamine) (2.2 eq) was coupled using HCTU (2eq) and diisopropylethylamine (6eq) for 1 hour in DMF at room temperature. This was then washed extensively with DMF and stored at 4° C.

Aldehyde Capture Resin Preparation—Method B: Amino PEGA resin (Novabiochem) was used and was functionalized with Fmoc-Peg2-OH, Rink linker and 6-formylpyridine-2-carboxylic acid using HCTU/DIEA (1:1:1.1 ratio) chemistry coupling for 45 minutes. Deprotection was done using 20% piperidine in DMF two times for five minutes each. Resin was stored in DMF at 4° C. prior to use.

Peptide Capture. Resin was taken and allowed to come to room temperature. Aliquots of resin were taken and rinsed extensively in DMF, $H_2O$, and Dulbecco's phosphate buffered saline (dPBS). Peptides were solubilized in dPBS and 5-methoxyaniline was added to 1 mM. The peptide-aniline mixture was then added to the resin and mixed extensively via vortexing. The resin was incubated at 60° C. for 16 hours and the supernatant was separated from the beads. Analysis using RP-HPLC was performed to determine the loading percentage of the beads by comparing an initial HPLC of the peptide solution against the binding supernatant using an equal injection amount of peptide.

In-solution N-terminal peptide capture: Peptides are mixed with four molar equivalents of aldehyde in 50 mM phosphate buffer pH 7.5. This is then incubated for 8-16 hours at 37° C. prior to purification or analysis. All aldehydes used are solubilized in DMF at 100 mM and diluted to final concentration. Samples are then analysed by LC/MS. Aminal formation was determined by quantitation of remaining unreacted peptide remaining in the HPLC.

Resin based peptide capture: Capture resin is taken and washed in DMF, water, and 50 mM phosphate buffer pH 7.5. Each wash includes a 5-minute incubation in the solvent. Peptide is then added to the resin in 50 mM phosphate buffer pH 7.5 and incubated at 37° C. for 16-24 hours. Next the resin is washed extensively in incubation buffer, water, and finally DMF. After derivatization, the resin is washed extensively in water, DMF, and finally DCM. Peptide is cleaved from resin in 95% TFA, 2.5% TIS, and 2.5% $H_2O$. The TFA is concentrated under $N_2$ stream and ether precipitated prior to mass spectrometry analysis.

Peptide Release. The resin was washed in $H_2O$ and then in dPBS, with at least 1 incubation for 15 minutes in dPBS. The release of peptides was initiated by incubating the resin with 50 mM phenyl hydrazine at 60° C. for 16 hours. The supernatant then contains the peptide, which can be isolated through filtration. Overall yield was calculated by comparing the RP-HPLC of the input peptide with the peptide that was released from the resin.

Reversal of Aminal Cap: Peptides were first allowed to react with 4-nitrobenzaldehyde, 2-pyridinylcarboxaldehyde, or 3-formylisoquinoline following standard in-solution reaction procedures (4 mM aldehyde and 1 mM peptide). These peptides were then purified using a Grace-Vydac C18 RP-HPLC column, analyzed by LC/MS and lyophilized to dryness. For the reversal tests, capped peptides were resuspended in either 0.3 M dimethylaminoethyl hydrazine or 0.3 M methoxyamine. Samples were incubated at 60° C. and then analyzed by HPLC and mass spectrometry at each time point. Percentage released is determined by comparing the integration of the HPLC peak of the capped peptide over time.

Screening of aldehyde variants for N-terminal peptide capture. 1 mM Ser-Gly-Trp peptide in 50 mM sodium phosphate buffer pH 7.5 is mixed with each aldehyde (4 mM final concentration) and solubilized in DMF. These are shaken at 37° C. for 6 hours prior to LC-MS analysis Buffer A: $H_2O$+0.1% formic acid; Buffer B: MeCN+0.1% formic acid; Each reaction was performed in triplicate.

Testing the selectivity towards the N-terminal amines. A Ser-Gly-Lys-Trp peptide was solubilized at 1 mM in 50 mM sodium phosphate buffer pH 7.5 and incubated with the aldehyde (4 mM final concentration) at 37° C. for six hours.

Cell Growth Conditions: HEK-293T cells were grown in Dulbecco's Modified Eagle Medium with 10% Fetal Broth Serum at 37° C. and 5% $CO_2$. Cells were passaged when between 70-80% confluence.

HEK Lysate Digestion and Capture: Cells were grown to 80% confluence and harvested in PBS and pelleted at 500 g for 3 minutes. Cells then suspended in hypotonic 50 mM Tris-HCl buffer pH 8 and placed on ice. Protease inhibitor (Mini cOmplete, EDTA Free protease inhibitor cocktail, Roche) was added to 1× concentration. Cells were sonicated (Branson 2510) for 1 minute at 42 kHz and placed on ice for an additional minute. This was repeated 3 times. The solution was then centrifuged at 17,000 g for 10 minutes at 4° C. and the supernatant was collected. Protein content was then measured using a Bradford Assay. 250 µg of protein was denatured in 2,2,2-trifluoroethanol (TFE) and 5 mM tris(2-carboxyethyl)phosphine (TCEP) at 45° C. for 45 minutes. Proteins were then alkylated in the dark with 5.5 mM iodoacetamide. Remaining iodoacetamide was quenched in 100 mM dithiothreitol. Trypsin was then added to the solution in a ratio of 1:25.

Mass Spectrometry: Peptides were separated on a 75 µM×25 cm Acclaim PepMap100 C-18 column (Thermo Scientific) using a 3-45% acetonitrile+0.1% formic acid gradient over 120 min and analyzed online by nanoelectrospray-ionization tandem mass spectrometry on an Orbitrap Fusion (Thermo Scientific). Data-dependent acquisition was activated, with parent ion (MS1) scans collected at high resolution (120,000). Ions with charge 1 were selected for collision-induced dissociation fragmentation spectrum acquisition (MS2) in the ion trap, using a Top Speed acquisition time of 3-s. Dynamic exclusion was activated, with a 60-s exclusion time for ions selected more than once. MS data was acquired in the UT Austin Proteomics Facility.

Protein Identification: Protein identification was done using Proteome Discoverer 2.3 (Thermo Scientific). The human proteome was first downloaded from Uniprot. Raw formatted mass spectrometry files were loaded onto Proteome Discoverer and peptides and proteins were identified using Sequest HT (Eng, 1994). PCA protected peptides were identified by using a peptide N-terminal dynamic modification (132.032 Da) corresponding to the PCA modified peptide with a false discovery rate of 1%.

On Bead Labeling of Peptides: Peptides are captured to PCA resin as described. After rinsing the C-terminus was first coupled with 100 mM propargylamine, 100 mM HCTU, and 100 mM triethylamine in DMF. The resin was extensively washed with DMF and the Lys residues were labelled with 0.5 mM Atto647N-NHS (Attotec). The resin was washed extensively in DMF and DCM and all of the peptides cleaved from the resin with a TFA cocktail (95% TFA, 2.5% $H_2O$, and 2.5% TIS) for 2.5 hours. The supernatant was collected and concentrated with a $N_2$ stream. Ice cold diethyl ether is added (10 vol) and the peptides collected by centrifugation for 10 minutes at 17,000 g. The peptide was analysed by high-resolution mass spectrometry to confirm the double labelling.

Single Molecule Peptide Sequencing: Approximately 200 pM of peptides are immobilized on an azide slide (custom slides from PolyAn, Germany) using standard Cu(I)-Click chemistry. Briefly a 2 mL solution comprising peptide (200 pM), CuSO4/tris-hydroxypropyltriazolylmethylamine (THPTA) mix (1 mM/0.5 mM) and freshly prepared sodium L-ascorbate (5 mM) was incubated on the azide slide at room temperature for 2 hours. Following the incubation, the slides were rinsed with water and fluorosequencing performed as previously described with minor modifications [21]. To deprotect the N-terminal PCA cap, the slides were bathed in 0.5M DMAEH at 60° C. for 16 hours. The images were processed using custom developed script (available at github.com/marcottelab/FluorosequencingImageAnalysis/ github:).

Example 1—Peptide Capture

The reaction between peptides and 2-pyridinecarboxaldehyde (PCA) has been used to capture full length proteins (MacDonald et al., 2015). Previous reports perform this coupling at a 100-fold excess of PCA over peptide in 4 hours at 37° C., which allows for 80+% coupling for a majority of peptides. However, to be able to use this chemical to capture small amounts of peptides, the reaction was optimized in solution to ensure complete peptide capture. For all reactions performed, the bifunctional 6-formylpyridine-2-carboxylic acid (FPCA) was used. This compound allows for N-terminal capture and contains a carboxyl acid moiety, which can be used to couple to the resin. A screen of binding conditions was performed in solution to find conditions that maximize the capture of low abundance peptides. 2-Nitrobenzaldehyde, 3-nitrobenazldehyde, 4-nitrobenzaldehyde, 2,4-dinitrobenzaldehyde, 2,6-dinitrobenzaldehyde, and 2-cyanobenzaldehyde were also tested as capture molecules. The cyano and mono nitro derivatives all performed well (FIG. 1). 4-trimethylamino benzaldehyde will also be tested for peptide capture.

Figure 2:
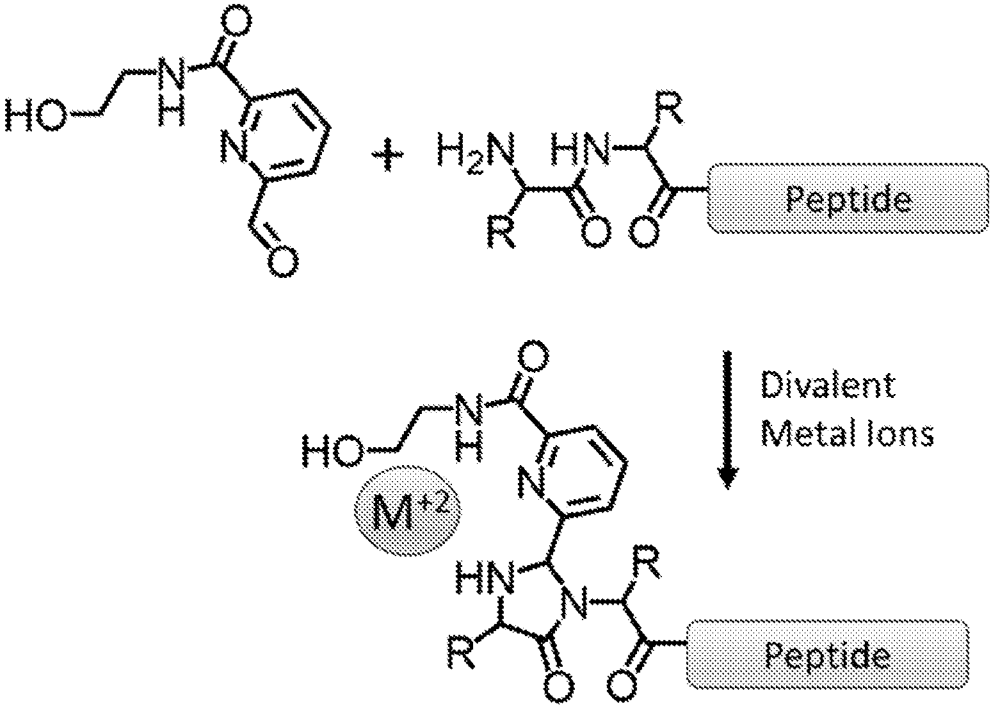
FIG. 2. Schematic of metal catalysis of the immobilization reaction.
Figure 3:
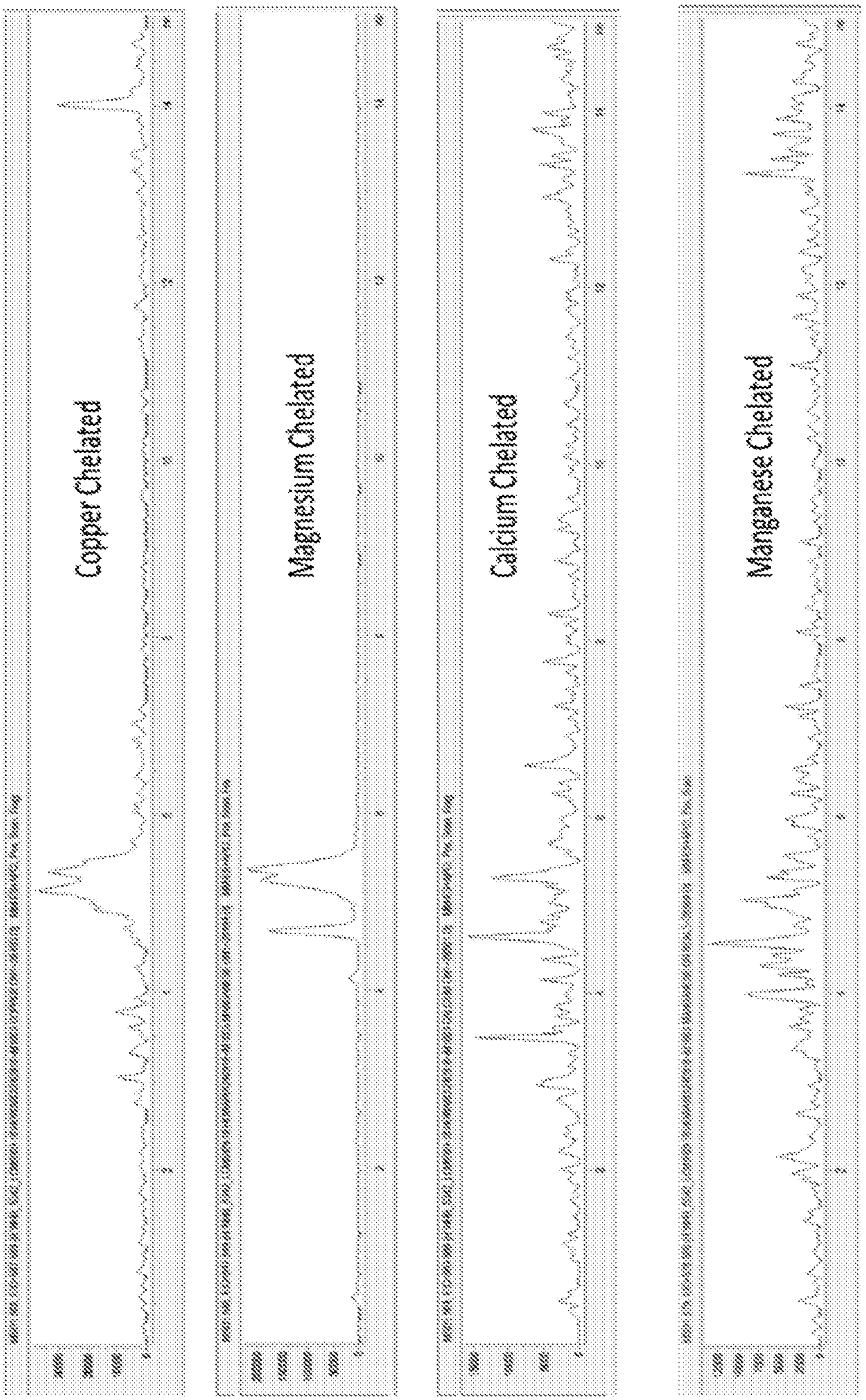
FIG. 3. Mass spectrometry analysis of metal catalysis reactions.

To find the optimal conditions, temperature, pH, and the addition of a catalyst to promote the formation of the initial Schiff base were screened. A slight excess of FPCA (3eq) with 1 mM 5-methoxyaniline as a catalyst, with an overnight incubation at 60° C. worked well. Metal ions (zinc, copper, magnesium, calcium, iron, cobalt, manganese, and nickel) were also tested for their ability to catalyze the peptide immobilization reaction (FIG. 2). Copper, magnesium, calcium, and manganese were all found to catalyze the peptide immobilization reaction, with copper and magnesium chelating to the Amide-PCA-Peptide structure (FIG. 3).

Figure 4A:
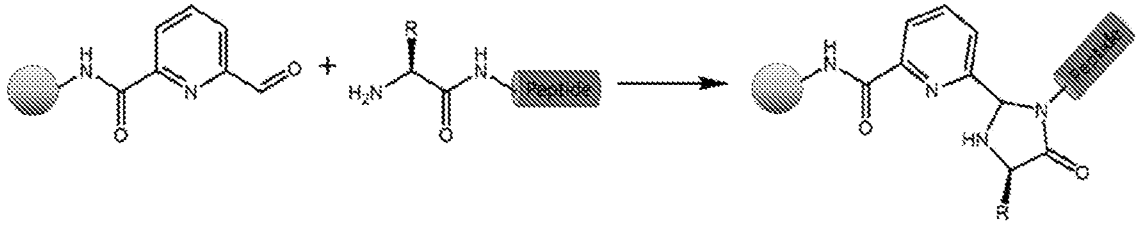
FIGS. 4 A & B. Schematics of resin-based and chemical peptide capture using 6-formylpyridine-2-carboxylic acid capture moiety.
Figure 4B:
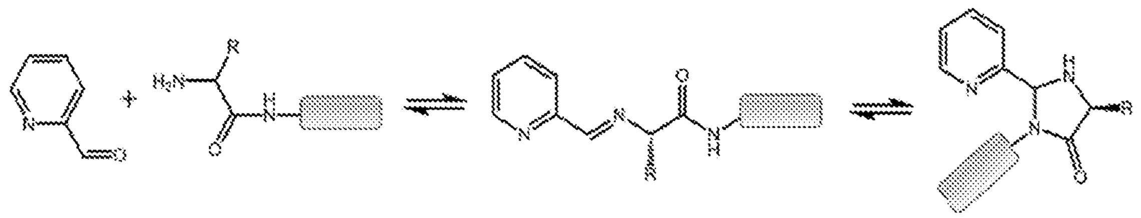

Next, resin was prepared by coupling the FPCA to a resin through the carboxylic acid moiety. This allows for the N-terminal immobilization of peptides to the resin (Table 1), which can then be manipulated chemically in any way that the experiment set demands (FIGS. 4A and 4B). With this resin, ~60% of peptides incubated were captured (Table 2).

TABLE 1

TV-terminal capping of peptides in solution.

| | 37° C. | | 60° C. | |
|---|---|---|---|---|
| | Sample | Percent | Sample | Percent |
| pH 7.4 | No Cat. | 0 | No Cat. | 45 |
| | Cat. | 47 | Cat. | 63 |
| pH 8 | No Cat. | 0 | No Cat. | 52 |
| | Cat. | 41 | Cat. | 59 |
| pH 9 | No Cat. | 18 | No Cat. | 44 |
| | Cat. | 41 | Cat. | 61 |

TABLE 2

Resin-based peptide capture on three different linkers.

| | Catalyzed | | Uncatalyzed | |
|---|---|---|---|---|
| FPCA Connection | Bound % | Release % | Bound % | Release % |
| Rink Linker | 42 | 9 | 22 | 9 |
| No Linker | 37 | — | 38 | — |
| 3xGly | 69 | 19 | 60 | 16 |

Figure 5:
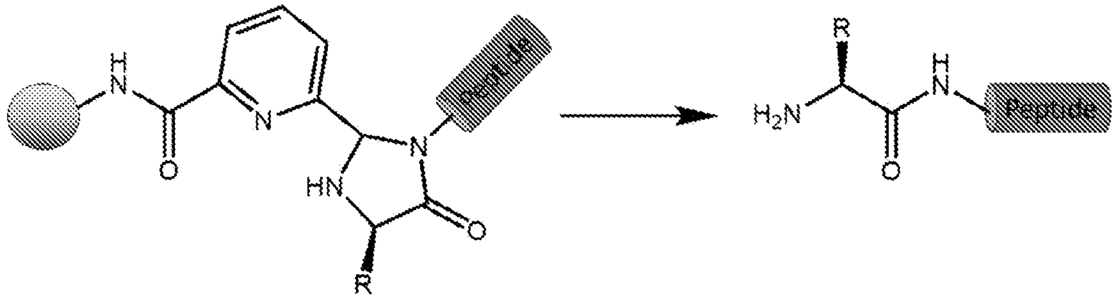
FIG. 5. Schematic of peptide release from the N-terminal immobilization.

With peptide on resin, conditions that allowed for successful reversal of the covalent bond were screened. It was considered that this covalent bond could be reversed using heat and a chemical that makes a more stable bond with an aldehyde. When the resin was incubated at 60° C. with a hydrazine, the peptide was found in the supernatant (FIG. 5). After optimization of hydrazine and timing, 33% of the peptide bound to the resin was released, for a 20% overall yield of peptide (Table 2). If desired, it is also possible to install secondary cleavage handles to the resin, to allow for the release of N-terminally capped peptides into solution to allow for further manipulation.

Example 2—Labeling of Captured Peptides

Figure 6:
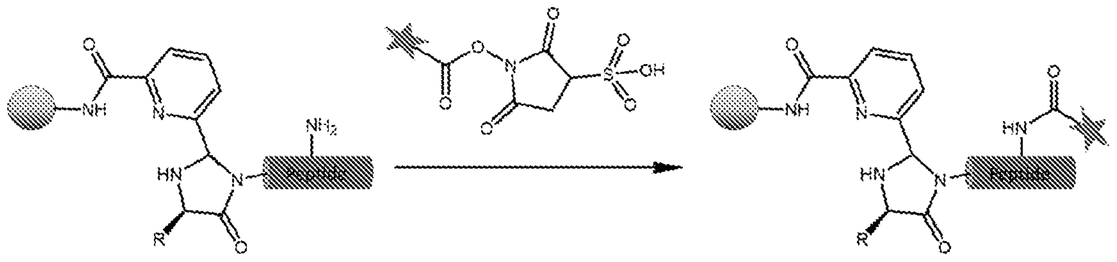
FIG. 6. Scheme for labeling lysine residues on resin-captured peptides.

After the peptides are captured by the peptide resin, it is possible to perform any chemical reaction required. This includes isobaric, fluorescent, biotin, or PEG labeling of proteins as well as acetylation or other capping steps required prior to analysis. It also allows for multiple of these steps to be performed without subsequent purification steps, in a similar vein to solid-phase peptide synthesis (FIG. 6).

Example 3—Probe Design

Figure 7:
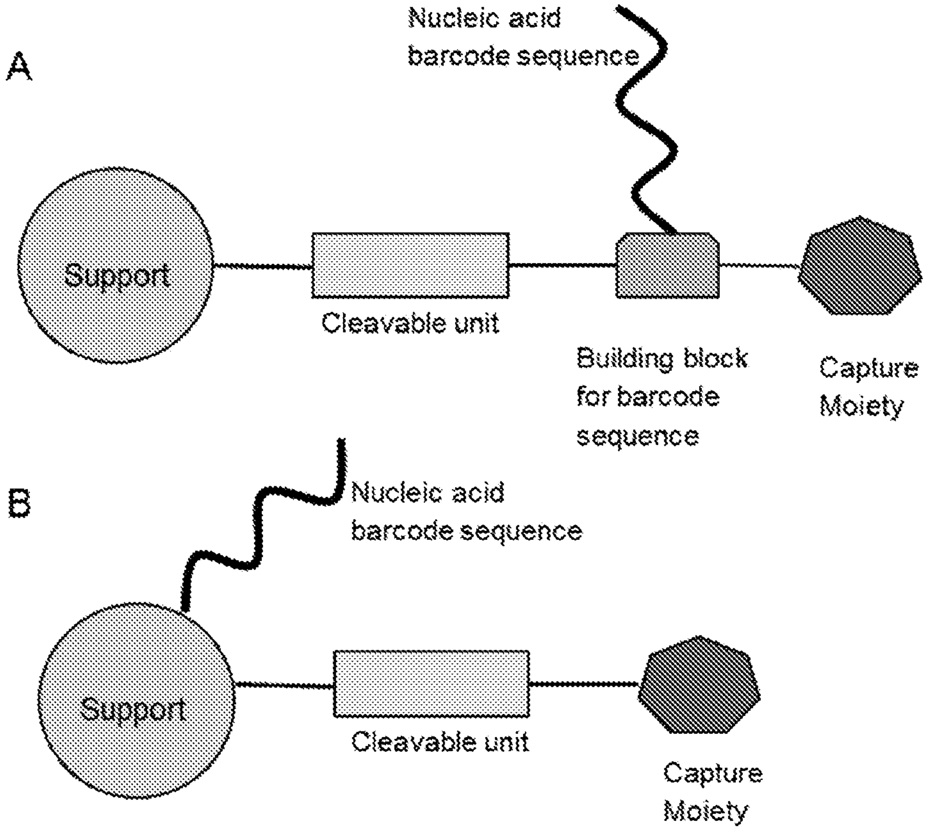
FIGS. 7A & B. The design of single-cell proteomics capture supports.

The resins can be designed and synthesized to contain a linker between the capture moiety (e.g., PCA) and the support. A unique identifier, such as, for example, an oligomer (e.g., DNA, RNA, PNA) or a tandem mass tag (TMT), can be incorporated into the linker or onto the support. Examples of probe designs is depicted in FIGS. 7A & 7B. The probes in FIGS. 7A and 7B represent probes containing nucleic acid barcode sequences, but the nucleic acid barcode sequences can be replaced with barcodes described herein.

Other such designs can be envisioned if cleavage from the bead is not desired. For example, the probe may not contain a cleavable unit. The probe can be built with a cleavable group in the linker, and the peptide can be cleaved from the probe via the cleavable group. The PCA adduct is then, depending on its use, removed by use of the hydrazine type releasing agent. Thus, a two-step releasing process is possible. Even if the second step (i.e. the use of hydrazine) is not done, the peptide with an adduct can have sufficient advantages and improvements in downstream analysis.

The support is made such that each solid support (or a small subset thereof) contains barcodes (e.g., oligomers) with the same sequence. It can be made in batches or by local amplification of oligomers to build a unique sequence on the building block. The goal is to have a population of beads, each containing the same sequence of oligomer but different from another bead.

Example 4—Automation

To be an effective method for both large and small-scale use, it is important to automate the sample preparation and reactions. This will allow for the method to be used by a wider range of groups, with a lower requirement for special knowledge and skills. The Liberty Blue Peptide Synthesizer (CEM Corporation) will be used as a microwave reaction that can take protein input samples for mass spectrometry and prepare them for analysis without human intervention. It is likely that the energy input from the microwave will increase the overall yield of the capture/release, and despite the additional steps, will decrease the time requirements for sample preparation. The Liberty Blue can also be customized to allow for the preparation of 12+ samples.

Example 5—Screen for Aldehydes

To understand substituent effects on the peptide capture, aromatic and heteroaromatic aldehydes possessing different rings, heteroatoms, and regiochemical placement of the aldehyde were screened. In total 30 aldehydes were tested and ranked in order of the amount of N-terminally capped product, as an imidazolinone, formed on the model peptide Ser-Gly-Trp in a six-hour reaction at 37° C. in 50 mM sodium phosphate buffer pH 7.5 (Table 3). Table 3 displays the structure and the percent aminal formed based on the quantitation of the area under the curve from the HPLC of the reaction. Each reaction was analyzed by LC/MS, and aminal formation was confirmed by the presence of two distinct peaks in the 218 nm HPLC trace which had masses corresponding to the PCA capped product. These two peaks are due to the separation of diastereomers formed during the ring closure, which can be separated during reverse phase chromatography.

Of the compounds screened, compounds containing strongly electron-withdrawing groups (Table 3. e.g., A and F) did not lead to significant imine-intermediates (i.e., the step required prior to ring closure). This may be due to the aldehyde being largely hydrated, which may not reverse to allow imine formation. However, less electron withdrawing character facilitated product formation, but produced poor yields (e.g., J, L, N, O, Q, R, W). Imidazolinone formation was also disfavored when the aldehyde was on an electron rich aromatic ring, such as a thiazole/pyrrole e.g., C, D, E, G, H, K), or had a substituent with a large negative Hammett sigma-value (M). Aldehydes that promote the formation of the imine complex through intramolecular hydrogen bonding or through a general-acid catalyzed mechanism (Villain et al., 2001; Jin et al., 2013), albeit having a negative Hammett value, can promote product formation (e.g., V).

Electronic withdrawing character may promote nucleophilic attack of the N-terminal amine and ring closure with the adjacent amide, but not so much as to favor hydration. Thus, electron withdrawing heteroatoms adjacent to the aldehydes (e.g., pyridines, triazoles, imidazoles, and furans) promoted the imidazolinone formation.

TABLE 3

Resin-based peptide capture on three different linkers.

| Compound | Structure | % aminal formation |
|---|---|---|
| A | 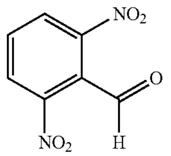 [SMILES: O=Cc1c([N+](=O)[O-])cccc1[N+](=O)[O-]] | x |
| B | 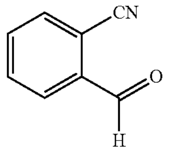 | x |
| C | 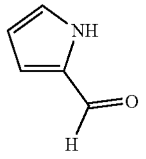 | x |
| D | 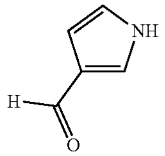 | x |

TABLE 3-continued

Resin-based peptide capture on three different linkers.

| Compound | Structure | % aminal formation |
|---|---|---|
| E | 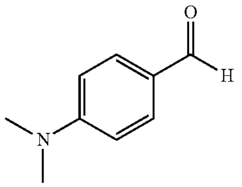 | x |
| F | 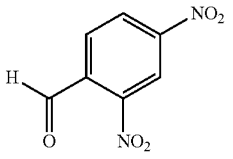 [SMILES: O=Cc1ccc([N+](=O)[O-])cc1[N+](=O)[O-]] | x |
| G | 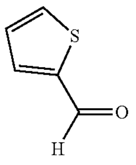 | x |
| H | 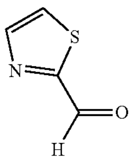 | x |
| I | 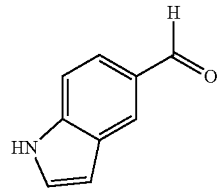 [SMILES: O=Cc1ccc2[nH]ccc2c1] | xx |
| J | 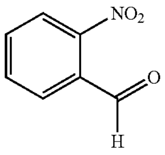 [SMILES: O=Cc1ccccc1[N+](=O)[O-]] | xx |
| K | 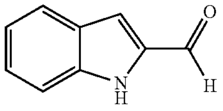 [SMILES: O=Cc1cc2ccccc2[nH]1] | xx |
| L | 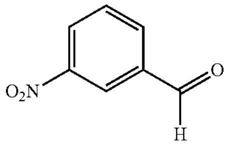 [SMILES: O=Cc1cccc([N+](=O)[O-])c1] | xx |
| M | 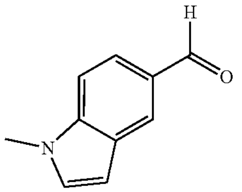 | xx |

TABLE 3-continued
| Resin-based peptide capture on three different linkers. | | |
|---|---|---|
| Compound | Structure | % aminal formation |
| N | 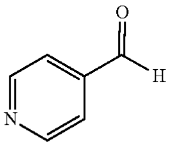 | xx |
| O | 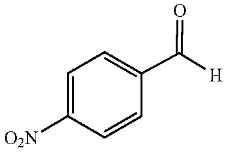 | xx |
| P | 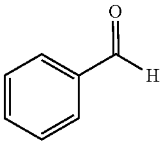 | xx |
| Q | 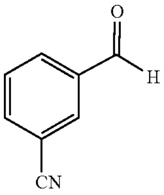 | xx |
| R | 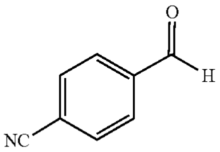 | xx |
| S | 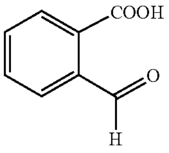 [SMILES: O=Cc1ccccc1C(=O)O] | xx |
| T | 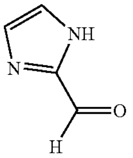 | xx |
| U | 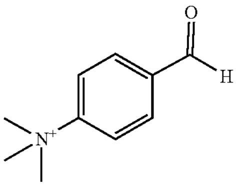 | xx |
| V | 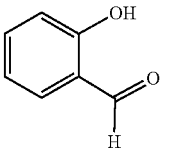 | xxx |
TABLE 3-continued
| Resin-based peptide capture on three different linkers. | | |
|---|---|---|
| Compound | Structure | % aminal formation |
| W | 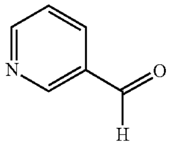 | xxx |
| X | 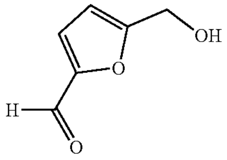 | xxx |
| Y | 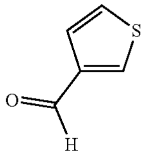 | xxx |
| Z | 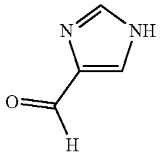 | xxx |
| AA | 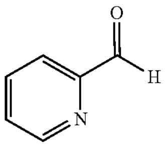 | xxx |
| BB | 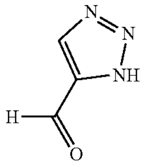 | xxx |
| CC | 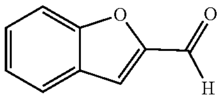 [SMILES: O=Cc1cc2ccccc2o1] | xxx |
| DD | 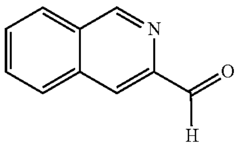 [SMILES: O=Cc1cc2ccccc2cn1] | xxx |
| EE | 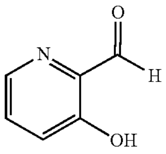 | n.d. |

TABLE 3-continued

| Resin-based peptide capture on three different linkers. | | |
|---|---|---|
| Compound | Structure | % aminal formation |
| FF | 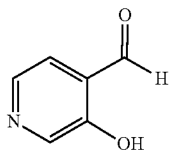 | n.d. |

x represents 0-30% aminal formation;
xx represents 30-50% aminal formation;
xxx represents 50-100% aminal formation;
n.d. indicates not disclosed.

Example 6—Selectivity

Figure 8:
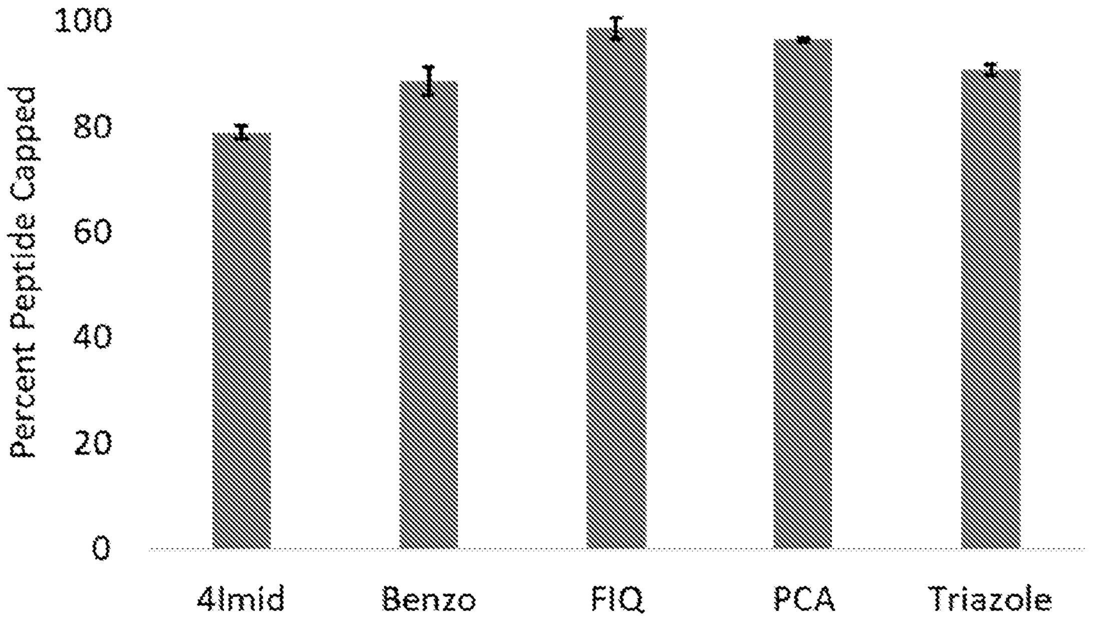
FIG. 8. A depiction of the percent of N-terminal capped product of SGKW peptide with various aldehydes.

From the group of aldehydes of Table 3, the top candidates were tested to determine if they are specific for the N-terminus, or if they are also reactive with the side chain of lysine. 4-imidazolecarboxaldehyde (Z), 2-pyridinylcarboxaldehyde (AA), 1H-1,2,3-triazole-5-carbaldehyde (BB), benzofuran-2-carboxaldehyde (CC), and 3-formylisoquinoline (DD) were tested (FIG. 8). A Ser-Gly-Lys-Trp peptide was solubilized at 1 mM in 50 mM sodium phosphate buffer pH 7.5 and incubated with the five aldehydes (4 mM final concentration) at 37° C. for six hours. These five aldehydes showed similar imidazolinone formation as in the initial screen, and no product was detected that corresponded to peptide with both an N-terminal imidazolinone and an imine on the lysine side chain (FIG. 8).

Example 7—Cleavage for Peptide Release

Figure 9:
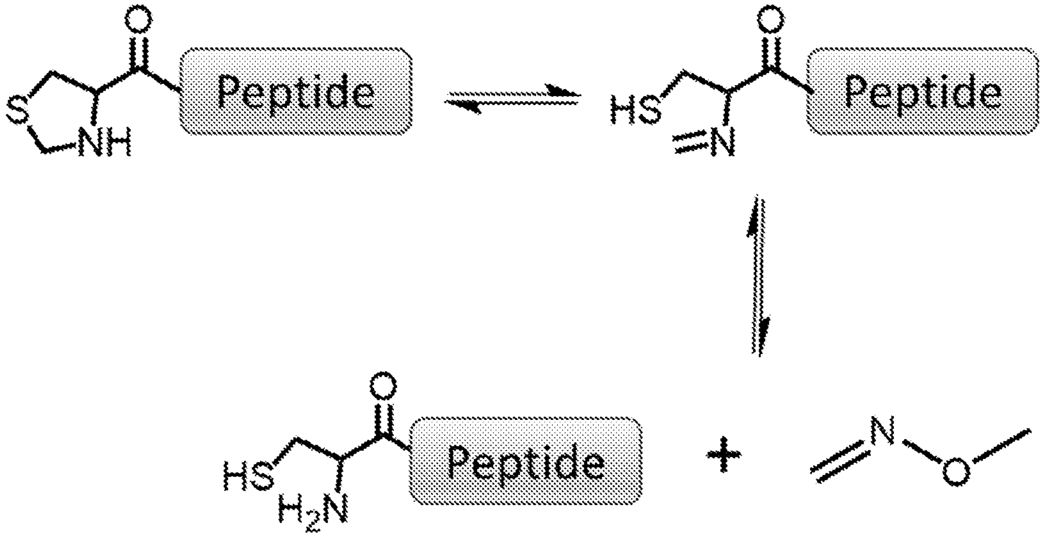
FIG. 9. A representation of the reversible reaction mechanism for the deprotection of a thiazolidine peptide with methoxyamine.

Conditions were screened to release the free N-terminus of a peptide from the imidazoline ring by cleavage of this ring's aminal linkage. The aminal linkage is similar to a thiazolidine (FIG. 9) (Saiz et al., 2009). A thiazolidine can derive from the condensation of an aldehyde, commonly formaldehyde, with cysteine, to generate a five-membered ring. This ring can interconvert with an open imine form (Shimko et al., 2013). The Cys residue can be released through incubation with methoxyamine, at pH 3, which intercepts the ring opened imine to undergo an exchange to an oxime (Kool et al., 2014).

The imidazolinone capped peptides in similar ring opening conditions were tested using a Ser-Gly-Trp peptide that had undergone a capping reaction with 4-nitrobenzaldehdye (Table 3, O), 2PCA (Table 3, AA), or 3-formylisoquinoline (Table 3, DD) was purified (e.g., FIG. 10A). Characterization of the products was performed via mass spectrometry, the peptides were purified by HPLC, and the products analyzed by $^1$H-NMR spectroscopy. These three aldehydes were chosen to span a broad range of aminal formation reactivities and diversity of the groups appended to the aromatic system.

The reversibility of the imidazolinone was characterized using the three peptides under thiazolidine ring-opening conditions. Initial studies used 0.3M methoxyamine at pH 3, and this showed a reversal of the imidazolinone at with 50-75% of peptide released after 24 hours at 60° C. (FIG. 10B). To improve the kinetics of release, several reversal reactions with the more reactive nucleophile dimethylaminoethyl hydrazine (DMAEH) were performed. Using the same conditions, greater than 90% of the aminal was reversed to the free peptide after 24 hours for all three peptides (FIG. 10C).

The extent of reversal was independent of the aldehyde used, with all three capped peptides undergoing deprotection to similar extents at all time points tested with both DMAEH and methoxyamine. This may indicate that trapping an intermediate, likely an imine with the N-terminal amine, determines the rate of product formation. Thus, an unfavorable equilibrium to the imine prior to nucleophilic capture may be the general mechanism. In summary, the animal linkage is stable at low pH on its own but is reversible when the reaction contains a nucleophilic scavenging reagent, such as methoxyamine or DMAEH.

Example 8—Peptide Capture

Figure 11:
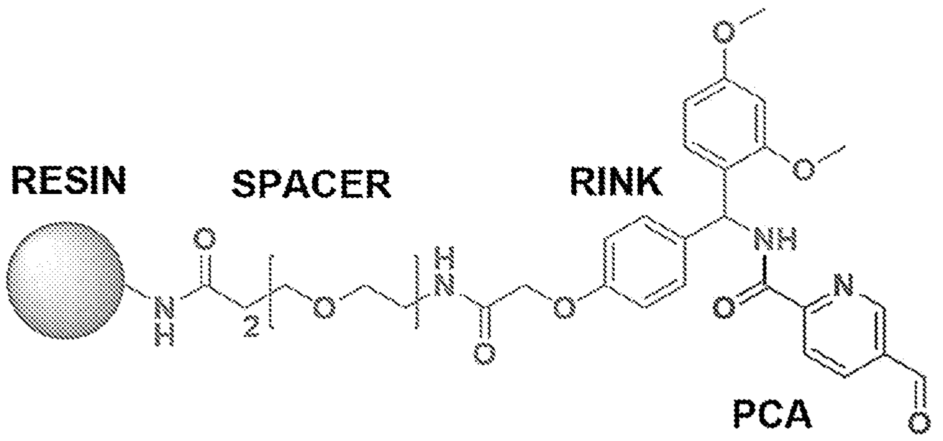
FIG. 11. An example of a peptide capture resin.

With a robust method for reversing the capped peptide, a peptide capture resin capable of being assembled using readily available reagents was developed. A water swellable PEG amine resin was amide coupled to 6-formyl picolinic acid (FPCA) attached to a trifluoroacetic acid (TFA) cleavable Rink linker (FIG. 11). A large number of other resins were screened, including Tentagel, Protide resin (CEM). This allows for peptides to be captured onto the resin, and then cleaved using, for example, TFA or DMAEH, depending upon obtaining the capped aminal peptide or free peptide, respectively. Capture is most efficient when there are roughly 50 equivalents of aldehyde on resin compared to peptide. The release of peptides proceeds cleanly using a TFA cleavage; however, DMAEH cleavage gave a lower yield when performed on resin compared to in-solution. Thus, a possible procedure is to first release the capped peptide from the resin followed by reversal of the cap.

To evaluate the extent of capture and release by the aldehyde resin, a capture of angiotensin-I peptide was performed (FIG. 12A). Capture of the peptide was determined by comparing the integrated peaks corresponding to the peptide during RP-HPLC analysis of the (i) initial solution (FIG. 12B) and (ii) after flow-through of the resin (FIG. 12C). An >80% reduction in peptide level was found, indicating that the resin can capture a majority of the input sample (FIGS. 12B and 12C). The steps for coupling and releasing peptides include: (a) peptide in 50 mM sodium phosphate pH 7.5 is added to the resin and incubated at 37° C. for 16 hours, (b) the peptide is liberated from the resin using 95% trifluoroacetic acid, 2.5% $H_2O$, and 2.5% triisopropyl silane for 2.5 hours B-C) HPLC of angiotensin I input (A) and TFA cleavage (B) after capture on PEG-Rink-FPCA resin. The grey line indicates area under curve used to quantitate percent of peptide captured. The captured peptide was released from the resin using a TFA cocktail to free the capped peptide and analyzed with high-resolution mass spectrometry. This showed that the peptide released is the pyridinyl aminal capped product and there is no detectable non-specific binding of peptide to the resin. When the capped peptide is subjected to ultraviolet photodissociation (UVPD) mass spectrometry, peptide fragments can be seen that indicate the aminal is the majority species and no imine capped peptide can be detected.

Example 9—One-Pot Digestion, Capture, and Release

Since the buffer and temperature conditions for solid-phase peptide capture and protease digestion (commonly used trypsin) are similar, using pH 7.5 sodium phosphate buffer and at 37° C., both the whole cell proteome digestion and capture of the cleaved peptides were performed in the same reaction vessel. As illustrated in FIG. 13A, proteins from lysed HEK 293T cells (10 million cells) were mixed with the capture resin along with trypsin protease in neutral sodium phosphate buffer. The reaction vessel was incubated overnight at 37° C. and the nearly 9000 proteins were identified from the resin cleaved peptides using mass-spectrometry. The rink linker was cleaved releasing the peptides with the N-terminal PCA adduct. Using tandem mass spectrometry, the extent of PCA modification on all the released peptides was determined. Nearly 40-50% of the proteins identified contained the N-terminal PCA modification. As expected, a very low amount of modified PCA adduct is observed in the flow-through (uncaptured peptides) (FIG. 13B).

By measuring the fold change in the N-terminal amino acid frequency between the PCA modified and unmodified peptides, no preference for a majority of the amino acids was observed (FIG. 13C). The outliers were peptides with N-terminal alanine, which was observed more than as frequently, while N-terminal methionine peptides that had lower preference for the resins.

These set of experiments demonstrate the utility of the capture resin to selectively and covalently react with only peptides generated from whole cell proteomes in a single reaction vessel. A relatively unbiased and covalent capture of peptides on the solid-phase helps in preventing losses due to the variations in peptide solubility and non-specific interactions with reaction tubes during sample handling.

Example 10—Labeling for Single-Molecule Sequencing

Covalent capture of peptides makes it possible to perform multiple steps of peptide derivatization for downstream proteomic analysis (e.g., single-molecule protein fluorosequencing). The technique requires conjugating multiple fluorophores and functional moiety with selectivity to the amino acid side chains. Adding a large excess of these reagents to drive the completeness of the reaction and removing the excess reagents from the labeled peptide are beneficial for improving the accuracy of the sequencing method.

In the example, more than 80% of the synthetic peptide (sequence: $H_2N$-AKAGAGRYG-OH) was captured on to the beads. Amide coupling on the C-terminal carboxylate with excess propargylamine (~50 eq) was then performed to create a terminal alkyne linker on the peptide. Subsequently, the excess reagents were washed away using multiple solvent washes and labeled the lysine on the captured peptide with Atto647N-NHS (~2eq). The unreacted dyes were washed, and the peptide cleaved with TFA. Absorbance and MS spectrum shows evidence for greater than 70 presence of labeled peptides (FIG. 14A-14C). The resin immobilized peptide's (sequence $H_2N$-AKAGAGRYG-OH) (1) C-terminal carboxylate was labeled with propargylamine and (2) amine side chain of lysine was labeled with Atto647N fluorophore. The 16 min gradient LC-MS analysis indicated that >70% of the products observed with 640 nm LC trace corresponds to the multiply labeled peptide. FIGS. 14A and 14B corresponds to the peptide with Atto647N dye and the alkyne label. While inset A corresponds to peptide without the N-terminal PCA adduct, FIG. 14B is the PCA capped peptide. FIG. 14C indicates side products observed in the reaction. While no free dyes were observed in the cleaved product, 640 nm absorbance peak was observed, with unidentifiable side-products. The fluorescently labeled peptides were incubated on azide functionalized slide using copper-click chemistry, and thee PCA adduct was removed using 0.5M DMAE at 60° C. overnight.

Figure 15A:
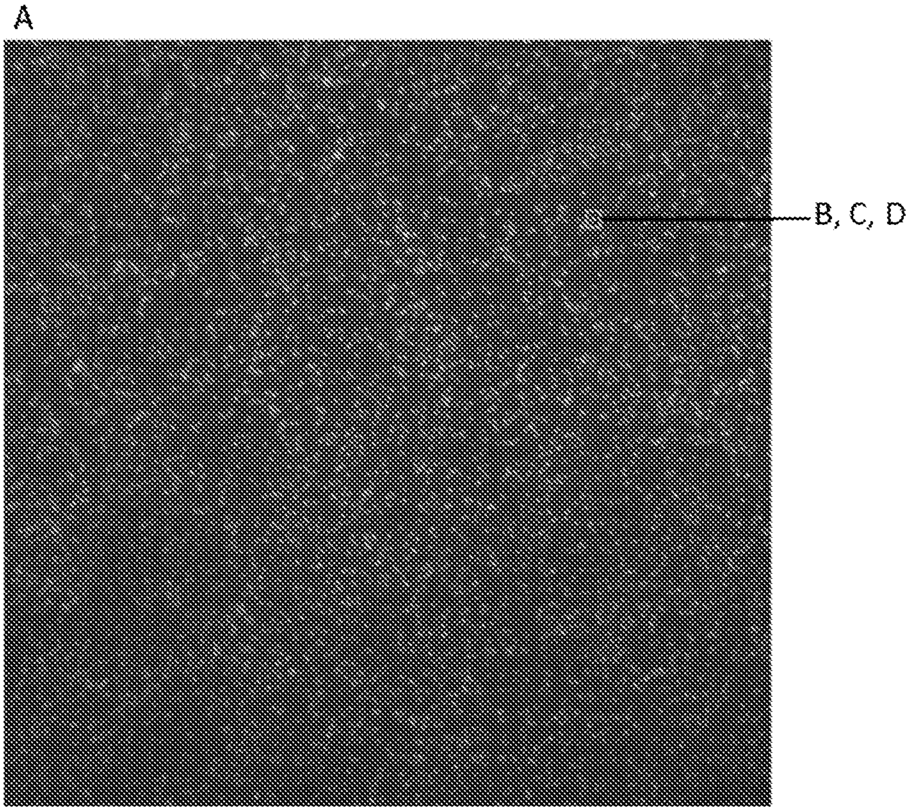
FIG. 15A-15D. A depiction of resin-captured and labeled peptides analyzed by single molecule peptide sequencing.
Figures 15B, 15C, 15D:
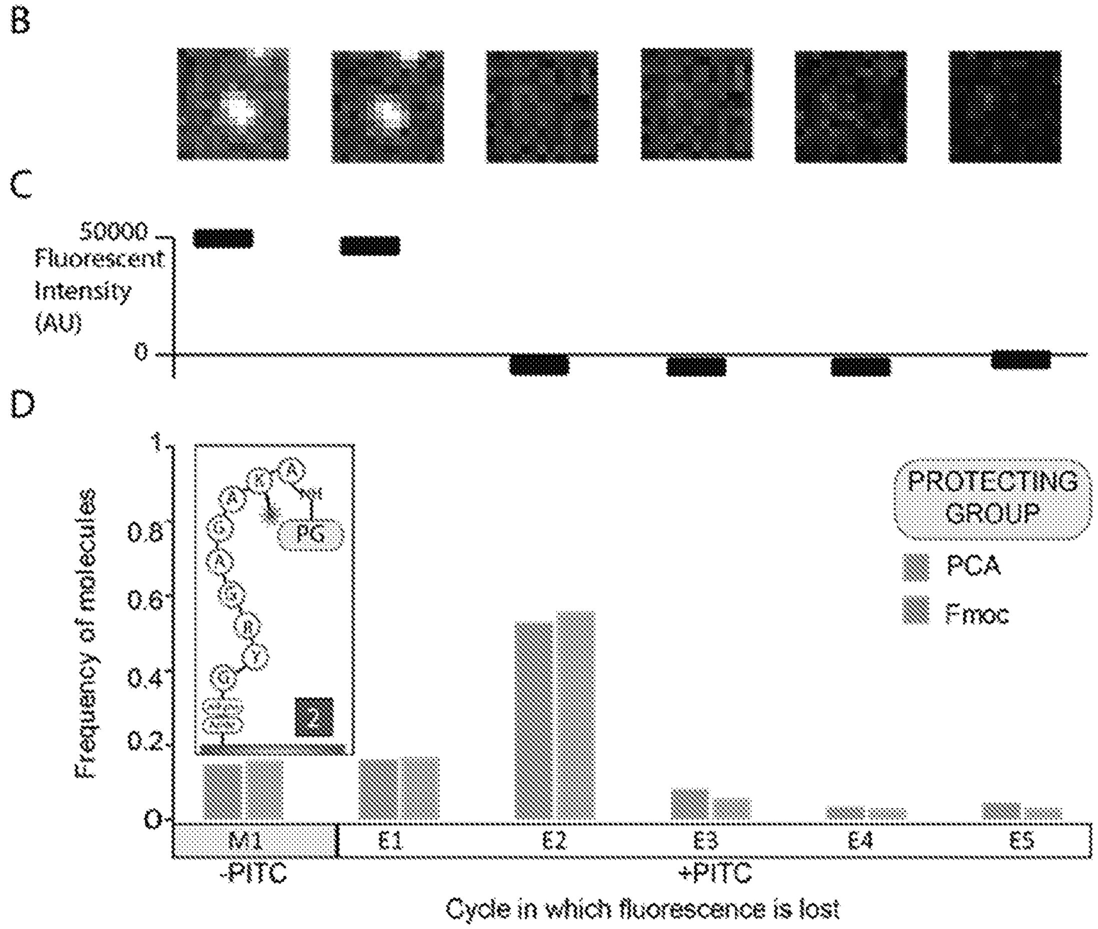

The summary result of the fluorosequencing experiment performed on >50,000 peptide molecules is shown in the bar chart (FIG. 15A-D). FIG. 15A is a representative field of view from a fluorosequencing experiment. FIG. 15B are extracted images of an individual peptide across the Edman cycles with its subsequent loss after the second cycle. FIG. 15C shows the fluorescent intensity of the same peptide across Edman cycles. FIG. 15D illustrates the frequency of these single molecule tracks whose fluorescence was lost after each experimental cycle for both a PCA or Fmoc protected peptide. The experimental cycle comprises a control cycle (M1 is a "mock" cycle where the slide is washed with all reagents used in fluorosequencing without the reactive Phenylisothiocyanate (PITC)) and the Edman cycles (denoted as "E"). The frequency counts of peptide molecule tracks with loss of fluorescence observed after every individual experimental cycle (M=Mock or control cycle with reactive PITC; E=Edman cycle) indicates that the major loss occurred after the 2nd Edman cycle or after the cleavage of the 2nd Amino acid (which in this case is fluorescently labeled Atto647N dye). After performing fluorosequencing experiment, the Atto647N label was detected at the 2nd position (FIG. 15). This demonstrates the feasibility of the resin-based peptide capture technology for single molecule peptide sequencing analysis.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Andrews et al., *J. Biol. Chem.,* 283:32412-32418, 2008.
Baez et al., *Free radical biology & medicine,* 80:191-211, 2015.
Duffy et al., *Eur. J. Cancer,* 75:284-298, 2017.
Dunn et al., *Mass Spectrometry Reviews,* 2009.
Gnjatic et al., *J. Immunother. Cancer,* 5:44, 2017.
Hwang, et al., *J Proteome Res,* 2018.
Jin et al., *Chem Soc Rev,* 42(16):6634-54, 2013.
Klement et al., *J. Proteome Res.,* 9:2200-2206, 2010.
Koo et al., *Biomacromolecules,* 2019.
Kool et al., Organic Letters, 16(5):1454-1457, 2014.
Lang and Chin, *Chemical Reviews,* 114(9):4764-4806, 2014.
Lee, *Endocrinol* Metab (Seoul), 32(1):18-22, 2017.
Lin and Garcia, 512:3-28, 2012.

Lin et al., *Efforts and Challenges in Engineering the Genetic Code*. Life (Basel), 7(1), 2017.
MacDonald et al., *Nat. Chem. Bio.*, 11:326, 2015.
Mazzone et al., *Am. J. Respir. Crit. Care Med.*, 196:e15-e29, 2017.
Merrifield, *J. Am. Chem. Soc.*, 85:2149-2154, 1963.
Quick et al., *Journal of The American Society for Mass Spectrometry*, 28(7):1462-1472, 2017.
Saiz et al., Organic Letters, 11(15):3170-3173, 2009.
Schwammle et al., *Molecular & Cellular Proteomics*, 13(7): 1855-1865, 2014.
Shimko et al., *Methods in Molecular Biology*, 981:177-192, 2013.
Steen et al., *Mol Cell Proteomics*, 5(1):172-81, 2006.
Swaminathan et al., *Nature Biotechnology*, 2018.
Villain et al., *Chemistry & Biology*, 8(7):673-679, 2001.
Waliczek et al., *Sci Rep*, 6:37720, 2016.
Wiese et al., *Proteomics*, 7:340-350, 2007.

What is claimed is:
1. A conjugating group selected from the group consisting of:
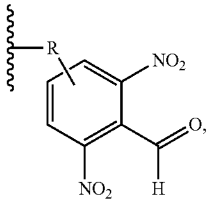
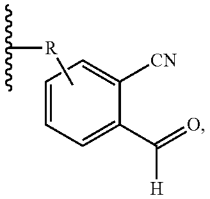
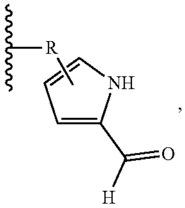
,
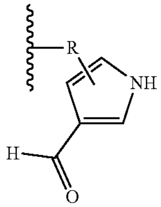
,
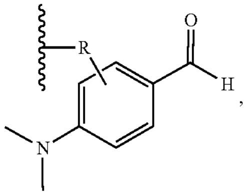
,
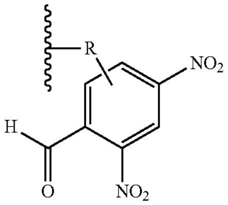
,
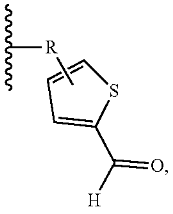
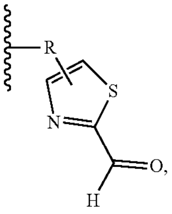
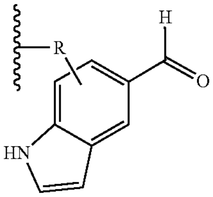
,
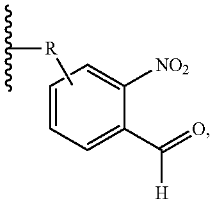
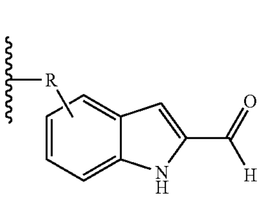
,
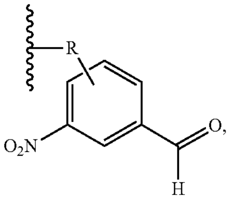
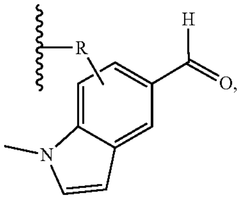
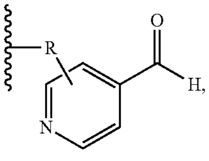
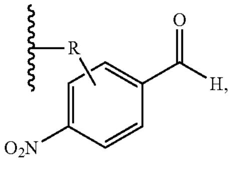
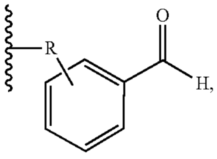
-continued
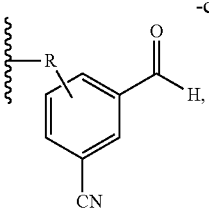
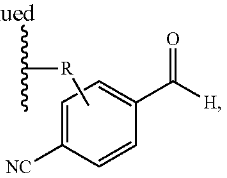
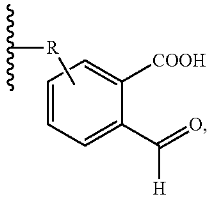
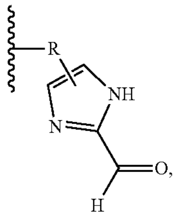
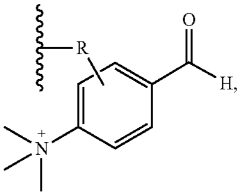
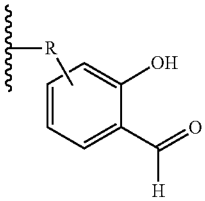
,
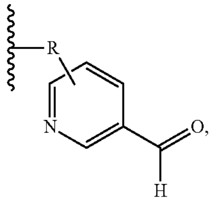
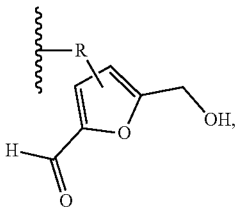
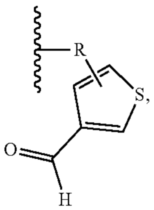
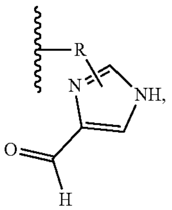
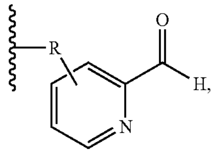
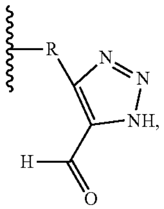
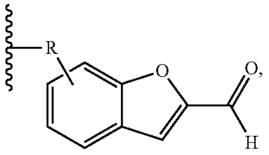
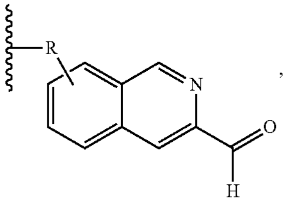
,
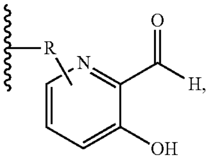
and
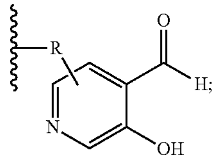
wherein the aromatic or heteroaromatic ring of the above formulas is optionally substituted with one or more functional groups, each independently selected from the group consisting of amino, cyano, halo, hydroxy, nitro, and a group of the formula: —[N($R_a$)($R_b$)($R_c$)]*, wherein $R_a$, $R_b$, and $R_c$ are each independently selected from the group consisting of hydrogen and optionally substituted $C_1$-$C_8$ alkyl;

"" represents an attachment point to a solid support; and

R comprises a Rink linker and/or a polyethylene glycol linker.

2. The conjugating group of claim 1, wherein said solid support comprises a resin or a bead.

3. The conjugating group of claim 1, wherein R is coupled to an amine of said solid support.

4. The conjugating group of claim 1, wherein said conjugating group is configured to couple to an N-terminal amino acid of a peptide.

5. The conjugating group of claim 4, wherein said conjugating group is configured to reversibly couple to said N-terminal amino acid of said peptide.

6. The conjugating group of claim 4, wherein said conjugating group is configured to couple to said N-terminal amino acid of said peptide to generate a structure comprising:

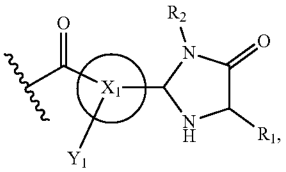

wherein, $X_1$ and $Y_1$ is the conjugating group;

$R_1$ is a side chain of an N-terminal amino acid of said peptide, and $R_2$ comprises additional amino acids of said peptide.

* * * * *